(12) United States Patent
Sato et al.

(10) Patent No.: US 10,241,315 B2
(45) Date of Patent: Mar. 26, 2019

(54) IMAGE ACQUISITION DEVICE, IMAGE FORMING SYSTEM, AND IMAGE FORMING METHOD

(71) Applicant: Panasonic Intellectual Property Management Co., Ltd., Osaka (JP)

(72) Inventors: Taichi Sato, Kyoto (JP); Yoshihide Sawada, Kyoto (JP); Yasuhiko Adachi, Hyogo (JP); Hideto Motomura, Kyoto (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 170 days.

(21) Appl. No.: 15/224,712

(22) Filed: Aug. 1, 2016

(65) Prior Publication Data

US 2016/0341947 A1 Nov. 24, 2016

(30) Foreign Application Priority Data

Nov. 27, 2014 (JP) ................................. 2014-239443

(51) Int. Cl.
*G03H 1/08* (2006.01)
*G06K 9/00* (2006.01)
(Continued)

(52) U.S. Cl.
CPC ........... *G02B 21/365* (2013.01); *G01N 21/59* (2013.01); *G02B 21/0008* (2013.01);
(Continued)

(58) Field of Classification Search
None
See application file for complete search history.

(56) References Cited

U.S. PATENT DOCUMENTS 4,411,489 A * 10/1983 McGrew .............. G03H 1/0406
   359/23
4,806,776 A * 2/1989 Kley .................... G02B 21/088
   250/225
(Continued)

FOREIGN PATENT DOCUMENTS

JP 62-137037 6/1987
WO 2013/019640 A1 2/2013

OTHER PUBLICATIONS

International Search Report of PCT application No. PCT/JP2015/005545 dated Jan. 26, 2016.
(Continued)

*Primary Examiner* — Mohammad J Rahman
(74) *Attorney, Agent, or Firm* — McDermott Will & Emery LLP

(57) ABSTRACT

An image acquisition device according to the present disclosure includes a lighting system and an irradiation direction decision section. In a module, a subject and an imaging element are integrally formed. The lighting system sequentially irradiates the subject with illumination light in a plurality of different irradiation directions based on the subject such that the illumination light transmitted through the subject is incident on the imaging element. The module acquires a plurality of images according to the plurality of different irradiation directions. Before the plurality of images are acquired according to the plurality of different irradiation directions, the irradiation direction decision section decides the plurality of different irradiation directions based on a difference between a first preliminary image and a second preliminary image. The first preliminary image is acquired when the subject is irradiated with first illumination light in a first irradiation direction, and the second prelimi-
(Continued)

nary image is acquired when the subject is irradiated with second illumination light in a second irradiation direction.

28 Claims, 44 Drawing Sheets

(51) Int. Cl.
*G06T 7/00* (2017.01)
*G01B 9/021* (2006.01)
*G02B 21/36* (2006.01)
*G02B 21/06* (2006.01)
*H04N 5/225* (2006.01)
*H04N 5/232* (2006.01)
*H04N 5/235* (2006.01)
*G01N 21/59* (2006.01)
*G02B 21/00* (2006.01)
*G02B 21/08* (2006.01)
*G02B 21/26* (2006.01)
*G01N 21/49* (2006.01)

(52) U.S. Cl.
CPC ............ *G02B 21/06* (2013.01); *G02B 21/086* (2013.01); *G02B 21/26* (2013.01); *H04N 5/2256* (2013.01); *H04N 5/2354* (2013.01); *H04N 5/2356* (2013.01); *H04N 5/23232* (2013.01); *G01N 21/49* (2013.01); *G01N 2201/0662* (2013.01)

(56) References Cited

U.S. PATENT DOCUMENTS

| | | | | | |
|---|---|---|---|---|---|
| 6,646,809 | B1* | 11/2003 | Ishino | ................ | G02B 27/0172 359/630 |
| 7,636,494 | B2* | 12/2009 | Kudo | .................. | H04N 5/3675 348/246 |
| 7,750,957 | B2* | 7/2010 | Shimazu | .............. | H04N 5/3456 250/208.1 |
| 7,865,076 | B2* | 1/2011 | Tamaki | .................. | G02B 5/003 396/307 |
| 8,085,334 | B2* | 12/2011 | Itakura | ................. | H04N 5/3454 348/335 |
| 8,804,112 | B2* | 8/2014 | Shibata | ............ | G01N 21/95607 356/237.4 |
| 8,908,074 | B2* | 12/2014 | Oshima | ................ | H04N 5/3532 348/302 |
| 9,253,414 | B2* | 2/2016 | Yamagata | ............ | H04N 5/2621 |
| 9,808,147 | B2* | 11/2017 | Kanamori | ............ | A61B 1/0646 |
| 10,074,169 | B2* | 9/2018 | Niedermeier | ........ | G01N 21/909 |
| 2010/0198008 | A1* | 8/2010 | Kawano | ............ | A61B 1/00158 600/109 |
| 2011/0164804 | A1* | 7/2011 | Blair | ...................... | G07D 7/121 382/135 |
| 2014/0155759 | A1* | 6/2014 | Kaestle | ................ | A61B 5/0077 600/479 |
| 2015/0141753 | A1* | 5/2015 | Kanamori | ......... | H01L 27/14627 600/109 |
| 2015/0355102 | A1* | 12/2015 | Kido | .................. | G01N 21/8851 348/46 |

OTHER PUBLICATIONS

The Extended European Search Report dated Nov. 2, 2017 for the related European Patent Application No. 15864158.9.

Waheb Bishara: "Lensfree on-chip microscopy over a wide field-of-view using pixel super-resolution", Opt. Express, vol. 18, No. 11, May 24, 2010 (May 24, 2010), pp. 11181-11191, XP55066800.

Bishara W et ai: "Portable and cost-effective pixel super-resolution on-chip microscope for telemedicine applications", Engineering in Medicine ano Biology Society, EMBC, 2011 Annual International Conference of the IEEE, IEEE, Aug. 30, 2011 (Aug. 30, 2011), pp. 8207-8210, XP032320588.

* cited by examiner

IMAGE ACQUISITION DEVICE, IMAGE FORMING SYSTEM, AND IMAGE FORMING METHOD

BACKGROUND

1. Technical Field

The present disclosure relates to an image acquisition device, an image forming system, and an image forming method.

2. Description of the Related Art

Conventionally, an optical microscope is used to observe a microstructure of a living tissue or the like. Light transmitted through or reflected from an observation object is used in the optical microscope. An observer observes an image enlarged through a lens. There is also known a digital microscope that photographs the image enlarged through a lens and displays the image on a display. The use of the digital microscope enables simultaneous observation by a plurality of persons or remote observation.

Nowadays a technology of observing the microstructure by a CIS (Contact Image Sensing) scheme attracts attention. For the CIS scheme, the observation object is disposed in proximity to an imaging surface of an image sensor. A two-dimensional image sensor in which many photoelectric converters are two-dimensionally arrayed in the imaging surface is generally used as the image sensor. Typically the photoelectric converter is a photodiode formed in a semiconductor layer or a semiconductor substrate, and the photoelectric converter generates a charge by receiving incident light.

The image captured with the image sensor is defined by many pixels. Each pixel is divided by a unit region including one photoelectric converter. Accordingly, resolving power (resolution) of the two-dimensional image sensor usually depends on an array pitch of the photoelectric converter on the imaging surface. Hereinafter, sometimes the resolving power depending on the array pitch of the photoelectric converter is referred to as "intrinsic resolving power" of the image sensor. Because the array pitch of each photoelectric converter is shortened up to a degree of a wavelength of visible light, it is difficult to further improve the intrinsic resolving power.

There is proposed a technology of resolving power exceeding the intrinsic resolving power of the image sensor. PTL 1 discloses a technology of forming a subject image using a plurality of images obtained by a shift of an image formation position of a subject.

CITATION LIST

Patent Literature

PTL 1: Unexamined Japanese Patent Publication No. S62-137037

SUMMARY

One non-limiting and exemplary embodiment provides an image acquisition device, an image forming system, and an image forming method for improving practicability of a technology of high resolving power exceeding the intrinsic resolving power of the image sensor.

The following aspect is provided as an illustrative exemplary embodiment of the present disclosure.

In one general aspect, the techniques disclosed here feature an image acquisition device includes: a lighting system that sequentially irradiates a subject of a module with illumination light in a plurality of different irradiation directions, the subject and an imaging element being integrated with each other in the module such that the illumination light transmitted through the subject is incident on the imaging element, the imaging element for acquiring a plurality of images according to the plurality of different irradiation directions; and an irradiation direction decision section that decides the plurality of different irradiation directions based on a difference between a first preliminary image and a second preliminary image before the imaging element acquires the plurality of images according to the plurality of different irradiation directions, the first preliminary image being acquired with the imaging element when the subject is irradiated with first illumination light in a first irradiation direction, the second preliminary image being acquired with the imaging element when the subject is irradiated with second illumination light in a second irradiation direction.

The present disclosure improves practicability of the technology of high resolving power exceeding the intrinsic resolving power of the image sensor.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

It should be noted that general or specific embodiments may be implemented as a system, a method, an integrated circuit, a computer program, a storage medium, or any selective combination thereof.

DETAILED DESCRIPTION

Principle to Form High-Resolution Image

In an exemplary embodiment of the present disclosure, an image having the higher resolving power than that of each of a plurality of images (hereinafter, referred to as a "high-resolution image") is formed using the plurality of images that are photographed a plurality of times while an irradiation direction of illumination light is changed. A principle to form the high-resolution image will be described below with reference to FIGS. 1A to 6. In this case, a CCD (Charge Coupled Device) image sensor is illustrated. The component having the substantially same function is designated by the same reference sign, and sometimes the description is omitted.

Figure 1A:
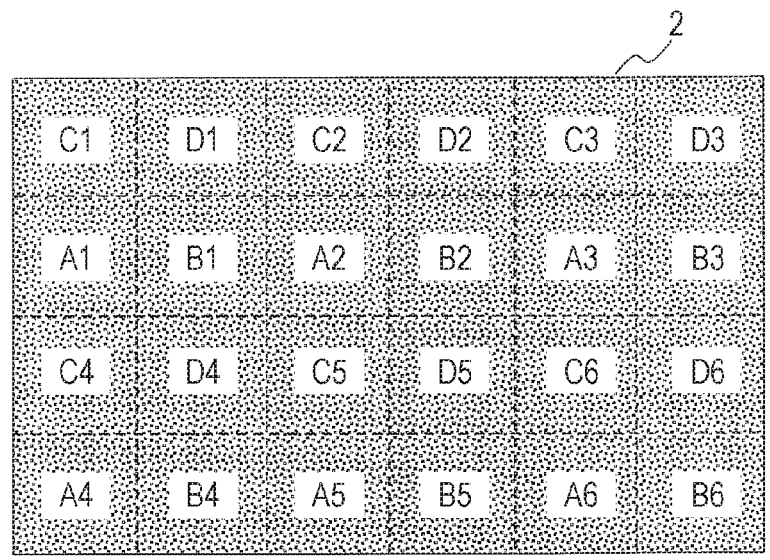
FIG. 1A is a plan view schematically illustrating a part of subject 2.

FIG. 1A is a plan view schematically illustrating a part of a subject. For example, subject 2 in FIG. 1A is a thin piece (typically the thin piece has a thickness of several tens of micrometers) of a biological tissue. In capturing the image of subject 2, subject 2 is disposed in proximity to the imaging surface of the image sensor. Typically a distance from the imaging surface of the image sensor to subject 2 is less than or equal to 1 mm. For example, the distance can be set to about 1 μm.

Figure 1B:
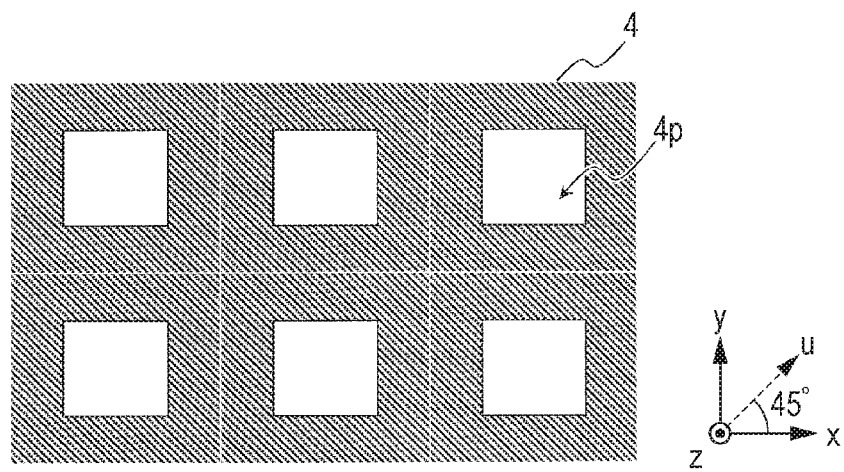
FIG. 1B is a plan view schematically illustrating photodiodes relating to imaging of a region in FIG. 1A.

FIG. 1B is a plan view schematically illustrating photodiodes relating to imaging of a region in FIG. 1A in photodiodes of the image sensor. Six photodiodes are illustrated in photodiodes 4p formed in image sensor 4. For reference, arrows indicating an x-direction, a y-direction, and a z-direction, which are orthogonal to one another, are illustrated in FIG. 1B. The z-direction indicates a direction normal to the imaging surface. An arrow indicating a u-direction that is of a direction rotated by 45° from an x-axis to a y-axis in an xy-plane is also illustrated in FIG. 1B. Sometimes the arrows indicating the x-direction, y-direction, z-direction, and u-direction are illustrated in other drawings.

The components except for photodiodes 4p in image sensor 4 are covered with a light shielding layer. In FIG. 1B, a hatched region indicates a region covered with the light shielding layer. An area of a light receiving surface of one photodiode on the imaging surface of the CCD image sensor (S2) is smaller than an area of the unit region including the photodiode (S1). A ratio of light receiving area S2 to area S1 of the pixel (S2/S1) is referred to as a "numerical aperture". At this point, it is assumed that a numerical aperture is 25%.

Figure 2A:
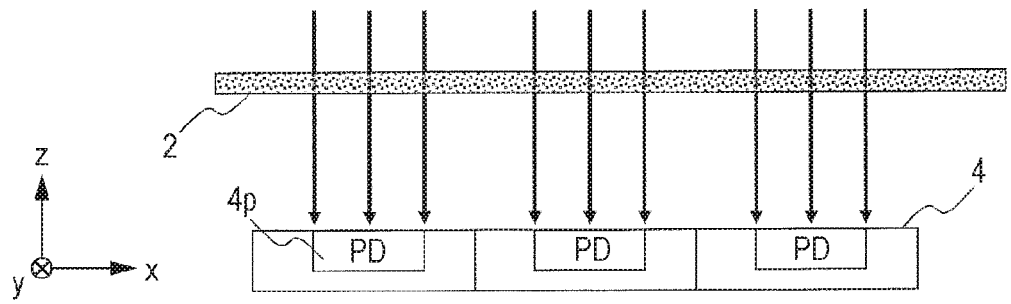
FIG. 2A is a sectional view schematically illustrating a direction of a beam incident on photodiode 4$p$ through subject 2.
Figure 2B:
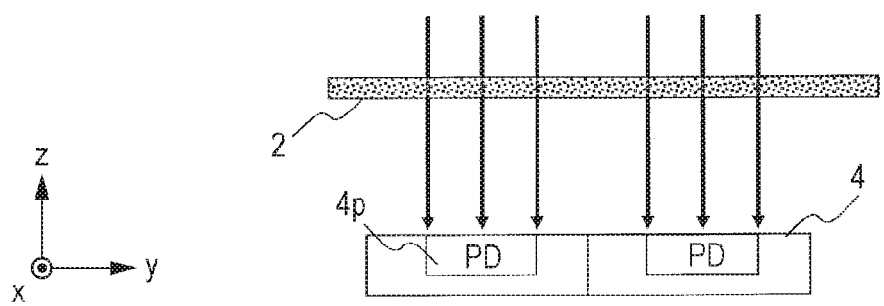
FIG. 2B is a sectional view schematically illustrating the direction of the beam incident on photodiode 4$p$ through subject 2.

FIGS. 2A and 2B schematically illustrate the direction of a beam incident on photodiode 4p through subject 2. FIGS. 2A and 2B illustrate a state in which the beam is incident in a direction perpendicular to an imaging surface. As schematically illustrated in FIGS. 2A and 2B, an image formation lens is not disposed between subject 2 and image sensor 4, but the image of subject 2 is captured using a substantially parallel beam transmitted through subject 2.

Figure 2C:
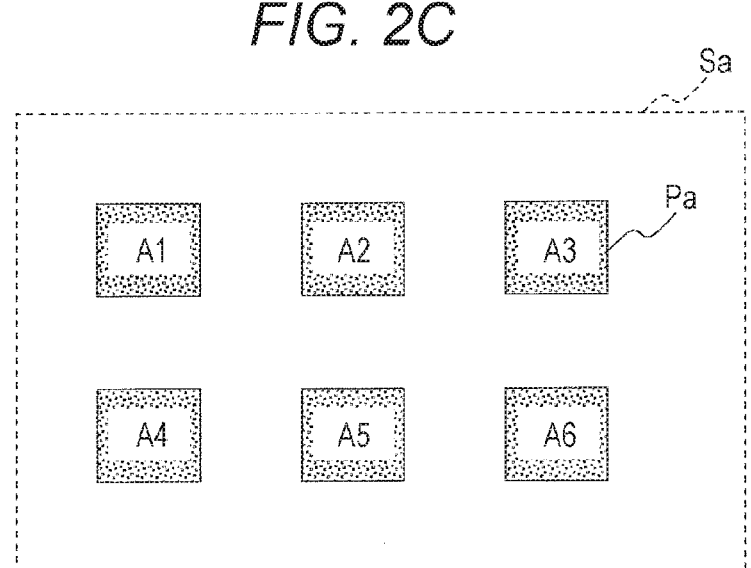
FIG. 2C is a view schematically illustrating six pixels Pa acquired with six photodiodes 4$p$.

FIG. 2C schematically illustrates image Sa acquired in the irradiation direction of FIGS. 2A and 2B (first sub-image Sa). As illustrated in FIG. 2C, first sub-image Sa includes six pixels Pa acquired with six photodiodes 4p. Each of pixels Pa has a value indicating an amount of light incident to individual photodiode 4p (pixel value).

As illustrated in FIGS. 2A and 2B, when subject 2 is irradiated with illumination light in a direction perpendicular to the imaging surface, the light transmitted through the region located immediately above photodiode 4p in whole subject 2 is incident on photodiode 4p. In this example, first sub-image Sa has pieces of information about regions A1, A2, A3, A4, A5, and A6 (see FIG. 1A) in whole subject 2. The light transmitted through the region, which is not located immediately above photodiode 4p, is not incident on photodiode 4p. Accordingly, information about a region except for regions A1, A2, A3, A4, A5, and A6 in whole subject 2 is missing in first sub-image Sa.

Figure 3A:
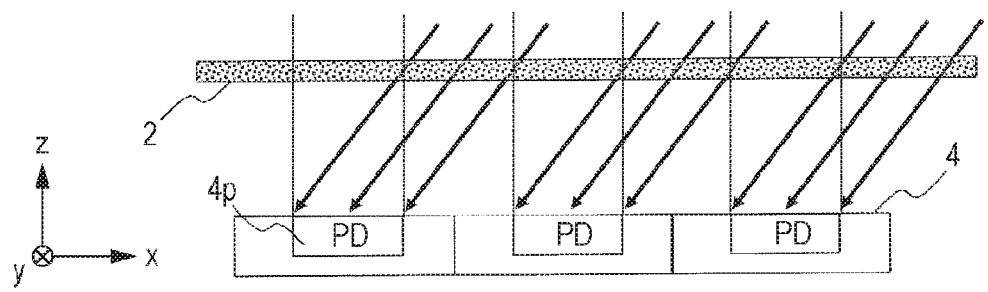
FIG. 3A is a sectional view schematically illustrating a state in which the beam is incident in an irradiation direction different from the irradiation direction in FIGS. 2A and 2B.
Figure 3B:
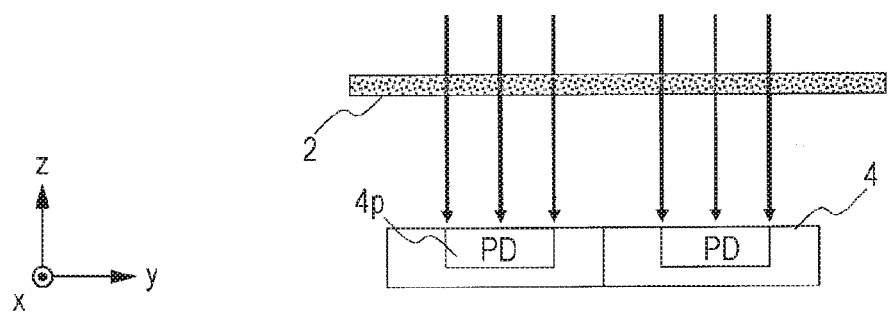
FIG. 3B is a sectional view schematically illustrating the state in which the beam is incident in the irradiation direction different from the irradiation direction in FIGS. 2A and 2B.

FIGS. 3A and 3B illustrate the state in which the beam is incident in an irradiation direction different from the irradiation direction in FIGS. 2A and 2B. The beam in FIGS. 3A and 3B is tilted in an x-direction with respect to a z-direction. At this point, the light transmitted through the region different from the region located immediately above photodiode 4p in whole subject 2 is incident on photodiode 4p.

Figure 3C:
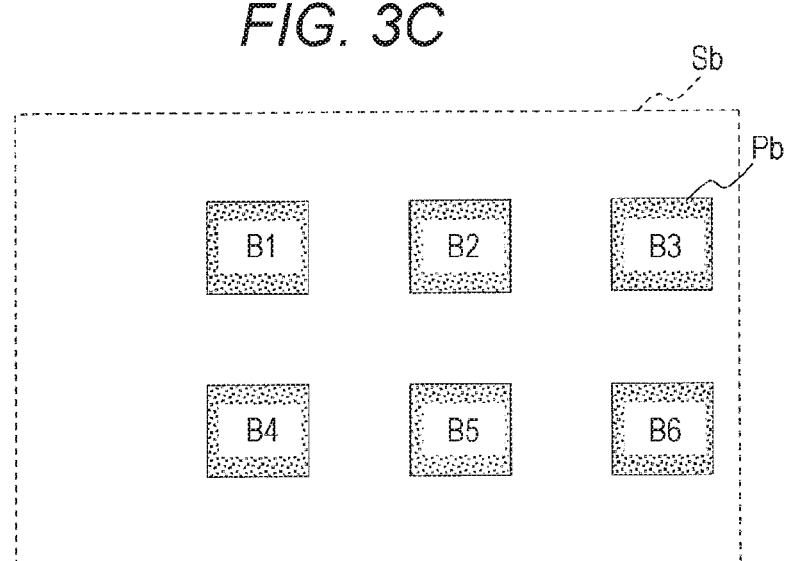
FIG. 3C is a view schematically illustrating six pixels Pb acquired in the irradiation direction in FIGS. 3A and 3B.

FIG. 3C schematically illustrates image Sb acquired in the irradiation direction of FIGS. 3A and 3B (second sub-image Sb). As illustrated in FIG. 3C, second sub-image Sb also includes six pixels Pb acquired with six photodiodes 4p. However, pixel Pb constituting second sub-image Sb has the pixel value relating to each of regions B1, B2, B3, B4, B5, and B6 (see FIG. 1A) different from regions A1, A2, A3, A4, A5, and A6 in whole subject 2. In other words, second sub-image Sb has not the pieces of information about regions A1, A2, A3, A4, A5, and A6 but pieces of information about regions B1, B2, B3, B4, B5, and B6 in whole subject 2. For example, region B1 is one adjacent to the right side of region A1 in subject 2 (see FIG. 1A).

As can be seen from a comparison of FIGS. 2A and 2B to FIGS. 3A and 3B, the beams transmitted through the different regions of subject 2 can be incident on photodiode 4p by a proper change of the irradiation direction. As a result, first sub-image Sa and second sub-image Sb can include the pieces of pixel information corresponding to the different positions in subject 2.

Figure 4A:
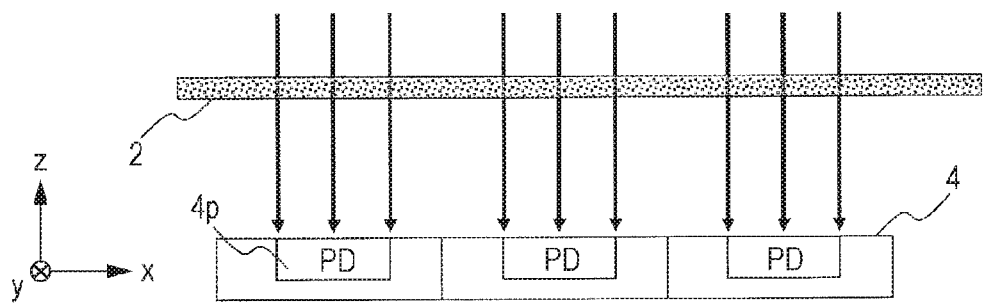
FIG. 4A is a sectional view schematically illustrating a state in which the beam is incident in an irradiation direction different from the irradiation directions in FIGS. 2A and 2B and 3A and 3B.
Figure 4B:
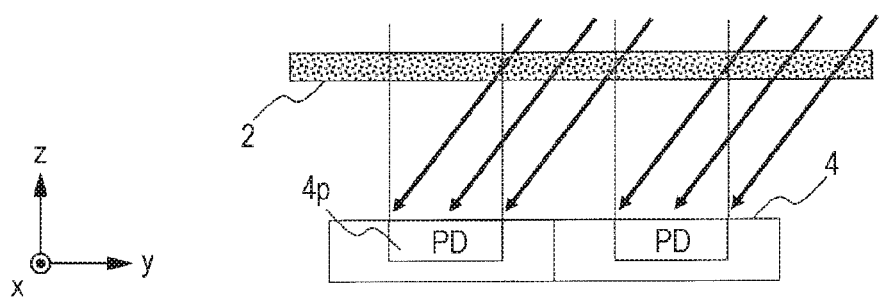
FIG. 4B is a sectional view schematically illustrating the state in which the beam is incident in an irradiation direction different from the irradiation directions in FIGS. 2A and 2B and 3A and 3B.

FIGS. 4A and 4B illustrate the state in which the beam is incident in an irradiation direction different from the irradiation directions in FIGS. 2A and 2B and 3A and 3B. The beam in FIGS. 4A and 4B is tilted in a y-direction with respect to the z-direction.

Figure 4C:
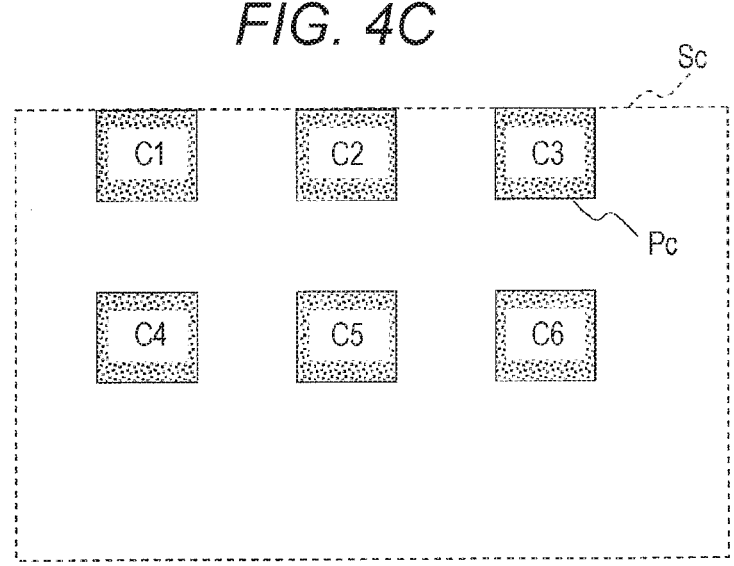
FIG. 4C is a view schematically illustrating six pixels Pc acquired in the irradiation direction in FIGS. 4A and 4B.

FIG. 4C schematically illustrates image Sc acquired in the irradiation direction of FIGS. 4A and 4B (third sub-image Sc). As illustrated in FIG. 4C, third sub-image Sc includes six pixels Pc acquired with six photodiodes 4p. As illustrated in FIG. 4C, third sub-image Sc has pieces of information about regions C1, C2, C3, C4, C5, and C6 in FIG. 1A in whole subject 2. For example, region C1 is one adjacent to the upper side of region A1 in subject 2 (see FIG. 1A).

Figure 5A:
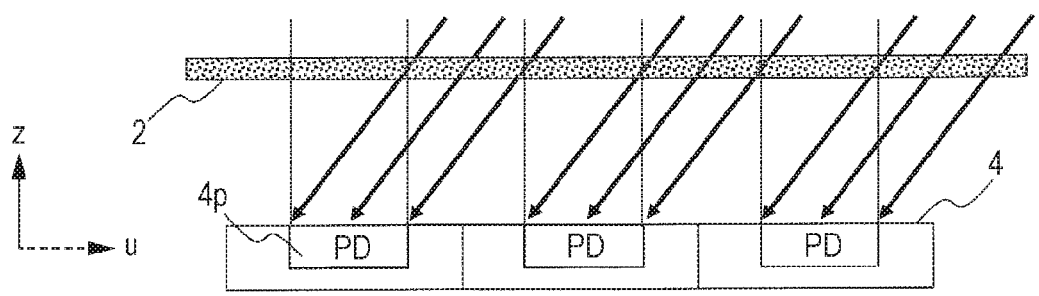
FIG. 5A is a sectional view schematically illustrating a state in which the beam is incident in an irradiation direction different from the irradiation directions in FIGS. 2A and 2B, 3A and 3B, 4A and 4B.

FIG. 5A illustrates a state in which the beam is incident in an irradiation direction different from the irradiation directions in FIGS. 2A and 2B, 3A and 3B, 4A and 4B. The beam in FIG. 5A is tilted in the direction of an angle 45° formed between the z-direction and the x-axis in the xy-plane.

Figure 5B:
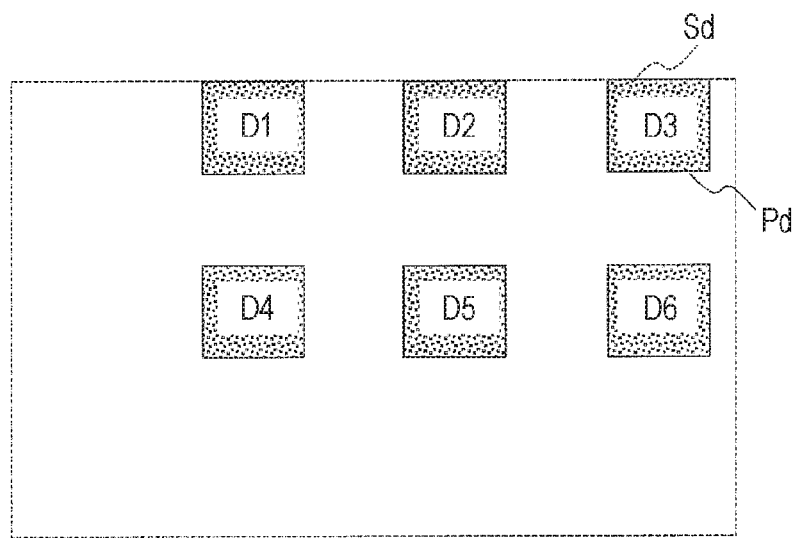
FIG. 5B is a view schematically illustrating six pixels Pd acquired in the irradiation direction in FIG. 5A.

FIG. 5B schematically illustrates image Sd acquired in the irradiation direction of FIG. 5A (fourth sub-image Sd). As illustrated in FIG. 5B, fourth sub-image Sd includes six pixels Pd acquired with six photodiodes 4p. Fourth sub-image Sd has pieces of information about regions D1, D2, D3, D4, D5, and D6 in FIG. 1A in whole subject 2. For example, region D1 is one adjacent to the right of region C1 (see FIG. 1A). Each of four sub-images Sa, Sb, Sc, and Sd includes the image constructed with a different part of subject 2.

Figure 6:
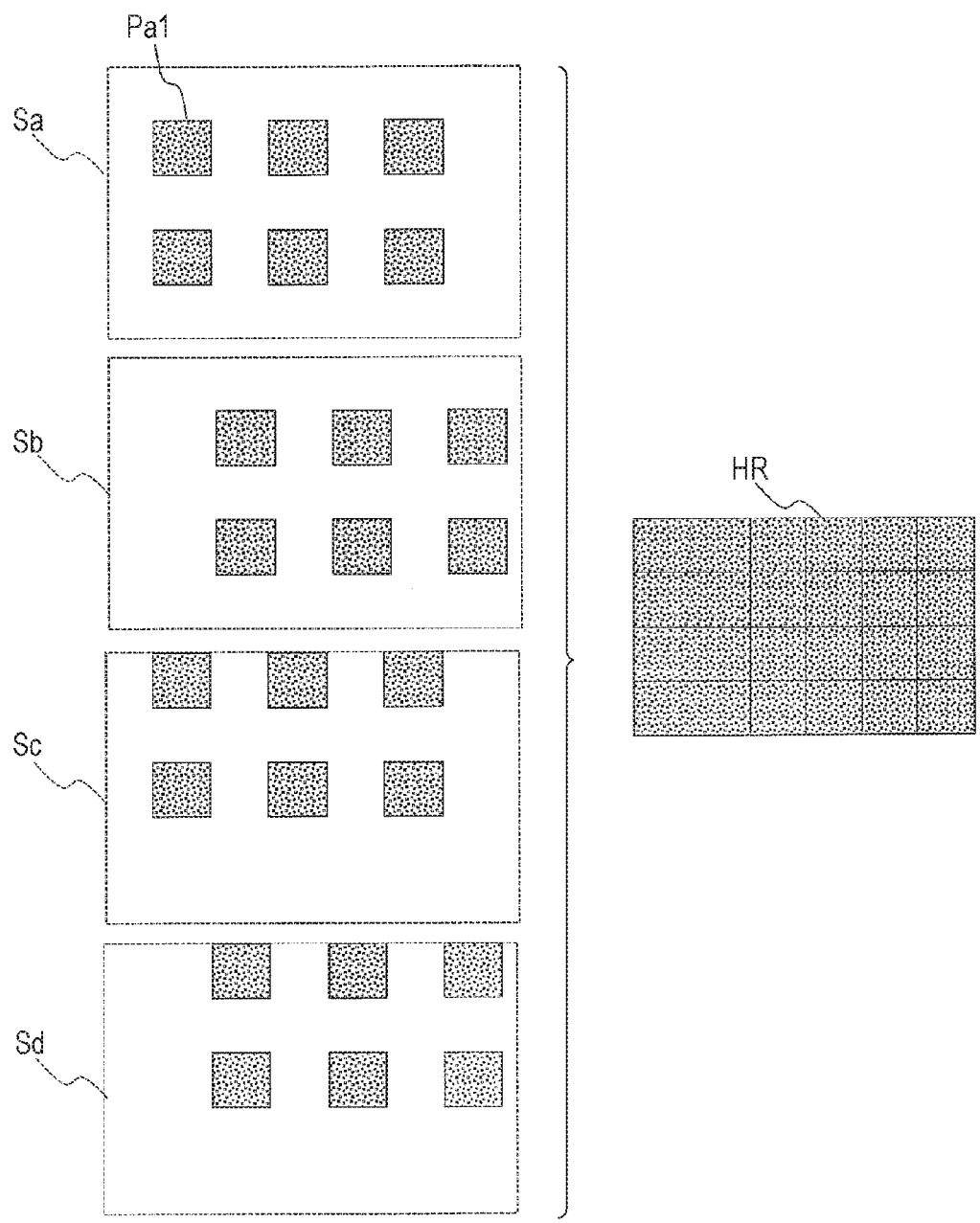
FIG. 6 is a view illustrating high-resolution image HR synthesized from four sub-images Sa, Sb, Sc, and Sd.

FIG. 6 illustrates high-resolution image HR synthesized from four sub-images Sa, Sb, Sc, and Sd. As illustrated in FIG. 6, a number of pixels or a pixel density of high-resolution image HR is four times the number of pixels or the pixel density of each of four sub-images Sa, Sb, Sc, and Sd.

For example, the blocks of regions A1, B1, C1, and D1 in FIG. 1A in subject 2 are described in detail. As can be seen from the above description, pixel Pa1 of sub-image Sa in FIG. 6 has the information not about the whole block but about only region A1. Accordingly, sub-image Sa is an image in which the pieces of information about regions B1, C1, and D1 are missing.

However, using sub-images Sb, Sc, and Sd having the pieces of pixel information corresponding to the different positions in subject 2, the information that is missing in sub-image Sa can be complemented to form high-resolution image HR having the information about the whole block as illustrated in FIG. 6. In FIG. 6, the resolving power four times the intrinsic resolving power of image sensor 4 is obtained whereas the resolving power of the individual sub-image is equal to the intrinsic resolving power of image sensor 4. The degree of the high resolving power (super-resolution) depends on the numerical aperture of the image sensor. In FIG. 6, because image sensor 4 has the numerical aperture of 25%, at most four times in high resolving power is achieved by the light irradiation in four different directions. At most N times in high resolving power can be obtained when the numerical aperture of image sensor 4 is approximately equal to 1/N (N is an integer of 2 or more).

Thus, the subject is irradiated with the parallel light and a picture of the subject is sequentially taken in the plurality of different irradiation directions based on the subject, which allows the increase of the pixel information spatially sampled from the subject. The high-resolution image having the higher resolving power than that of each of the plurality of sub-images can be formed by synthesizing of the plurality of obtained sub-images. The irradiation direction is not limited to ones in FIGS. 2A to 5B.

Figure 7:
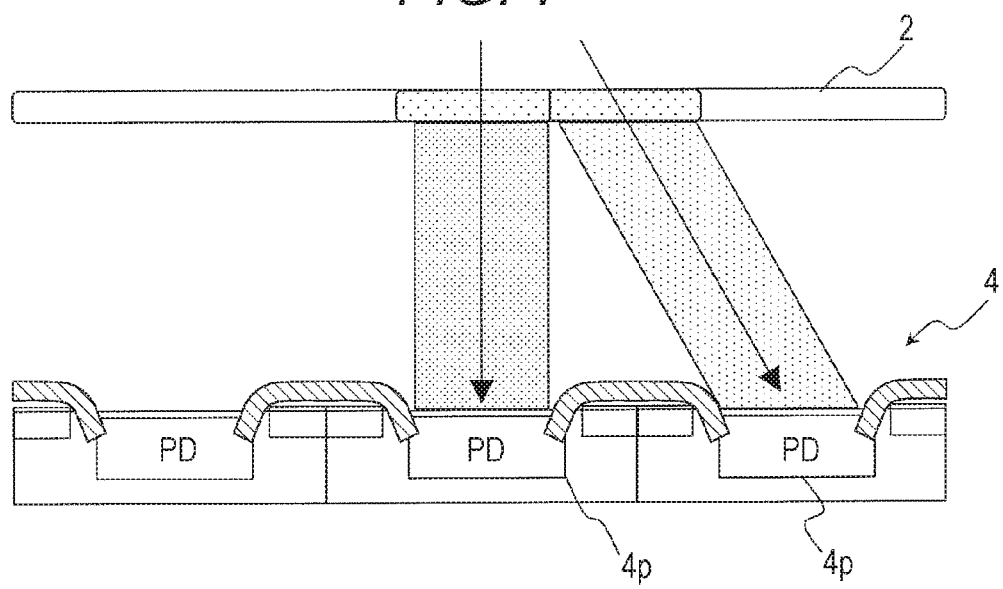
FIG. 7 is a sectional view schematically illustrating an irradiation direction in which beams passing through two adjacent regions in subject 2 are incident on different photodiodes.

In the FIG. 6, sub-images Sa, Sb, Sc, and Sd have the pieces of pixel information about the regions different from one another in subject 2, but the pieces of pixel information do not overlap one another. Alternatively, the different sub-images may overlap each other. In the above example, the beams passing through the two regions adjacent to each other in subject 2 are incident on the same photodiode. However, the setting of the irradiation direction is not limited to this example. For example, as illustrated in FIG. 7, the irradiation direction may be adjusted such that the beams passing through the two adjacent regions in subject 2 are incident on the different photodiodes.

(Module)

In the formation of the high-resolution image based on the principle described with reference to FIGS. 1A to 6, the sub-image is acquired while subject 2 is disposed in proximity to the imaging surface of image sensor 4. In the exemplary embodiment, the sub-image is acquired using a module having a structure in which subject 2 and image sensor 4 are integrated with each other. A configuration example of the module and an example of a module preparing method will be described below with reference to the drawings.

Figure 8A:
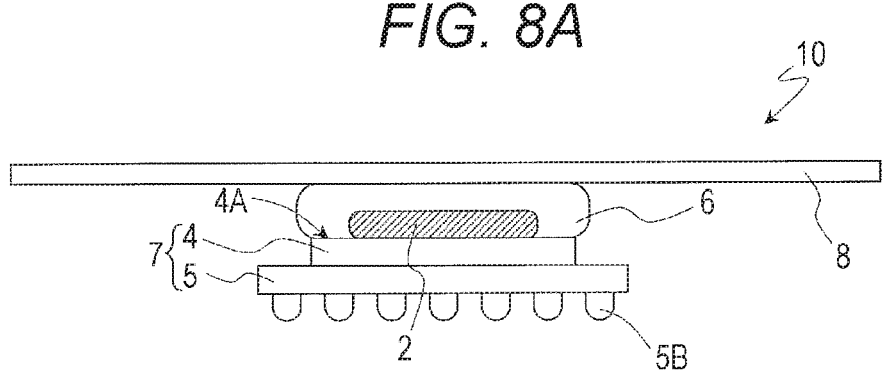
FIG. 8A is a view schematically illustrating an example of a sectional structure of a module.

FIG. 8A schematically illustrates an example of a sectional structure of the module. In module 10 of FIG. 8A, subject 2 covered with encapsulant 6 is disposed on imaging surface 4A of image sensor 4. In FIG. 8A, transparent plate (typically, glass plate) 8 is disposed on subject 2. That is, in the configuration of FIG. 8A, subject 2 is sandwiched between image sensor 4 and transparent plate 8. Workability is improved when module 10 usefully includes transparent plate 8. For example, a general slide glass can be used as transparent plate 8. Each component is schematically illustrated in FIG. 8A, but actual size and shape of each component are not always matched with the size and shape in FIG. 8A. The same holds true for the other drawings.

Figure 8B:
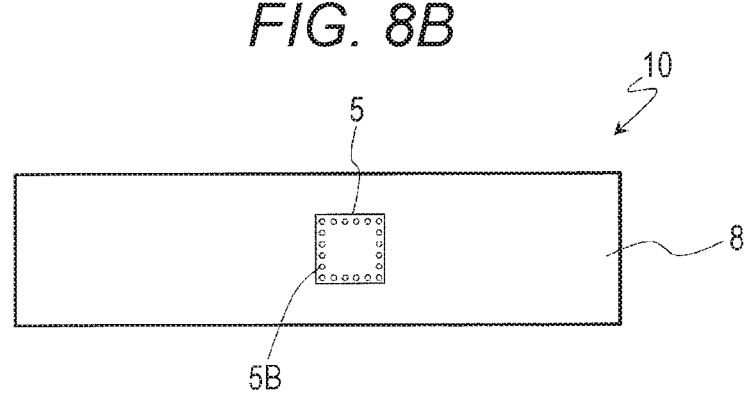
FIG. 8B is a plan view illustrating an example of an appearance when module 10 in FIG. 8A is viewed from a side of image sensor 4.

In the configuration of FIG. 8A, image sensor 4 is fixed to package 5. FIG. 8B illustrates an example of an appearance when module 10 in FIG. 8A is viewed from a side of image sensor 4. As illustrated in FIGS. 8A and 8B, package 5 includes rear surface electrode 5B located on an opposite surface to transparent plate 8. Rear surface electrode 5B is electrically connected to image sensor 4 through a wiring pattern (not illustrated) formed in package 5. That is, output of image sensor 4 can be taken out through rear surface electrode 5B. Hereinafter, a structure in which the package and the image sensor are integrally formed is referred to as an "imaging element".

An example of a method for preparing module 10 will be described with reference to FIG. 9. A thin piece (tissue slice) of the biological tissue is illustrated as subject 2. Module 10 with the thin piece of the biological tissue as subject 2 can be used in pathological diagnosis.

Figure 9:
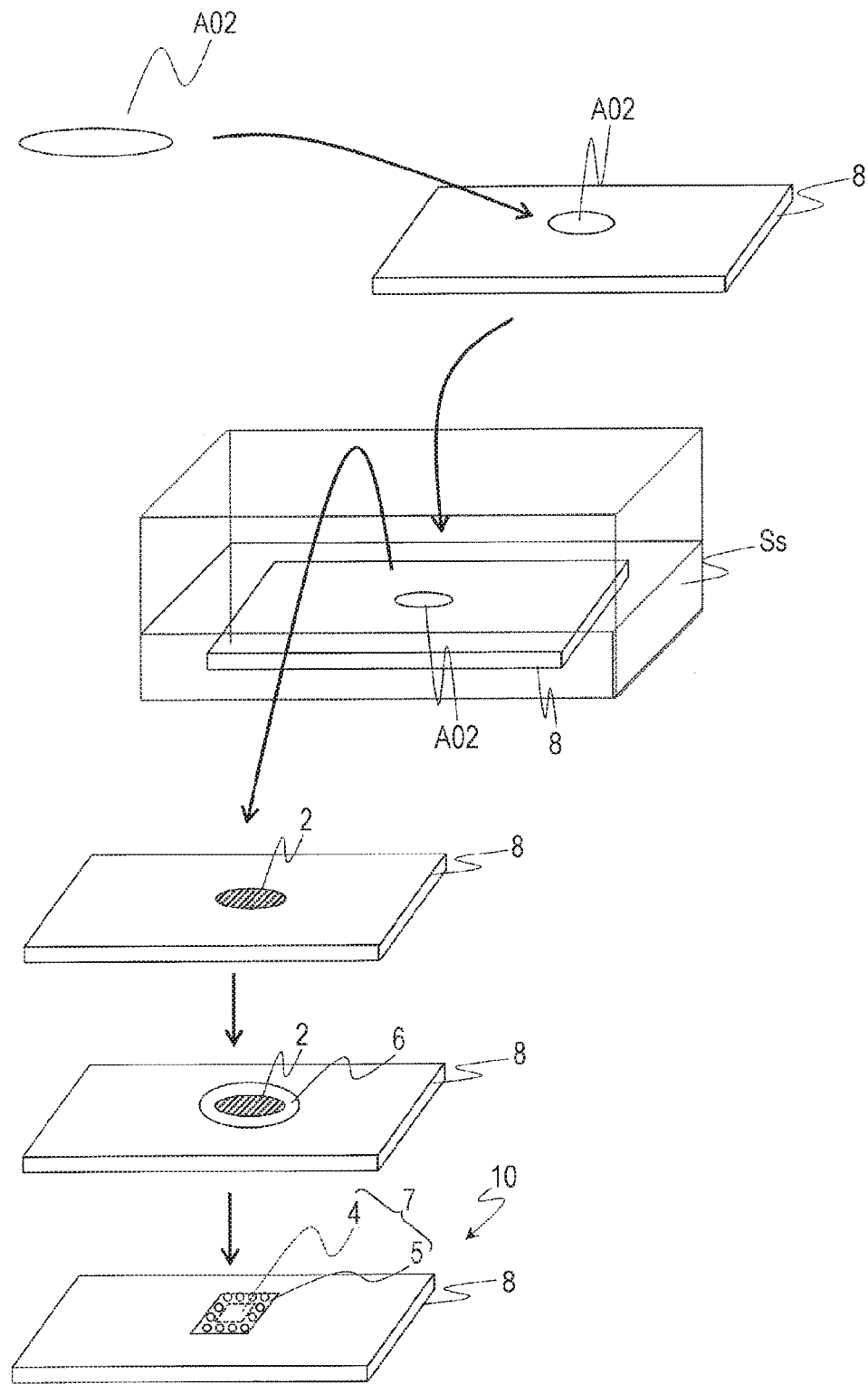
FIG. 9 is a view illustrating an example of a module preparing method.

As illustrated in FIG. 9, tissue slice A02 is placed on transparent plate 8. For example, transparent plate 8 is a slide glass that is used in the observation of a sample with the optical microscope. The slide glass is illustrated as transparent plate 8. Then, tissue slice A02 is dipped in dyeing solution Ss together with transparent plate 8, thereby dyeing tissue slice A02. Then, encapsulant 6 is provided onto transparent plate 8, and subject 2 obtained by the dyeing of tissue slice A02 is covered with encapsulant 6. Encapsulant 6 has a function of protecting subject 2. Then, imaging element 7 is disposed on subject 2 while the imaging surface of image sensor 4 faces subject 2. Therefore, module 10 is obtained.

Module 10 is prepared in each imaging object. For example, in a scene of the pathological diagnosis, a plurality (for example, 5 to 20) of tissue slices are prepared from one specimen. Therefore, a plurality of modules 10 having the tissue slices obtained from the same specimen as subject 2 can be prepared. The high-resolution image corresponding to each of the plurality of modules 10 can be formed when the plurality of sub-images are acquired with respect to each of the plurality of modules 10.

As illustrated in FIG. 8A, module 10 includes not a preparation used in the observation with the optical microscope, but image sensor 4 that acquires the image of subject 2. The module may be referred to as an "electronic preparation". As illustrated in FIG. 8A, dispositions of subject 2 and image sensor 4 can be fixed using module 10 having the structure in which subject 2 and imaging element 7 are integral with each other.

Figure 10A:
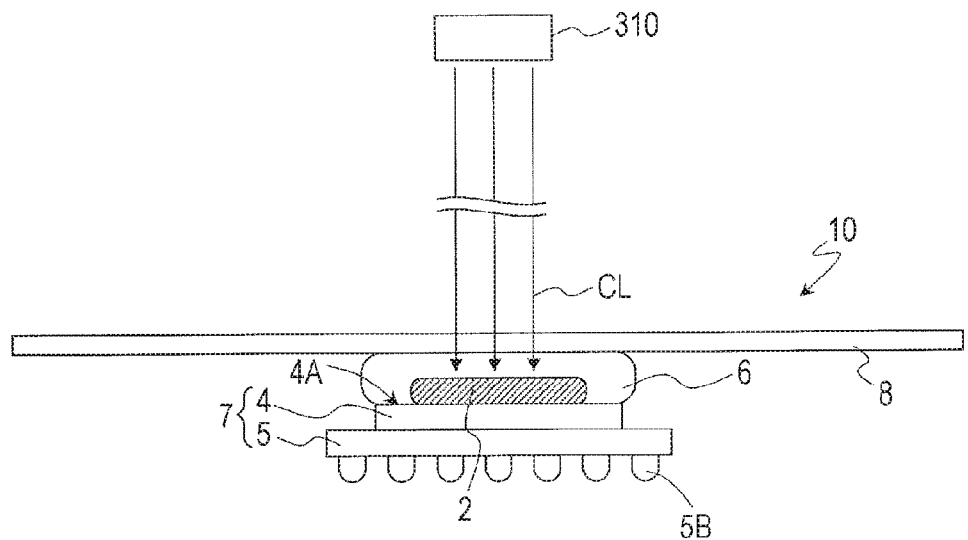
FIG. 10A is a sectional view illustrating an example of an irradiation angle in acquiring a sub-image.
Figure 10B:
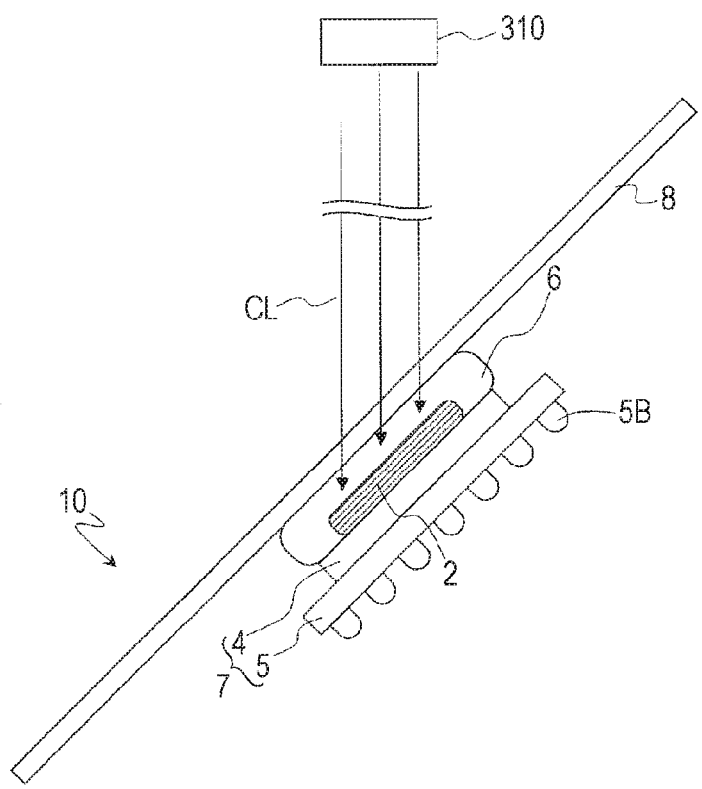
FIG. 10B is a sectional view illustrating an example of a method for irradiating the subject with illumination light at an irradiation angle different from the irradiation angle in FIG. 10A.

Subject 2 is irradiated with the illumination light through transparent plate 8 when the image of subject 2 is acquired using module 10. The illumination light transmitted through subject 2 is incident on image sensor 4. Therefore, the image of subject 2 is obtained. The imaging is sequentially performed while the relative disposition between the light source and the subject is changed, whereby the plurality of different images can be acquired while an angle is changed during irradiation. For example, as illustrated in FIG. 10A, light source 310 is disposed immediately above image sensor 4. A sub-image similar to sub-image Sa in FIG. 2C is obtained, when the imaging is performed while subject 2 is irradiated with collimated light CL in a direction normal to imaging surface 4A of image sensor 4. As illustrated in FIG. 10B, a sub-image similar to sub-image Sb in FIG. 3C (or sub-image Sc in FIG. 4C) is obtained, when subject 2 is irradiated with collimated light CL to perform the imaging with module 10 tilted. The imaging is sequentially performed while an attitude of module 10 is changed relative to the light source, whereby the high-resolution image can be obtained by applying the principle described with reference to FIGS. 1A to 6.

(Knowledge of the Inventor)

As described above with reference to FIGS. 1A to 6, in obtaining the plurality of sub-images, the irradiation is performed in the proper irradiation direction such that the sub-image suitable for the formation of the high-resolution image is obtained. However, it is difficult to previously recognize the relative disposition between the region through which the beam passes in subject 2 and the photodiode on which the transmitted beam is incident. Accordingly, generally it is difficult to decide the plurality of irradiation directions used to acquire the plurality of sub-images. Even if the plurality of irradiation directions can be decided with respect to one module, the plurality of irradiation directions are not always suitable for other modules as described below. That is, sometimes a proper high-resolution image can hardly be formed when the irradiation direction of the illumination light is shared with a plurality of modules.

Figure 11A:
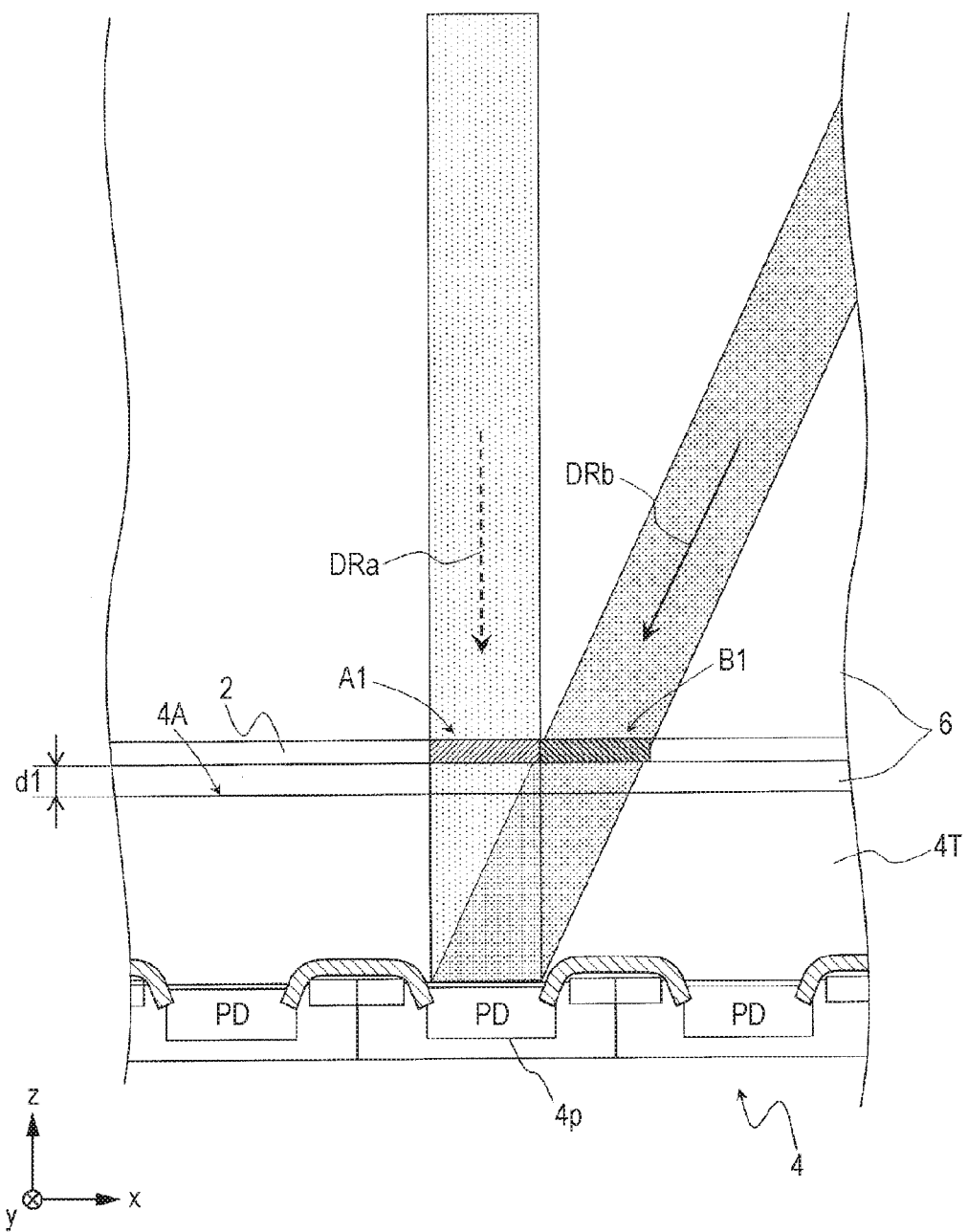
FIG. 11A is an enlarged sectional view schematically illustrating an example of a relationship between disposition of subject 2 and the irradiation direction.

FIG. 11A schematically illustrates an example of a relationship between the disposition of subject 2 and the irradiation direction. Both the irradiation direction indicated by broken-line arrow DRa and the irradiation direction indicated by solid-line arrow DRb are illustrated in FIG. 11A. As can be seen from the principle described with reference to FIGS. 1A to 6, the irradiation of the illumination light in the direction indicated by arrow DRa and the irradiation of the illumination light in the direction indicated by arrow DRb are not simultaneously performed, but sequentially performed during the actual imaging.

In the example of FIG. 11A, image sensor 4 includes transparent layer 4T covering a light incident surface of photodiode 4p. Subject 2 is located on transparent layer 4T while covered with encapsulant 6. In FIG. 11A, a gap between imaging surface 4A and subject 2 is schematically indicated by arrow d1.

As illustrated in FIG. 11A, when subject 2 is irradiated with illumination light in the irradiation direction indicated by arrow DRa, the light transmitted through region A1 located immediately above photodiode 4p in subject 2 is incident on photodiode 4p. At this point, a sub-image similar to sub-image Sa in FIG. 2C is obtained. When subject 2 is irradiated with illumination light in the irradiation direction indicated by arrow DRb, the light transmitted through region B1 adjacent to region A1 along the x-direction of FIG. 11A in subject 2 is incident on photodiode 4p. At this point, a sub-image similar to sub-image Sb in FIG. 3C is obtained. Accordingly, the high resolving power that is double in the x-direction of FIG. 11A is obtained using the two sub-images (see FIGS. 1A and 6).

Figure 11B:
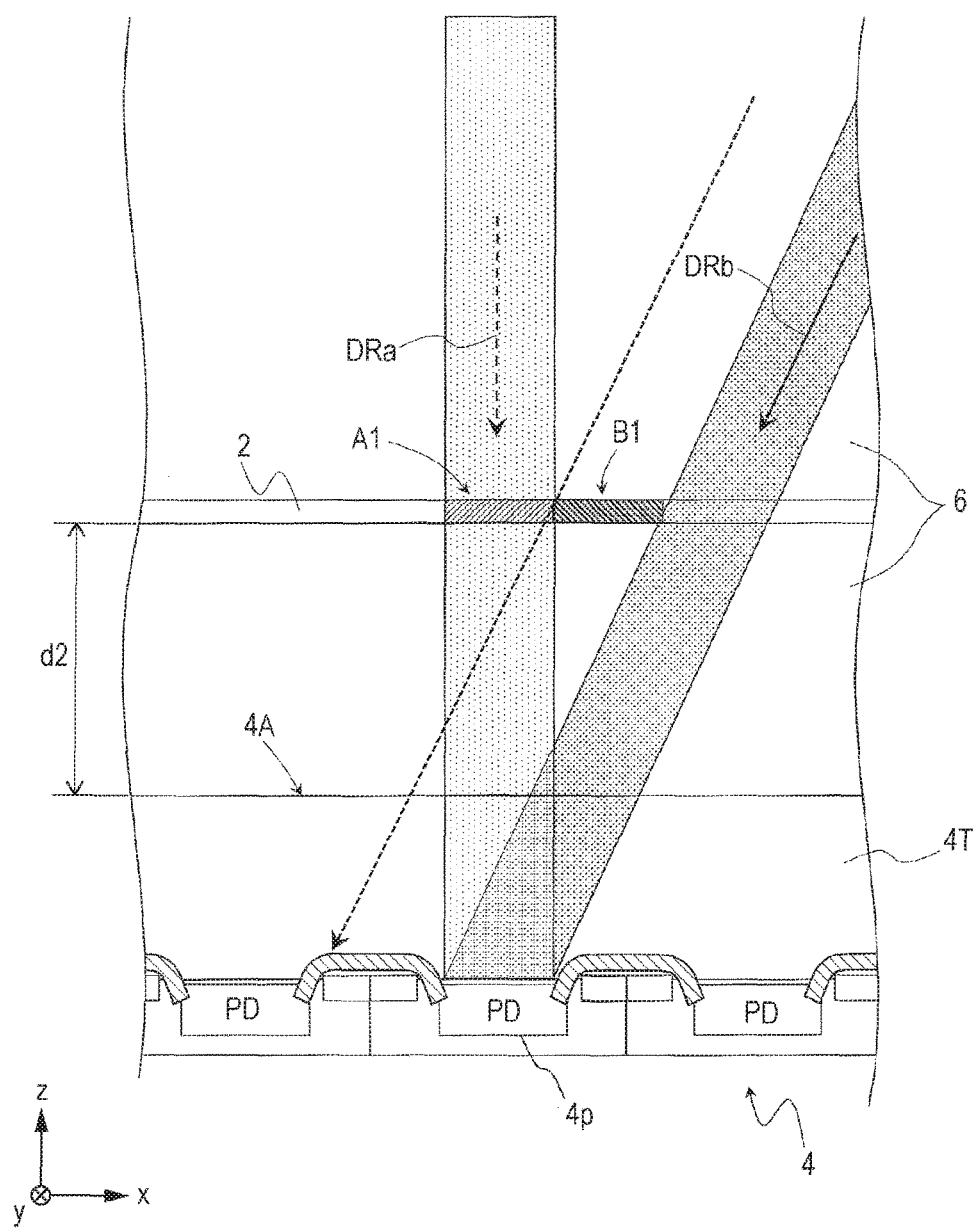
FIG. 11B is an enlarged sectional view schematically illustrating a relationship between illumination light transmitted through subject 2 and photodiode 4$p$ in a module in which subject 2 is disposed farther away from imaging surface 4A of image sensor 4.

FIG. 11B schematically illustrates a relationship between the illumination light transmitted through subject 2 and photodiode 4p in the module in which subject 2 is disposed farther away from imaging surface 4A of image sensor 4. In the example of FIG. 11B, gap d2 between imaging surface 4A and subject 2 is larger than gap d1 in FIG. 11A. Sometimes the gap between imaging surface 4A and subject 2 varies among the plurality of modules. The variation is attributed to insertion of encapsulant 6 (see FIG. 9) between imaging surface 4A and subject 2 during production of the module. According to the study of the inventor, the gap between imaging surface 4A and subject 2 can vary in a range of about 2 μm to about 8 μm.

In the example of FIG. 11B, when subject 2 is irradiated with illumination light in the irradiation direction indicated by arrow DRa, the light transmitted through region A1 in subject 2 is incident on photodiode 4p similarly to the example in FIG. 11A. At this point, a sub-image similar to sub-image Sa in FIG. 2C is obtained. On the other hand, when subject 2 is irradiated with illumination light in the irradiation direction indicated by arrow DRb, the light transmitted through the region different from region B1 in subject 2 is incident on photodiode 4p unlike the example in FIG. 11A. In FIG. 11B, the light transmitted through region B1 is not incident on any photodiodes 4p of image sensor 4. In other words, the sub-image having the information about region B1 in subject 2 can hardly be acquired even if subject 2 is irradiated with illumination light in the irradiation direction indicated by arrow DRb. In FIG. 11B, sometimes the sub-image used to form the high-resolution image is not obtained by the irradiation in the irradiation direction indicated by arrow DRb. Accordingly, the high-resolution image can hardly be formed.

Figure 11C:
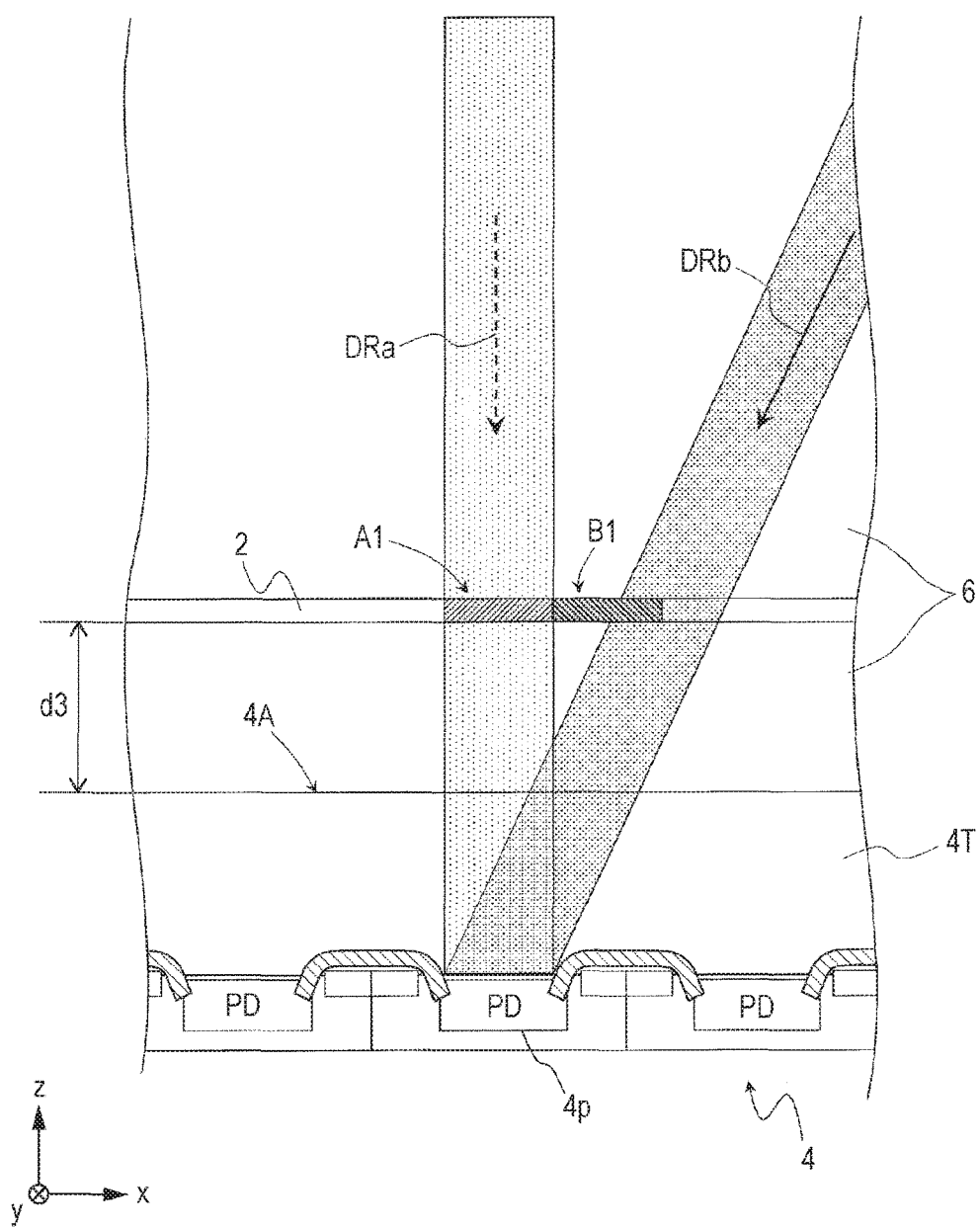
FIG. 11C is an enlarged sectional view schematically illustrating another example of the relationship between the disposition of subject 2 and the irradiation direction.

FIG. 11C schematically illustrates another example of the relationship between the disposition of subject 2 and the irradiation direction. In the example of FIG. 11C, gap d3 between imaging surface 4A and subject 2 is larger than gap d1 in FIG. 11A, and smaller than gap d2 in FIG. 11B. In FIG. 11C, when subject 2 is irradiated with illumination light in the irradiation direction indicated by arrow DRb, the light transmitted through a part of region B1 and the light transmitted through the region different from region B1 are incident on photodiode 4p. Part of the information about region B1 is missing in the obtained sub-image. Accordingly, the proper high-resolution image can hardly be formed using the sub-image obtained by the irradiation of subject 2 in the irradiation direction indicated by arrow DRa and the sub-image obtained by the irradiation of subject 2 in the irradiation direction indicated by arrow DRb.

As can be seen from FIGS. 11A to 11O, the plurality of irradiation directions set to a certain module are not always suitable for the irradiation directions used to acquire a plurality of sub-images in another module. That is, when the plurality of irradiation directions set to a certain module are used to acquire a plurality of sub-images in another module, sometimes the proper high-resolution image can hardly be formed from the plurality of sub-images acquired according to the plurality of irradiation directions. The similar phenomenon is possibly generated when a thickness of subject 2 varies among the plurality of modules.

As a result of the study, the inventor has found an image acquisition device (digitizer), an image forming system, and an image forming method for improving practicability of the technology of high resolving power exceeding the intrinsic resolving power of the image sensor.

An outline of the exemplary embodiment of the present disclosure will be described in advance of the detailed description of the exemplary embodiment. An image acquisition device according to one aspect of the present disclosure includes a lighting system and an irradiation direction decision section. In a module, a subject and an imaging element are integrally formed. The lighting system sequentially irradiates the subject with illumination light in a plurality of different irradiation directions based on the subject such that the illumination light transmitted through the subject is incident on the imaging element. The module is configured to acquire the plurality of images according to the plurality of different irradiation directions based on subject using the imaging element. Before the imaging element acquires the plurality of images according to the plurality of different irradiation directions, the irradiation direction decision section decides the plurality of different irradiation directions based on a difference between a first preliminary image and a second preliminary image. The first preliminary image is acquired with the imaging element when the subject is irradiated with first illumination light in a first irradiation direction. The second preliminary image is acquired with the imaging element when the subject is irradiated with second illumination light in a second irradiation direction.

According to one aspect, the irradiation direction decision section decides the plurality of different irradiation directions based on the first and second irradiation directions that are selected such that the difference between the first and second preliminary images is smaller than a predetermined level.

According to one aspect, the lighting system changes at least one of the first second irradiation directions. The imaging element acquires at least one first preliminary image and at least one second preliminary image according to the change in at least one of the first and second irradiation directions. The irradiation direction decision section decides an image set in which the difference between the first and second preliminary images is smaller than the predetermined level from at least one image set that includes the first and second preliminary images, and decides the plurality of different irradiation directions based on the first and second irradiation directions corresponding to the decided image set.

According to one aspect, the lighting system changes at least one of the first and second irradiation directions. The imaging element acquires at least one first preliminary image and at least one second preliminary image according to the change in at least one of the first and second irradiation directions. The irradiation direction decision section decides an image set in which the difference between the first and second preliminary images is minimized from a predetermined number of different image sets each of which includes the first and second preliminary images, and decides the plurality of different irradiation directions based on the first and second irradiation directions corresponding to the decided image set.

According to one aspect, the first and second irradiation directions have a symmetrical relationship with respect to the subject.

According to one aspect, the difference is an amount defined by a pixel luminance in the first preliminary image and a pixel luminance in the second preliminary image.

According to one aspect, the irradiation direction decision section calculates the difference between the first and second preliminary images by comparing luminances of a plurality of pixels constituting the first preliminary image and luminances of a plurality of pixels constituting the second preliminary image.

According to one aspect, the irradiation direction decision section calculates the difference between the first and second preliminary images after correcting the pixel luminance in at least one of the first and second preliminary images.

According to one aspect, the irradiation direction decision section acquires position information indicating a height of the subject relative to the imaging element, and decides the plurality of different irradiation directions according to the position information.

According to one aspect, the lighting system includes a stage on which the module is detachably loaded and a stage driving mechanism that can change an attitude of the stage.

An image forming system according to another aspect of the present disclosure includes: any one of the above image acquisition devices; and an image processing device that synthesizes the plurality of images acquired according to the plurality of different irradiation directions to form a high-resolution image of the subject, the high-resolution image having a resolving power higher than a resolving power of each of the plurality of images.

An image forming method according to another aspect of the present disclosure includes: acquiring a first preliminary image of a subject; acquiring a second preliminary image of the subject; deciding a plurality of different irradiation directions relative to the subject; acquiring a plurality of images according to the plurality of different irradiation directions; and forming a high-resolution image of the subject. In acquiring the first preliminary image, the first preliminary image is acquired by irradiating a module with first illumination light in a first irradiation direction, the subject and an imaging element being integrated with each other in the module such that illumination light transmitted through the subject is incident on the imaging element. In acquiring the second preliminary image, the second preliminary image is acquired by irradiating the module with second illumination light in a second irradiation direction. In deciding the plurality of different irradiation directions relative to the subject, the plurality of different irradiation directions are decided based on a difference between the first preliminary image and the second preliminary image. In acquiring the plurality of images according to the plurality of different irradiation directions, the plurality of images are acquired according to the plurality of different irradiation directions by sequentially irradiating the subject with the illumination light in the plurality of different irradiation directions. In forming the high-resolution image of the subject, the high-resolution image of the subject is formed by synthesizing the plurality of images, the high-resolution image having a resolving power higher than a resolving power of each of the plurality of images.

According to one aspect, acquiring the first preliminary image is performed a plurality of times while the first irradiation direction is changed.

According to one aspect, acquiring the second preliminary images is performed a plurality of times while the second irradiation direction is changed.

According to one aspect, the first and second irradiation directions have a symmetrical relationship with respect to the subject.

According to one aspect, in deciding the plurality of different irradiation directions, the plurality of different irradiation directions are decided based on the first and second irradiation directions in which the difference between the first and second preliminary images is smaller than a predetermined level.

According to one aspect, in deciding the plurality of different irradiation directions, the plurality of different irradiation directions are decided based on the first and second irradiation directions in which the difference between the first and second preliminary images is minimized.

According to one aspect, the difference is an amount defined by a pixel luminance in the first preliminary image and a pixel luminance in the second preliminary image.

According to one aspect, deciding the plurality of different irradiation directions includes comparing luminances of a plurality of pixels constituting the first preliminary image to luminances of a plurality of pixels constituting the second preliminary image.

The image forming method according to one aspect further includes correcting the pixel luminance in the second preliminary image between acquiring the second preliminary image and deciding the plurality of different irradiation directions.

Hereinafter, the exemplary embodiment of the present disclosure will be described in detail with reference to the drawings. The following exemplary embodiment illustrates a comprehensive or specific example. Numerical values, shapes, materials, components, dispositions and connection forms of the components, steps, and step sequences of the exemplary embodiment are only by way of example, but do not restrict the present disclosure. In the components of the exemplary embodiment, components that are not described in independent claim indicating the top concept are described as optional components.

(Image Acquisition Device)

Figure 12:
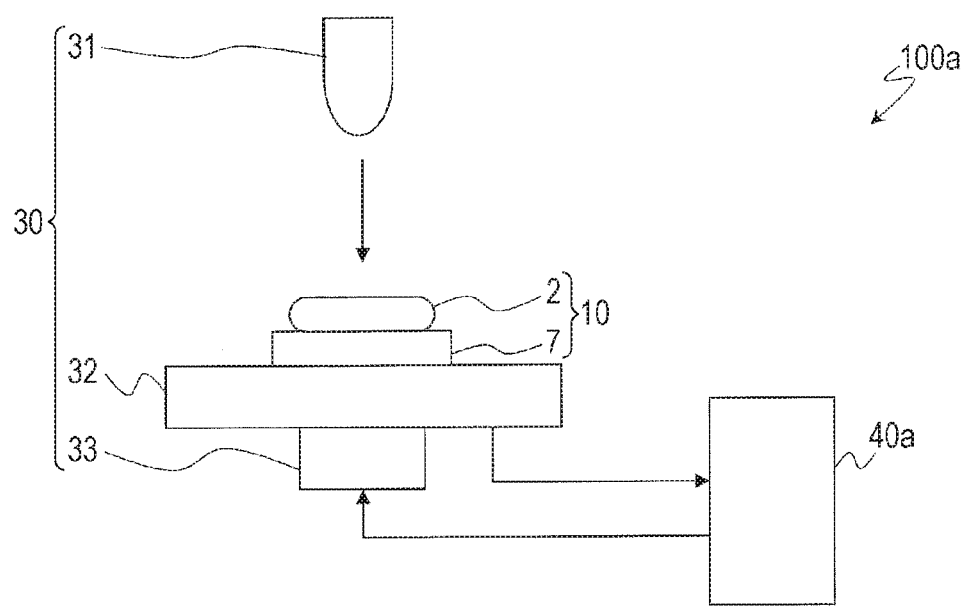
FIG. 12 is a schematic diagram illustrating an example of a configuration of an image acquisition device according to an exemplary embodiment of the present disclosure.

FIG. 12 illustrates an outline of a configuration example of an image acquisition device according to the exemplary embodiment of the present disclosure. Image acquisition device 100a in FIG. 12 includes lighting system 30. In the configuration of FIG. 12, lighting system 30 includes light source 31 that emits the illumination light, stage 32 on which module 10 is detachably loaded, and stage driving mechanism 33 that can change the attitude of stage 32. FIG. 12 schematically illustrates the state in which module 10 is loaded on stage 32. However, encapsulant 6 and transparent plate 8 of module 10 are not illustrated in FIG. 12. Module 10 is not necessarily a component for image acquisition device 100a.

Module 10 is disposed such that the illumination light transmitted through subject 2 is incident on imaging element 7 while module 10 is connected to stage 32. For example, lighting system 30 changes the irradiation direction based on subject 2 by changing the attitude of stage 32. In the exemplary embodiment, the change in attitude widely includes a change in tilt relative to a reference surface, a change in rotation angle relative to a reference direction, and a change in position relative to a reference point. Subject 2 is sequentially irradiated with the illumination light emitted from light source 31 in the plurality of different irradiation directions based on subject 2. The detailed configuration and operation example of lighting system 30 are described later. Subject 2 is irradiated with illumination light while the irradiation direction is changed, whereby imaging element 7 acquires the plurality of different images (sub-images) according to the plurality of different irradiation directions. The high-resolution image can be formed using the plurality of obtained images.

Image acquisition device 100a in FIG. 12 includes irradiation direction decision section 40a. Irradiation direction decision section 40a decides the plurality of different irradiation directions when imaging element 7 acquires the plurality of sub-images. In the exemplary embodiment, the sub-images are acquired in the plurality of different irradiation directions decided by the irradiation direction decision section. In other words, the sub-images are the plurality of different images corresponding to the plurality of different irradiation directions decided by the irradiation direction decision section. As described in detail later, at least one first preliminary image and at least one second preliminary image are acquired in advance of the acquisition of the plurality of sub-images. Based on the difference between the first and second preliminary images, irradiation direction decision section 40a decides the plurality of different irradiation directions used to acquire the plurality of sub-images. Specific examples of the configuration and operation of irradiation direction decision section 40a are described later.

An example of a method for changing the irradiation direction of the illumination light based on the subject will be described below with reference to FIGS. 13A to 14B.

Figure 13A:
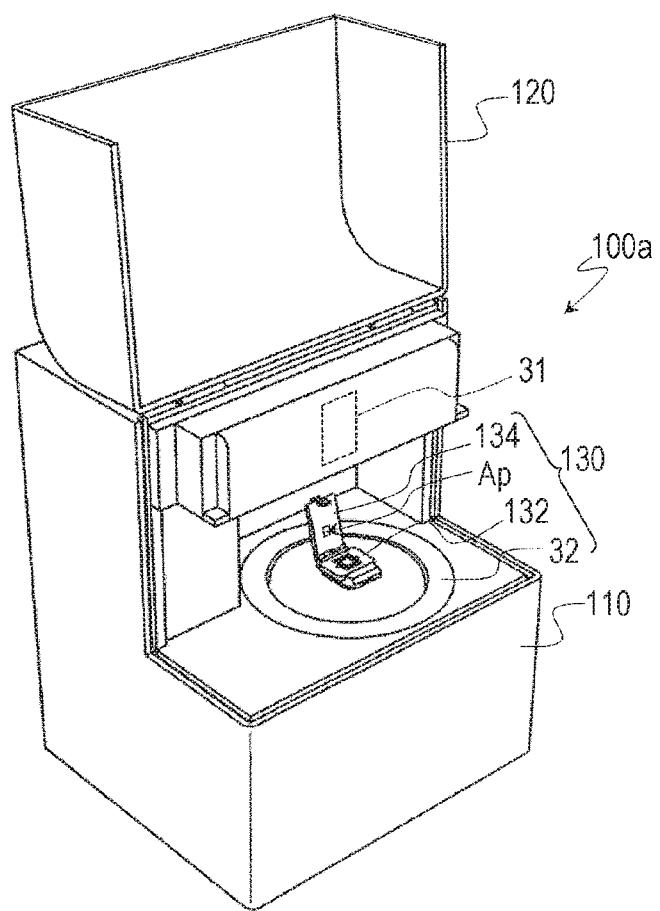
FIG. 13A is a perspective view illustrating an illustrative appearance of image acquisition device 100$a$.
Figure 13B:
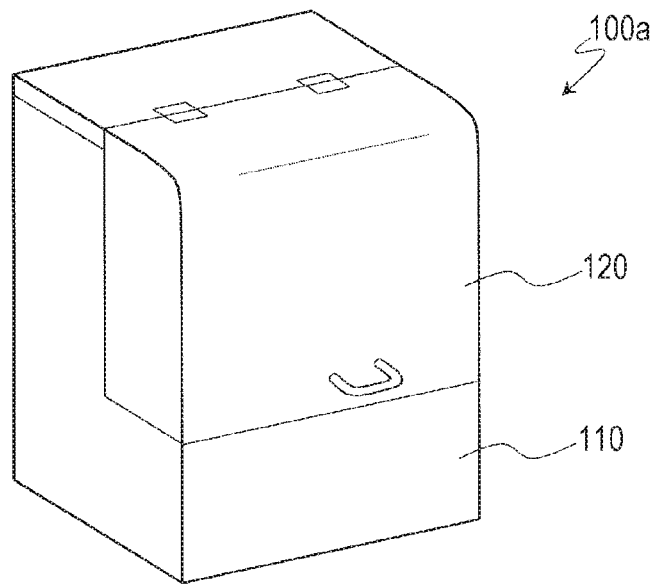
FIG. 13B is a perspective view illustrating a state in which lid 120 is closed in image acquisition device 100$a$ in FIG. 13A.

FIGS. 13A and 13B illustrate an illustrative appearance of image acquisition device 100a. In the configuration of FIG. 13A, image acquisition device 100a is provided with main body 110 including light source 31 and stage 32 and lid 120 that is openably coupled to main body 110. A dark room can be formed in image acquisition device 100a by closing lid 120 (see FIG. 13B).

In FIGS. 13A and 13B, socket 130 is connected onto stage 32 in order to hold module 10. Socket 130 may be fixed to stage 32, or detachably attached to stage 32. In this case, socket 130 is detachably attached to stage 32. For example, socket 130 includes lower base 132 to which module 10 is detachably attached and upper base 134 in which opening Ap is formed. In the configuration of FIG. 13A, socket 130 holds module 10 by sandwiching module 10 between lower base 132 and upper base 134.

Lower base 132 includes an electric connection section having an electric contact for the purpose of electric connection to imaging element 7 of module 10. Module 10 is placed on lower base 132 such that the imaging surface of imaging element 7 faces light source 31 during the acquisition of the subject image. At this point, the electric contact of the electric connection section comes into contact with rear surface electrode 5B (see FIGS. 8A and 8B) of imaging element 7, thereby providing the electric connection between imaging element 7 of module 10 and the electric connection section of lower base 132.

Figure 13C:
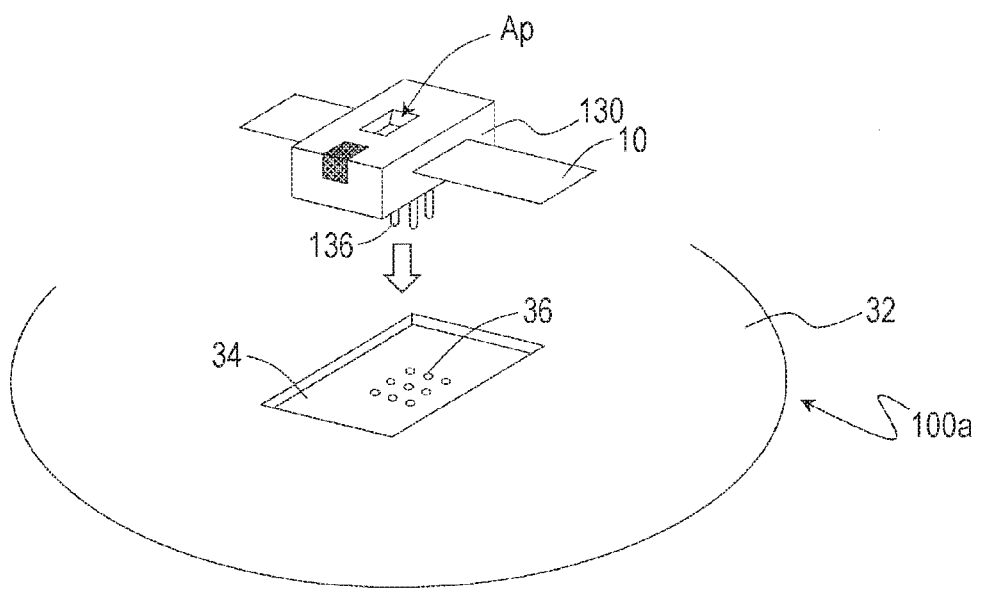
FIG. 13C is a view schematically illustrating an example of a method for fitting socket 130 into stage 32 of image acquisition device 100$a$.

FIG. 13C illustrates an example of a method for fitting socket 130 into stage 32 of image acquisition device 100a. In the configuration of FIG. 13C, socket 130 includes electrode 136 projecting from a bottom surface. Electrode 136 can constitute a part of the electric connection section of lower base 132. In the example of FIG. 13C, stage 32 of image acquisition device 100a includes attachment section 34 in which jack 36 is provided. As illustrated in FIG. 13C, socket 130 is fitted in stage 32 such that electrode 136 of socket 130 is inserted in jack 36 while socket 130 holds module 10. Therefore, the electric connection is established between image acquisition device 100a and imaging element 7 of module 10 held by socket 130. Stage 32 can include a circuit that receives output of image sensor 4 while socket 130 holding module 10 is fitted. In the exemplary embodiment, image acquisition device 100a acquires information (image signal or image data) indicating the image of subject 2 through the electric connection section of socket 130.

In the case that the plurality of subjects are imaged using the plurality of modules 10, sockets 130 as many as modules 10 are prepared, and the imaging object may be changed by exchanging sockets 130 holding modules 10. Alternatively, the imaging object may be changed by exchanging modules 10 with one socket 130 attached to stage 32.

As illustrated in FIG. 13C, the bottom surface of socket 130 and the top surface of attachment section 34 can be in close contact with each other by fitting socket 130 in stage 32. Therefore, the disposition of socket 130 is fixed to stage 32. Accordingly, the dispositions of stage 32 and module 10 held by socket 130 can be kept constant before and after the attitude of stage 32 is changed. Typically, a principal surface of transparent plate 8 of module 10 and stage 32 are substantially parallel to each other while socket 130 is fitted in stage 32.

Figure 14A:
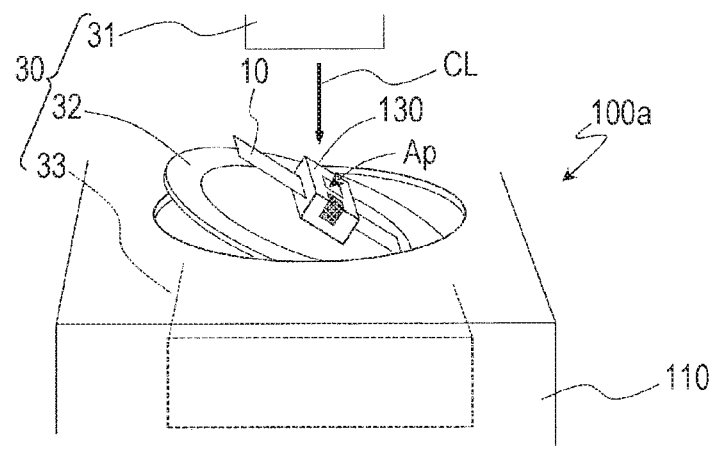
FIG. 14A is a view schematically illustrating an example of an irradiation direction changing method.

FIG. 14A illustrates an example of an irradiation direction changing method. As illustrated in FIG. 14A, module 10 held by socket 130 is irradiated with illumination light CL emitted from light source 31. Illumination light CL is incident on the subject of module 10 through opening Ap provided in socket 130. The light transmitted through the subject is incident on the imaging surface of imaging element 7 of module 10.

Typically, the light emitted from light source 31 is collimated light. However, in the case that the light incident on the subject is substantially parallel light, the light emitted from light source 31 does not need to be the collimated light.

For example, light source 31 includes an LED chip. Light source 31 may include a plurality of LED chips having peaks in different wavelength bands. For example, light source 31 may include an LED chip that emits blue light, an LED chip that emits red light, and an LED chip that emits green light. In the case that a plurality of light emitting elements are disposed in proximity to one another (for example, about 100 μm), the plurality of light emitting elements can be regarded as point light sources.

Using the plurality of light emitting elements that emit the light beams having colors different from one another, the subject is irradiated with the light having the different color in each irradiation direction in a time-division manner, which allows the plurality of sub-images to be acquired with respect to each color. For example, a blue sub-image set, a red sub-image set, and a green sub-image set may be acquired. A color high-resolution image can be formed using the acquired sub-image sets. For example, in the scene of the pathological diagnosis, many pieces of useful information about existence or non-existence of a lesion can be obtained using the color high-resolution image. A white LED chip may be used as light source 31 and a color filter may be disposed on an optical path to obtain the illumination light beams having different colors in the time division manner. An image sensor for color imaging may be used as image sensor 4. However, the configuration in which the color filter is not disposed is more advantageous from the viewpoint of suppressing reduction of the light amount incident on the photoelectric converter of image sensor 4.

Light source 31 is not limited to the LED, but an incandescent lamp, a laser element, a fiber laser, and a discharge tube may be used as light source 31. The light emitted from light source 31 is not limited to the visible light, but ultraviolet light and infrared light may be used. The number and disposition of the light emitting elements included in light source 31 can appropriately be set.

As illustrated in FIGS. 12 and 14A, image acquisition device 100a includes stage driving mechanism 33. Stage driving mechanism 33 includes a goniometer and a rotation mechanism, and changes a tilt of stage 32 relative to main body 110 and/or a rotation angle with respect to an axis passing through a center of stage 32. Stage driving mechanism 33 may include a slide mechanism that can translate stage 32 in a reference surface (typically, a horizontal plane).

Figure 14B:
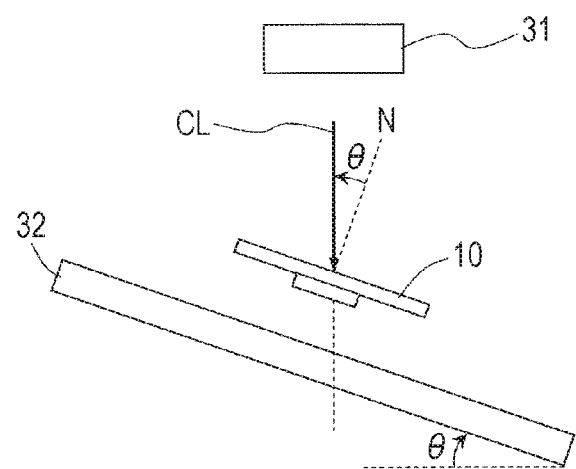
FIG. 14B is a view schematically illustrating a direction change of the beam incident on the subject when stage 32 is tilted by angle θ with respect to a reference surface.

The attitude of stage 32 can be changed by the operation of stage driving mechanism 33. In this case, because socket 130 holding module 10 is attached to stage 32, the attitude of module 10 can be changed by the change of the attitude of stage 32. For example, it is assumed that the incident direction of the illumination light is perpendicular to the imaging surface of the image sensor when stage 32 is not tilted relative to the reference surface. At this point, a relationship (for example, parallel) between the tilt of stage 32 relative to the reference surface and the tilt of module 10 relative to the reference surface (the tilt of module 10 can be also referred to as the tilt of transparent plate 8 relative to the reference surface) is kept constant before and after the attitude of stage 32 is changed. Therefore, as illustrated in FIG. 14B, when stage 32 is tilted by an angle θ relative to the reference surface, the direction of the beam incident on the subject is also tilted by the angle θ. In FIG. 14B, broken line N indicates a normal of the imaging surface of the image sensor.

Thus, the attitude of module 10 is changed together with stage 32, which allows the subject to be sequentially irradiated with the illumination light in the plurality of different irradiation directions based on subject 2. Accordingly, imaging element 7 of module 10 can acquire the plurality of images according to the plurality of different irradiation directions based on subject 2. For example, the irradiation direction based on subject 2 can be expressed by a set of an angle formed between normal N of the imaging surface of the image sensor and the beam incident on subject 2 (a zenith angle θ in FIG. 14B) and an angle formed between a reference direction set on the imaging surface and a projection of the incident beam onto the imaging surface (azimuth).

Subject 2 can be irradiated with illumination light in the plurality of different irradiation directions by moving light source 31 in image acquisition device 100a or by sequentially lighting a plurality of light sources disposed at different places. For example, the irradiation direction may be changed by moving light source 31 along a direction connecting light source 31 and subject 2. The irradiation direction may be changed by a combination of the change of the attitude of stage 32 and the movement of light source 31.

(Image Forming Method)

Figure 15:
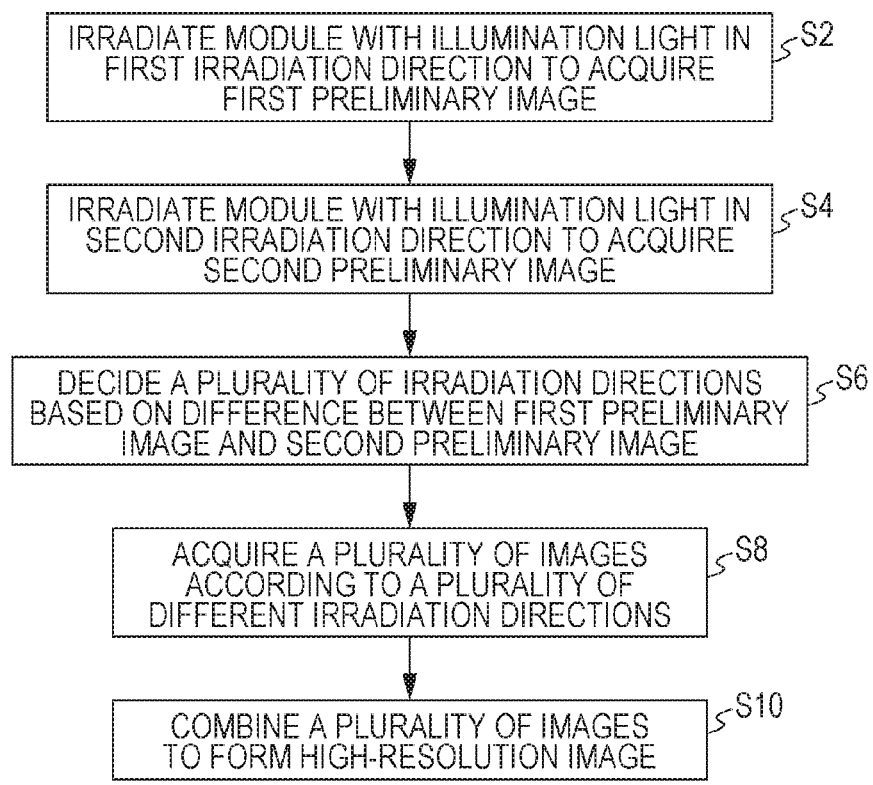
FIG. 15 is a view illustrating an outline of an illustrative image forming method according to an exemplary embodiment of the present disclosure.

FIG. 15 illustrates an outline of an illustrative image forming method according to the exemplary embodiment of the present disclosure. The image forming method in FIG. 15 roughly includes a process of acquiring the first preliminary image (process S2), a process of acquiring the second preliminary image (process S4), a process of deciding the plurality of irradiation directions based on the difference between the first and second preliminary images (process S6), a process of acquiring the plurality of images according to the plurality of irradiation directions (process S8), and a process of forming the high-resolution image by synthesizing the plurality of images (process S10).

Each of the first and second preliminary images is the subject image that is acquired by irradiating the module in which the subject and the imaging element are integrated with each other (for example, module 10 in FIGS. 8A and 8B) with the illumination light in the first and second irradiation directions. As described in detail later, the acquisition of the first preliminary image can be performed a plurality of times while the first irradiation direction is changed. The acquisition of the second preliminary image can also be performed a plurality of times while the second irradiation direction is changed. The first irradiation direction is not limited to a single direction, but can include a plurality of directions. Accordingly, the number of first preliminary images is not limited to one. Similarly the second irradiation direction is not limited to a single direction, but can include a plurality of directions. The number of second preliminary images is not limited to one. The sequence of the acquisition of the first preliminary image and the acquisition of the second preliminary image are not limited to the sequence in FIG. 15.

After the first and second preliminary images are acquired, a plurality of irradiation directions during the acquisition of the sub-images used to form the high-resolution image is decided based on a difference between the first and second preliminary images. At this point, the difference between the first and second preliminary images generally includes a value indicating a similarity between a certain first preliminary image and a certain second preliminary image constituting an image set, the similarity being calculated from the first and second preliminary images.

An image block including a plurality of pixels will be described in detail with respect to each of the first and second preliminary images constituting a certain image set. A sum of absolute differences of pixel luminances between the first and second preliminary images or a sum of squared differences of pixel luminances may be used as the difference between the first and second preliminary images. Alternatively, normalized cross-correlation and zero-means normalized cross-correlation, which are used in template matching, may be used as the difference between the first and second preliminary images.

As described in detail later, the plurality of irradiation directions decided based on the difference between the first and second preliminary images can be the irradiation direction according to a height of the subject relative to the imaging element. As used herein, the height of the subject relative to the imaging element means a distance between the imaging surface and a central portion in the thickness direction of the subject. In the exemplary embodiment, it is enough to decide a rough indication of the height of the subject relative to the imaging element based on the difference between the first and second preliminary images. It is not necessary to exactly obtain the distance between the imaging surface and a central portion in the thickness direction of the subject, and it is not necessary to decide the height of the subject relative to the imaging element with respect to portions of the subject in a plane parallel to the imaging surface of the imaging element. In acquiring the subject image, the disposition of the imaging element is not limited to the disposition in which the imaging surface is horizontal. Accordingly, the term "height" means a length measured along the direction normal to the imaging surface of the imaging element, but is not limited to a length along the vertical direction.

The plurality of sub-images are acquired after the plurality of irradiation directions are decided. Particularly, the plurality of images (sub-images) are acquired according to the plurality of irradiation directions by the sequential irradiation of the illumination light in the plurality of irradiation directions decided based on the difference between the first and second preliminary images.

After the plurality of images are acquired according to the plurality of irradiation directions, the high-resolution image having the resolving power higher than that of each of the plurality of images by synthesizing the plurality of images. The principle described with reference to FIGS. 1A to 6 can be applied to the formation of the high-resolution image. In the exemplary embodiment, the sub-images usable to form the high-resolution image can surely be acquired. It is not necessary to continuously perform the above processes.

(Principle Used to Decide a Plurality of Irradiation Directions)

The principle used to decide the plurality of irradiation directions will be described below with reference to FIGS. 16A to 17B. As described above with reference to FIG. 15, in the exemplary embodiment, preliminary imaging is performed in advance of the acquisition of the plurality of sub-images. At least one first preliminary image and at least one second preliminary image are acquired in the preliminary imaging. The first preliminary image is acquired with the imaging element when the subject is irradiated with the illumination light in the first irradiation direction. The second preliminary image is acquired with the imaging element when the subject is irradiated with the illumination light in the second irradiation direction. As described in detail below, in the preliminary imaging, the first and second irradiation directions are searched such that the light beams transmitted through the same region of subject 2 are incident on different photodiodes. The case that the double high resolving power is obtained in the x-direction of FIGS. 16A to 17B will be described below for convenience. The following principle can also be applied to the case that N times in high resolving power is obtained in the plane parallel to the imaging surface of the image sensor.

Figure 16A:
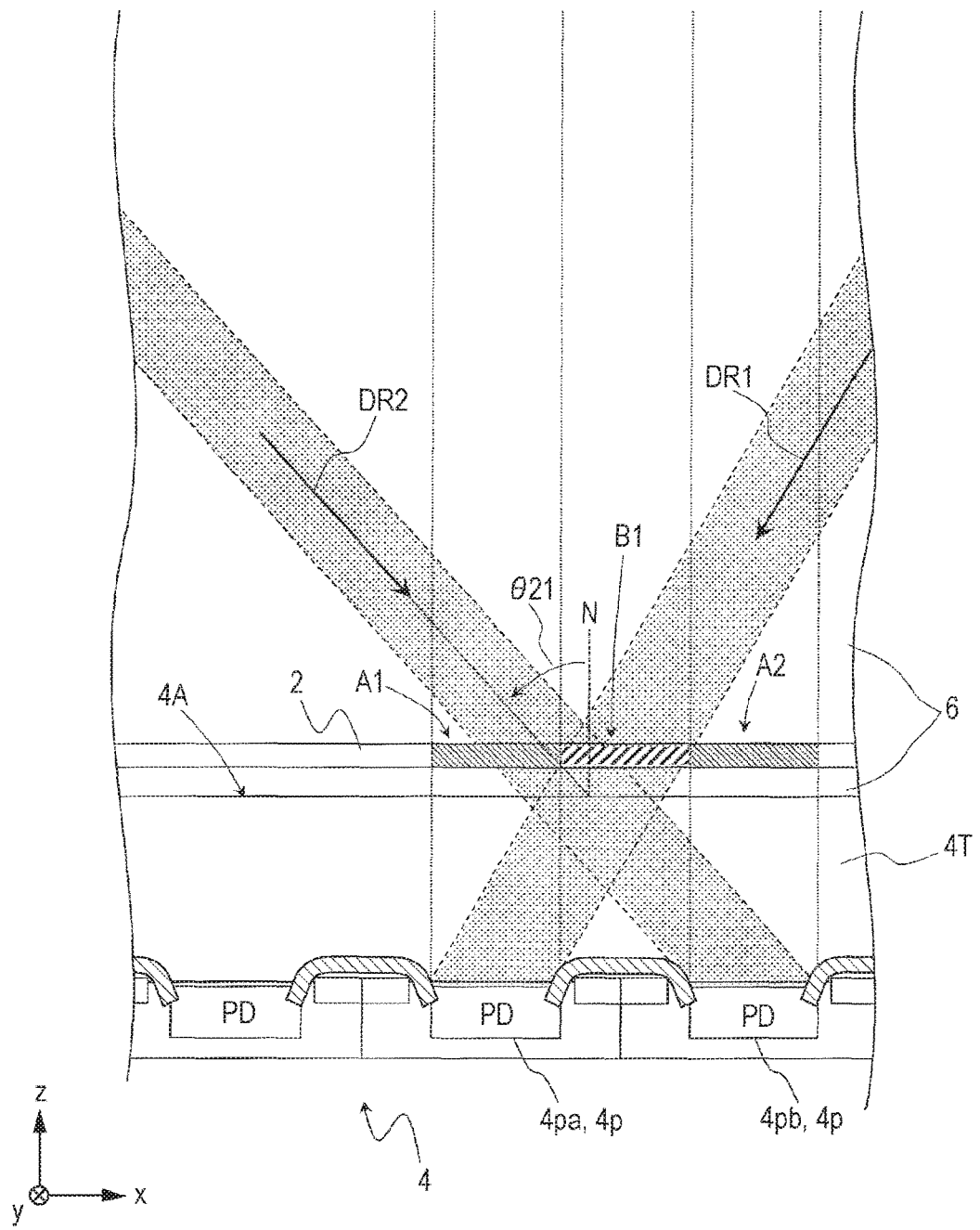
FIG. 16A is a sectional view schematically illustrating an example of a relationship between the irradiation direction of the illumination light and the region transmitting the illumination light in subject 2.

FIG. 16A schematically illustrates an example of a relationship between the irradiation direction of the illumination light and the region transmitting the illumination light in subject 2. Both the first irradiation direction indicated by solid-line arrow DR1 and the second irradiation direction indicated by solid-line arrow DR2 are illustrated in FIG. 16A. The example in FIG. 16A is illustrated only for convenience, but the irradiation in the first irradiation direction and the irradiation in the second irradiation direction are not simultaneously performed. In other drawings, sometimes the plurality of irradiation directions are illustrated in one drawing.

In the example of FIG. 16A, region A1 of subject 2 is located immediately above photodiode 4$pa$, and region A2 of subject 2 is located immediately above photodiode 4$pb$ adjacent to photodiode 4$pa$. At this point, region B1 located between region A1 and region A2 in subject 2 will be described in detail.

The light transmitted through region B1 of subject 2 is incident on photodiode 4$pa$ when subject 2 is irradiated with illumination light in first irradiation direction DR1. That is, in luminances (pixel values) of the plurality of pixels included in the first preliminary image acquired under the irradiation in first irradiation direction DR1, the luminance of the pixel corresponding to photodiode 4$pa$ indicates the amount of light transmitted through region B1 of subject 2. On the other hand, when subject 2 is irradiated with illumination light in second irradiation direction DR2, the light transmitted through a part of region A1 and the light transmitted through a part of region B1 are incident on photodiode 4*pb* adjacent to photodiode 4*pa*. Accordingly, at this point, in luminances of the plurality of pixels included in the second preliminary image acquired under the irradiation in second irradiation direction DR2, the luminance of the pixel corresponding to photodiode 4*pb* differs from the luminance of the pixel corresponding to photodiode 4*pa*.

Figure 16B:
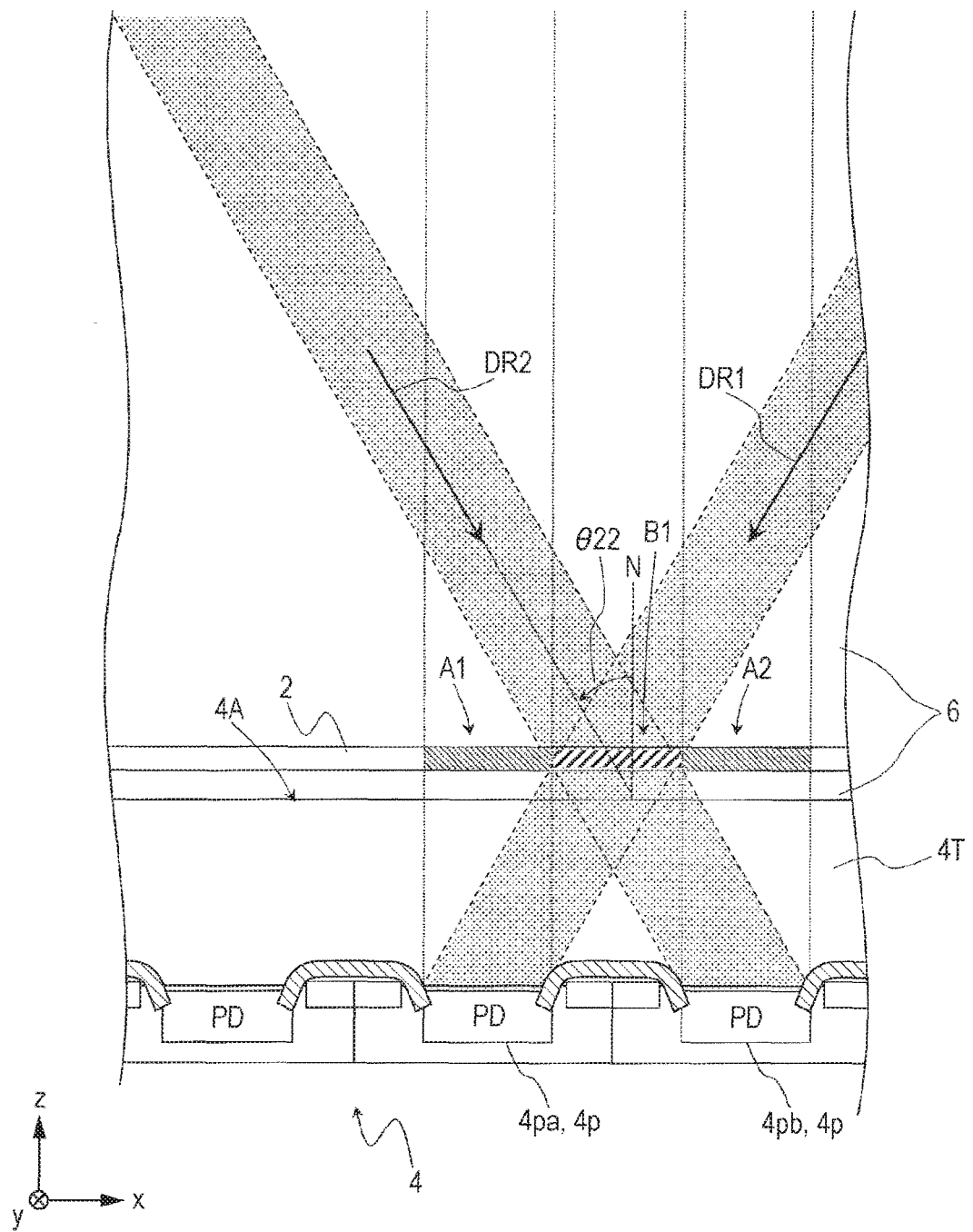
FIG. 16B is a sectional view schematically illustrating an example of a relationship between the irradiation direction of the illumination light and the region transmitting the illumination light in subject 2 when a second irradiation direction is changed from the state in FIG. 16A.

Then, the second irradiation direction is changed to acquire the second preliminary image again (see FIG. 16B). Irradiation angle θ22 in FIG. 16B is smaller than irradiation angle θ21 in FIG. 16A. The light transmitted through region B1 of subject 2 is incident on photodiode 4*pb* when subject 2 is irradiated with illumination light in second irradiation direction DR2 in FIG. 16B. The luminance of the pixel corresponding to photodiode 4*pb* in the luminances of the plurality of pixels included in the acquired second preliminary image is substantially equal to the luminance of the pixel corresponding to photodiode 4*pa* in the luminances of the plurality of pixels included in the first preliminary image. That is, when the light transmitted through a certain region of subject 2 under the irradiation in the first irradiation direction is incident on a certain photodiode (in this case, photodiode 4*pa*), and when the light transmitted through the region of subject 2 under the irradiation in the second irradiation direction is incident on a photodiode (in this case, photodiode 4*pb*) adjacent to the photodiode, the difference between the pixel values obtained with the photodiodes becomes the minimum.

Figure 16C:
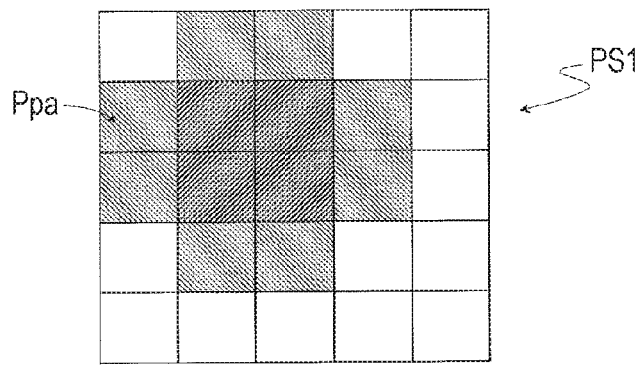
FIG. 16C is a view schematically illustrating first preliminary image PS1 acquired under the irradiation in first irradiation direction DR1 in FIG. 16B.
Figure 16D:
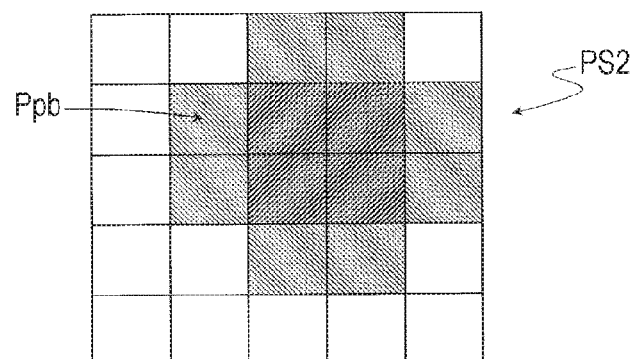
FIG. 16D is a view schematically illustrating second preliminary image PS2 acquired under the irradiation in second irradiation direction DR2 in FIG. 16B.

FIGS. 16C and 16D schematically illustrate first preliminary image PS1 acquired under the irradiation in first irradiation direction DR1 in FIG. 16B and second preliminary image PS2 acquired under the irradiation in second irradiation direction DR2 in FIG. 16B, respectively. Pixel Ppa in FIG. 16C and pixel Ppb in FIG. 16D correspond to photodiode 4*pa* and photodiode 4*pb*, respectively.

In the examples of FIGS. 16C and 16D, the luminance of pixel Ppa corresponding to photodiode 4*pa* is substantially equal to the luminance of pixel Ppb corresponding to photodiode 4*pb*. However, the positions of pixels Ppa and Ppb having the information about region B1 are shifted from each other by one pixel between first and second preliminary images PS1 and PS2. As can be seen from the example of FIGS. 16C and 16D, a luminance distribution of first preliminary image PS1 agrees substantially with a luminance distribution of the image in which second preliminary image PS2 is shifted by one pixel along a crosswise direction. As used herein, the luminance distribution means a spatial disposition of the pixel value indicating brightness of each pixel.

Figure 16E:
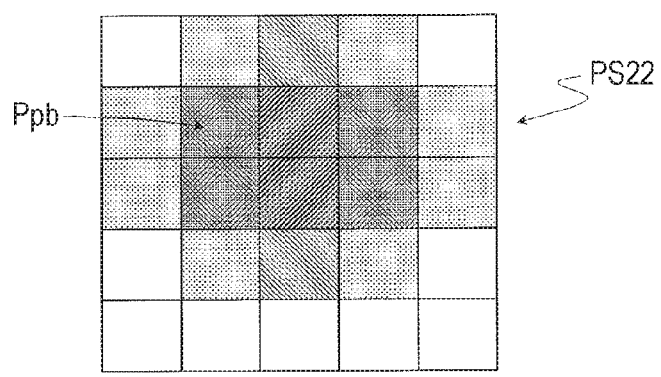
FIG. 16E is a view schematically illustrating second preliminary image PS22 acquired under the irradiation in second irradiation direction DR2 in FIG. 16A.

FIG. 16E schematically illustrates second preliminary image PS22 acquired under the irradiation in second irradiation direction DR2 in FIG. 16A. In FIG. 16E, pixel Ppb corresponds to photodiode 4*pb*. As can be seen from comparison between FIGS. 16E and 16C, in the case that both the light incident on photodiode 4*pa* under the irradiation in the first irradiation direction and the light incident on photodiode 4*pb* under the irradiation in the second irradiation direction are not the light transmitted through region B1 of subject 2, the luminance of pixel Ppa corresponding to photodiode 4*pa* is not equal to the luminance of pixel Ppb corresponding to photodiode 4*pb*.

Figure 17A:
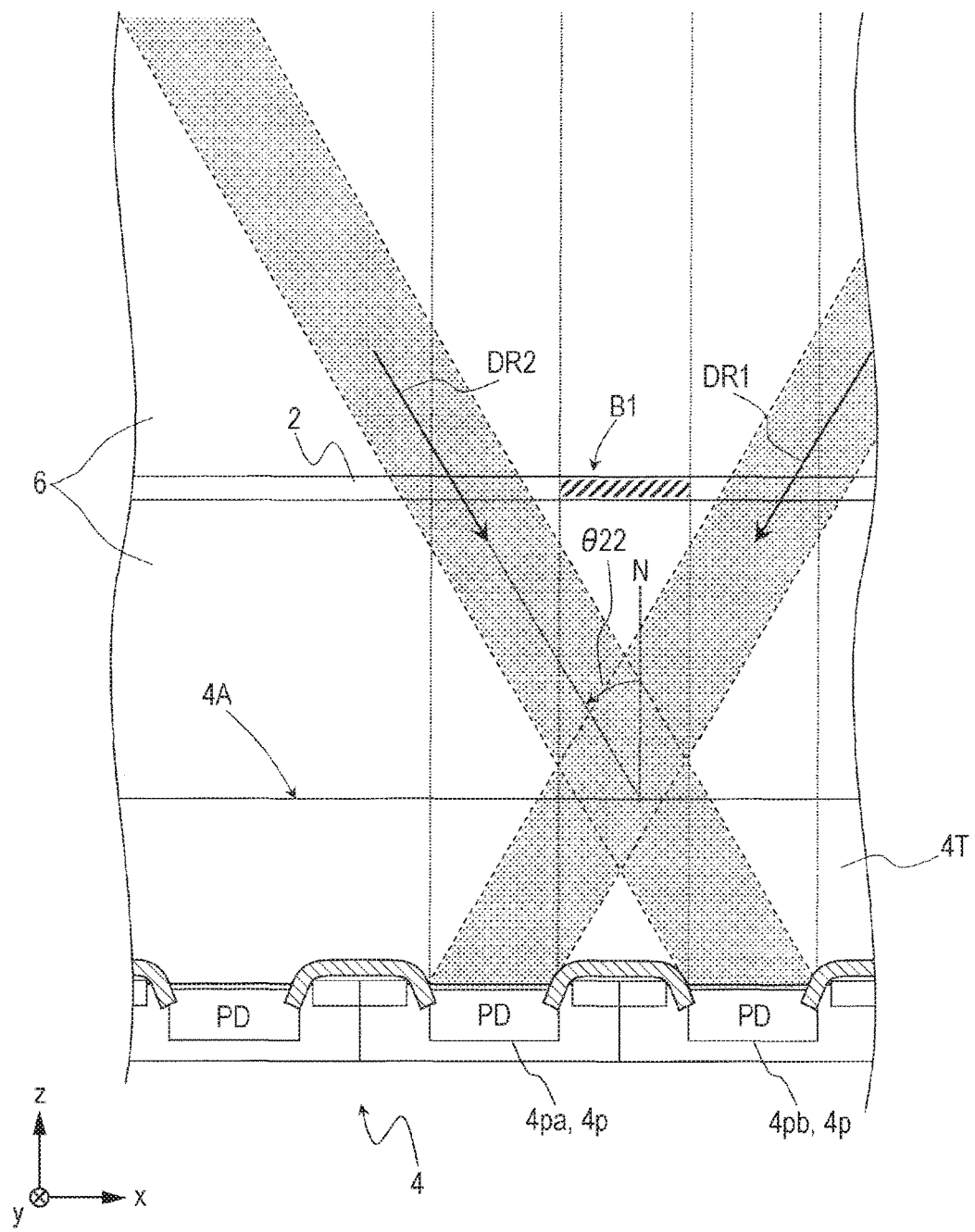
FIG. 17A is a sectional view schematically illustrating another example of a relationship between the irradiation direction of the illumination light and the region transmitting the illumination light in subject 2.

FIG. 17A schematically illustrates another example of the relationship between the irradiation direction of the illumination light and the region transmitting the illumination light in subject 2. FIG. 17A illustrates the case that subject 2 is irradiated with illumination light in first and second irradiation directions DR1 and DR2 in FIG. 16B using the module in which subject 2 is located far away from imaging surface 4A of image sensor 4 as compared to the examples in FIGS. 16A and 16B.

The light transmitted through a region different from region B1 of subject 2 is incident on photodiode 4*pa* when subject 2 is irradiated with illumination light in first irradiation direction DR1. The light which is transmitted through a region neither the region through which the illumination light in first irradiation direction DR1 passes in subject 2 nor region B1 of subject 2 is incident on photodiode 4*pb* adjacent to photodiode 4*pa* when subject 2 is irradiated with illumination light in second irradiation direction DR2. In the example of FIG. 17A, the luminance of pixel Ppa corresponding to photodiode 4*pa* is different from the luminance of pixel Ppb corresponding to photodiode 4*pb*. Thus, the combination of the first and second irradiation directions in which the difference between the pixel values obtained with two adjacent photodiodes is minimized can differ for each module.

Figure 17B:
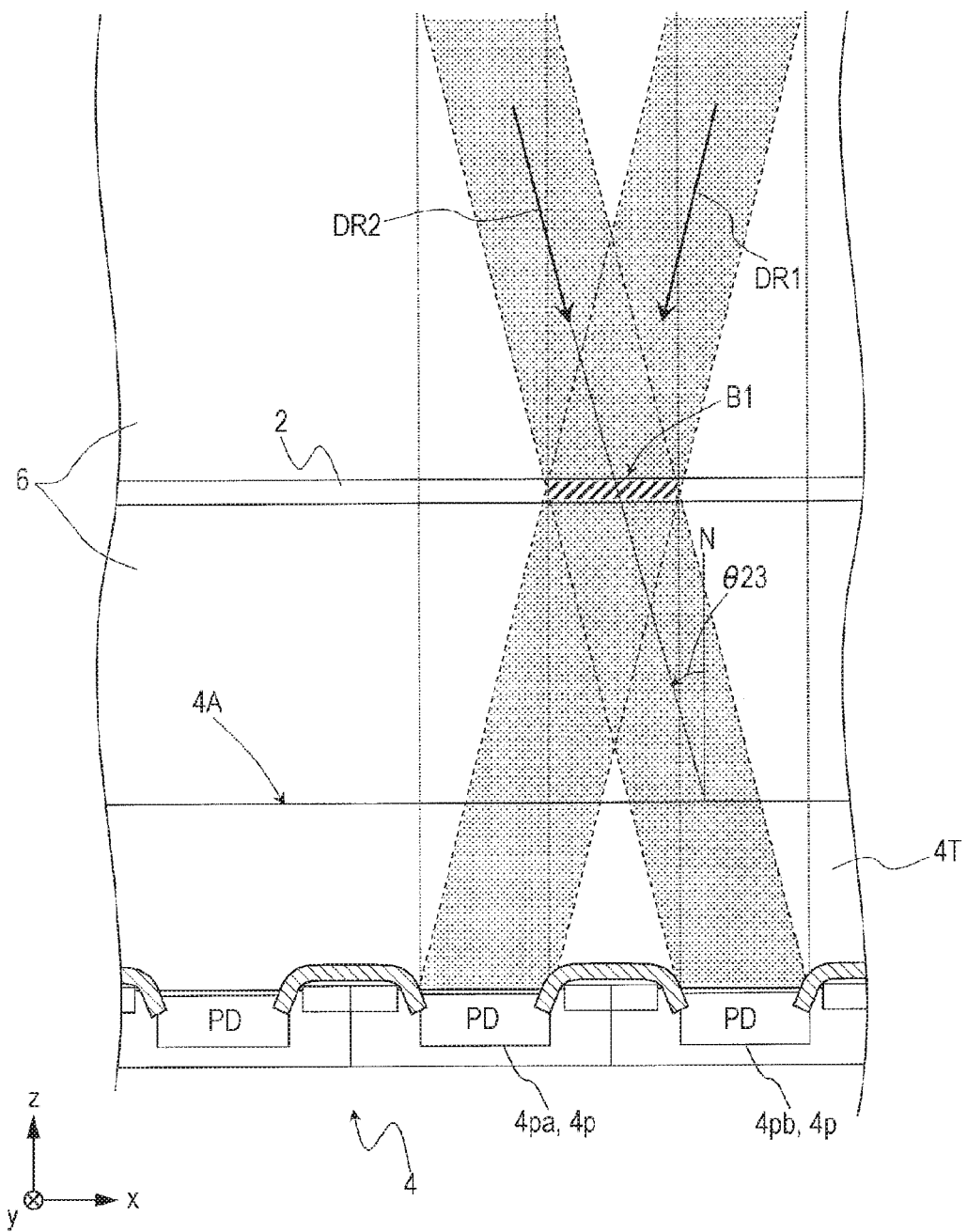
FIG. 17B is a view illustrating first and second irradiation directions DR1 and DR2 in which the beams transmitted through region B1 of subject 2 in FIG. 17A are incident on photodiodes 4$pa$ and 4$pb$, respectively.

FIG. 17B illustrates first and second irradiation directions DR1 and DR2 in which the beams transmitted through region B1 of subject 2 in FIG. 17A are incident on photodiodes 4*pa* and 4*pb*. At this point, irradiation angle θ23 in FIG. 17B is smaller than irradiation angle θ22 in FIG. 17A.

As illustrated in FIG. 17B, when the first irradiation direction and/or the second irradiation direction is properly adjusted, the illumination light in the first irradiation direction and the illumination light in the second irradiation direction can be incident on the same region (in this case, region B1) of subject 2. The light beans transmitted through the same region of subject 2 can be incident on the photodiodes adjacent to each other (in this case, photodiode 4*pa* and photodiode 4*pb*). At this point, the difference between the pixel values obtained with the two adjacent photodiodes is minimized. In other words, the first and second preliminary images are taken while the irradiation direction is changed, and the combination of the first and second irradiation directions is obtained such that the difference between the pixel values obtained with the adjacent photodiodes is minimized, whereby a relative disposition between the region through which the beam passes in subject 2 and the photodiode on which the transmitted beam is incident can roughly be recognized before the acquisition of the sub-image.

Thus, the comparison between the first and second preliminary images allows the relative disposition between the region through which the beam passes in subject 2 and the photodiode on which the transmitted beam is incident to be roughly recognized before the acquisition of the sub-image. For example, the plurality of irradiation directions suitable for the acquisition of the plurality of sub-images can geometrically be calculated when the relative disposition between the region through which the beam passes in subject 2 and the photodiode on which the transmitted beam is incident can be roughly recognized.

Thus, in the exemplary embodiment, the plurality of irradiation directions suitable for the acquisition of the plurality of sub-images can be decided before the acquisition of the sub-images. When the above technique is applied to each module, the plurality of irradiation directions suitable for the acquisition of the plurality of sub-images can be calculated for each module even if the height of the subject relative to the imaging element varies among the plurality of modules. Therefore, the high-resolution image can more surely be formed.

As can be seen from the comparison between FIGS. 16B and 17B, the combination of the first and second irradiation directions in which the difference between the pixel values obtained with the adjacent photodiodes is minimized can differ depending on the height of the subject relative to the imaging element. Therefore, position information indicating the gap between the imaging surface and the subject and position information indicating the height of the subject relative to the imaging element can also be obtained by finding the combination of the first and second irradiation directions in which the difference between the pixel values obtained with the adjacent photodiodes is minimized. The irradiation direction suitable for the height of the subject may be decided for each module using the pieces of position information. In deciding the plurality of irradiation directions used to acquire the plurality of sub-images, it is only necessary to obtain irradiation angle θ22 in FIG. 16B, but the position indicating the height of the subject relative to the imaging element is not necessarily calculated.

(Image Forming System)

Specific configuration examples of the image forming system and image acquisition device of the exemplary embodiment will be described below with reference to the drawings.

Figure 18:
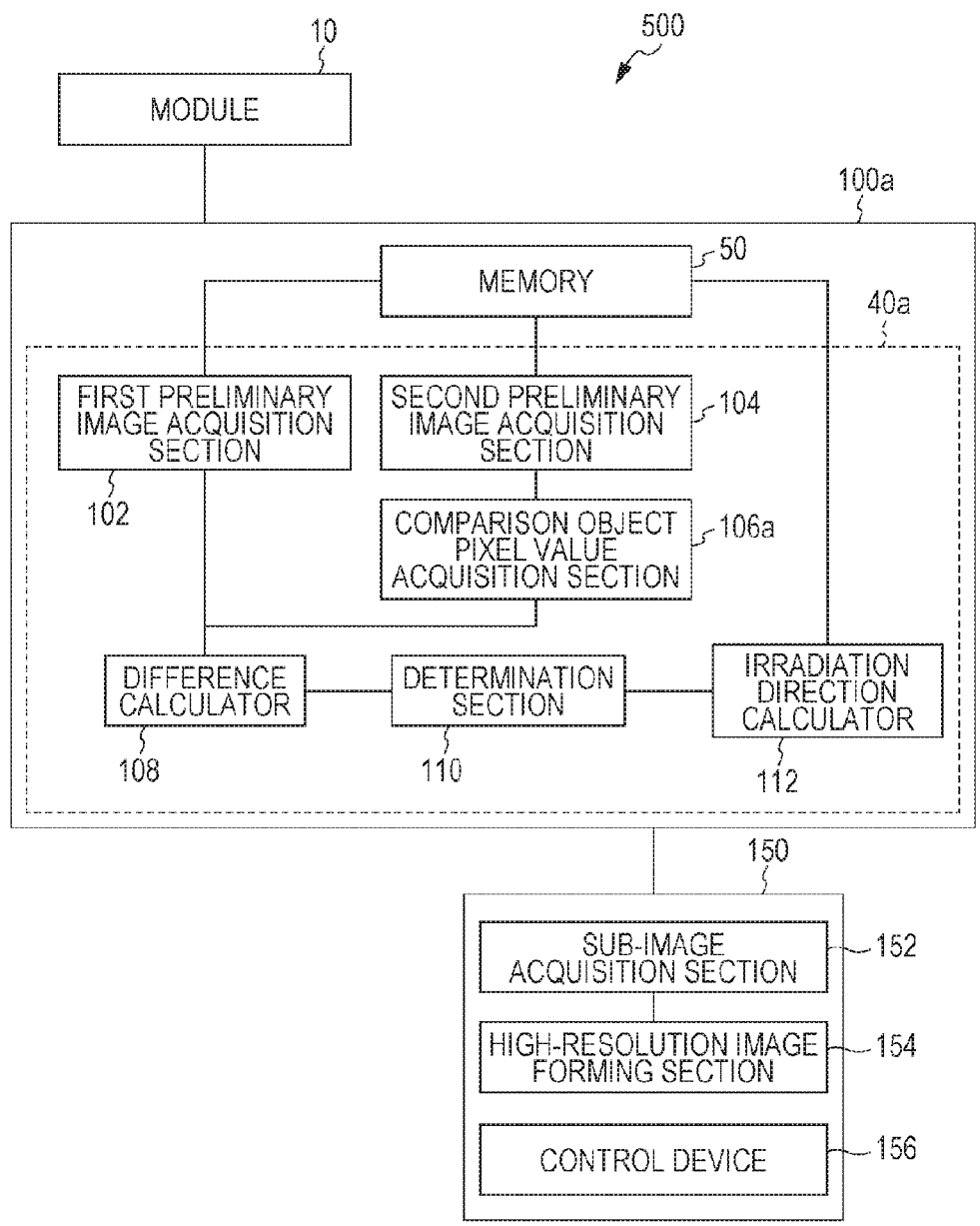
FIG. 18 is a block diagram illustrating an example of an image forming system according to an exemplary embodiment of the present disclosure.

FIG. 18 illustrates an example of the image forming system according to the exemplary embodiment of the present disclosure. Image forming system 500 in FIG. 18 includes image acquisition device 100a and image processing device 150. Lighting system 30 is not illustrated in FIG. 18.

Image processing device 150 can include a general-purpose or dedicated computer (or a general-purpose or dedicated processor). Image processing device 150 may be integrated with image acquisition device 100a, or separated from image acquisition device 100a. Image processing device 150 and image acquisition device 100a are not necessarily disposed at the same place. For example, image processing device 150 and image acquisition device 100a may be disposed at different places, and connected to each other through a network such as the Internet.

In the configuration of FIG. 18, image processing device 150 includes sub-image acquisition section 152 and high-resolution image forming section 154. In image forming system 500 of FIG. 18, data of the sub-image acquired with image acquisition device 100a is sent to image processing device 150. Sub-image acquisition section 152 of image processing device 150 acquires the data of the sub-image. High-resolution image forming section 154 of image processing device 150 synthesizes the plurality of sub-images using the principle described with reference to FIGS. 1A to 6, and forms the subject high-resolution image having the resolving power higher than that of each of the sub-images.

Image processing device 150 can act as a control device that supplies various commands in order to control the operation of each section of image acquisition device 100a. A configuration of image processing device 150 including control device 156 that supplies various commands in order to control the operation of each section of image acquisition device 100a will be described below by way of example.

Alternatively, image processing device 150 and control device 156 may be separated from each other. For example, image processing device 150 and control device 156 may be connected to each other through a network such as the Internet. Image processing device 150 disposed at a place different from a place of control device 156 may receive the data of the sub-image acquired with image acquisition device 150a, and form the high-resolution image.

(First Specific Example of Configuration and Operation of Irradiation Direction Decision Section)

In the configuration of FIG. 18, image acquisition device 100a includes irradiation direction decision section 40a and memory 50. A whole or part of irradiation direction decision section 40a can include a Digital Signal Processor (DSP), an application specific integrated circuit (ASIC), an Application Specific Standard Produce (ASSP), a Field Programmable Gate Array (FPGA), or a microcomputer. Referring to FIG. 18, irradiation direction decision section 40a includes first preliminary image acquisition section 102, second preliminary image acquisition section 104, comparison object pixel value calculator 106a, difference calculator 108, determination section 110, and irradiation direction calculator 112. Each of the sections may include an individual processor, or at least two sections may be included in one processor.

For example, memory 50 is a RAM. Memory 50 is not limited to the RAM, but a known storage device can be used as memory 50. A part of irradiation direction decision section 40a may include memory 50. For example, information indicating first irradiation direction DR1 and information indicating second irradiation direction DR2 (for example, see FIG. 16A) are stored in memory 50. TABLE 1 illustrates examples of the information indicating first irradiation direction DR1 and the information indicating second irradiation direction DR2.

TABLE 1

| ID | FIRST IRRADIATION ANGLE | SECOND IRRADIATION ANGLE |
| --- | --- | --- |
| 1 | −5° | 5° |
| 2 | −10° | 10° |
| 3 | −15° | 15° |
| 4 | −20° | 20° |
| 5 | −25° | 25° |
| 6 | −30° | 30° |
| 7 | −35° | 35° |

In this case, the first irradiation angle indicating first irradiation direction DR1 and the second irradiation angle indicating second irradiation direction DR2 are stored in memory 50. For example, the first and second irradiation angles in TABLE 1 correspond to the angle θ in FIG. 14B. In TABLE 1, ID indicated in a first column is an index that discriminates sets of the first and second irradiation angles from each other. The number of sets of the first and second irradiation angles and the values of the first and second irradiation angles can appropriately be set. In the list of TABLE 1, the first and second irradiation angles are set in units of 5° steps. In the same ID of the list in TABLE 1, the second irradiation angle is a value obtained by multiplying the first irradiation angle by −1.

Figure 19:
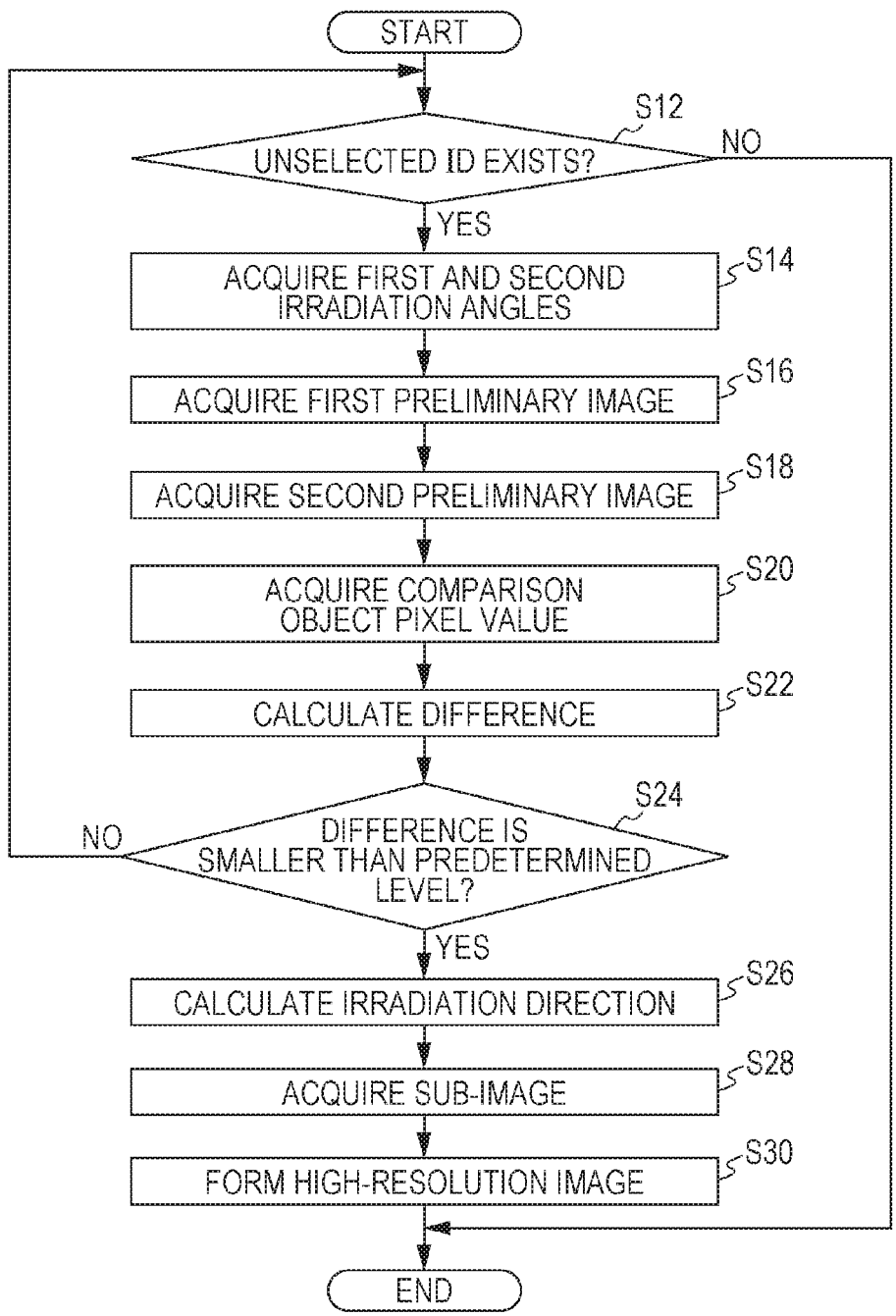
FIG. 19 is a flowchart illustrating an example of operation of image forming system 500.

FIG. 19 illustrates an example of operation of image forming system 500. In the example of FIG. 19, whether the first and second irradiation angles corresponding to the ID that is not selected yet exist in the list of the first and second irradiation angles stored in memory 50 is determined in step S12. At this point, because the first and second irradiation angles are not acquired yet, the processing goes to step S14. For example, first preliminary image acquisition section 102 or second preliminary image acquisition section 104 can determine whether the first and second irradiation angles corresponding to the ID that is not selected yet exist.

In step S14, first preliminary image acquisition section 102 and second preliminary image acquisition section 104 read the information indicating first irradiation direction DR1 and the information indicating second irradiation direction DR2 from memory 50, respectively. In this case, −5° is read as the first irradiation angle, and 5° is read as the second irradiation angle. As can be seen from TABLE 1, first irradiation direction DR1 and second irradiation direction DR2 have the symmetrical relationship with respect to the subject.

In step S16, the first preliminary image is acquired under the control of first preliminary image acquisition section 102. The first preliminary image is acquired at a first irradiation direction of −5° based on the subject. The subject is irradiated with the illumination light after stage driving mechanism 33 of lighting system 30 (for example, see FIG. 14A) changes the tilt of stage 32. The information indicating the acquired first preliminary image is temporarily stored in memory 50.

In step S18, the second preliminary image is acquired under the control of second preliminary image acquisition section 104. At this point, the tilt of stage 32 is changed such that the second irradiation direction based on the subject becomes 5°. Then, the imaging of the subject is performed. The information indicating the acquired second preliminary image is temporarily stored in memory 50.

In step S20, comparison object pixel value acquisition section 106a acquires a comparison object pixel value. The first and second irradiation directions are searched such that the light transmitted through the region between two regions in subject 2 located immediately above two photodiodes adjacent to each other are incident on the photodiodes. For this reason, in the case that the pixel luminance in the first preliminary image and the pixel luminance in the second preliminary image are compared to each other, the luminances of the pixels located at the same position in the first and second preliminary images are not compared to each other, but the luminance of the pixel located at a certain position and the luminance of the pixel shifted by one pixel from the position are compared to each other (see FIGS. 16C and 16D). An example in which the luminance of pixel Ppa corresponding to photodiode 4pa is compared to the luminance of pixel Ppb corresponding to photodiode 4pb will be described below. In this case, comparison object pixel value acquisition section 106a acquires the luminance of pixel Ppb corresponding to photodiode 4pb adjacent to photodiode 4pa.

In step S22, difference calculator 108 calculates a difference between the first preliminary image and the second preliminary image. For example, an absolute difference between the pixel luminance in the first preliminary image and the pixel luminance in the second preliminary image is calculated as the difference between the first and second preliminary images. For convenience, an example in which the absolute difference between the luminance of pixel Ppa corresponding to photodiode 4pa and the luminance of pixel Ppb corresponding to photodiode 4pb, which is acquired with comparison object pixel value acquisition section 106a, is calculated will be described below. Alternatively, at least two pixels may be selected from each of the first and second preliminary images to compare the pixel luminances to each other. For example, the absolute difference between the pixel luminances may be calculated for each set of a plurality of pixels each of which includes one pixel in the first preliminary image and one pixel in the second preliminary image, and an average value of the absolute differences may be used as the difference between the first and second preliminary images.

In step S24, determination section 110 determines whether the difference calculated in step S22 is greater than or equal to a predetermined level. When the difference between the first and second preliminary images is less than the predetermined level, the light transmitted through region B1 of subject 2 under the irradiation in the first irradiation direction can be determined to be incident on photodiode 4pa, and the light transmitted through region B1 of subject 2 under the irradiation in the second irradiation direction can be determined to be incident on photodiode 4pb. The relative disposition between the region through which the beam passes in subject 2 and the photodiode on which the transmitted beam is incident can roughly be recognized when the combination of the first and second irradiation directions is selected such that the difference between the first and second preliminary images is less than the predetermined level.

The level used in the determination can be set as appropriate. For example, the level used in the determination may be decided using the module in which the height of the subject relative to the imaging element is already known. The use of the module in which the height of the subject relative to the imaging element is already known can provide the difference between the first and second preliminary images when the light transmitted through region B1 of subject 2 under the irradiation in the first irradiation direction and the light transmitted through region B1 of subject 2 under the irradiation in the second irradiation direction are incident on the photodiodes adjacent to each other. The difference may be used as the level used in the determination.

When the difference between the first and second preliminary images is determined to be less than the predetermined level, the processing goes to step S26. On the other hand, when the difference between the first and second preliminary images is determined to be greater than or equal to the predetermined level, the processing returns to step S12.

When the processing returns to step S12, whether the first and second irradiation angles corresponding to the ID that is not selected yet exist in the list of the first and second irradiation angles stored in memory 50 is determined again. At this point, because the first and second irradiation angles that are of IDs 2 to 7 in TABLE 1 are not acquired yet, the processing goes to step S14. In step S14, the information indicating first irradiation direction DR1 and the information indicating second irradiation direction DR2 are read from memory 50. In this example, the first and second irradiation angles of ID 2 are read. After the first and second irradiation angles are acquired, the pieces of processing in steps S16 to S24 are performed again. In step S16, the first preliminary image is acquired with the irradiation direction based on the subject changed by lighting system 30 to −10°. In step S18, the second preliminary image is acquired with the irradiation direction based on the subject changed by lighting system 30 to 10°. When the difference between the newly-acquired first and second preliminary images is determined to be greater than or equal to the predetermined level in step S24, the processing returns to step S12, and the pieces of processing in steps S12 to S24 are repeated. When the first and second irradiation angles corresponding to the ID that is not selected yet do not exist in the first and second irradiation angles included in the list, the first and second irradiation angles are not acquired any more, but the processing is ended. In such cases, because the plurality of irradiation directions suitable for the acquisition of the sub-image cannot be decided, an error notification and display of information encouraging a user to update the list are performed for the user of image acquisition device 100a.

In step S26, based on the first and second irradiation directions in which the difference between the first and second preliminary images is less than the predetermined level, irradiation direction calculator 112 calculates the plurality of irradiation directions used to acquire the sub-image. The information indicating the calculated plurality of irradiation directions is stored in memory 50, and used in a later-described sub-image acquisition step. The plurality of irradiation directions can be calculated using the position information indicating the height of the subject relative to the imaging element and an array pitch between the photodiodes. Therefore, the plurality of irradiation directions are decided. The state in which the plurality of irradiation directions are decided means a state in which the plurality of irradiation directions can be specified by storing the pieces of information indicating the plurality of irradiation directions (for example, by storing the plurality of irradiation angles) in the memory. The plurality of irradiation directions used to acquire the sub-image is not limited to the irradiation directions selected from the first and second irradiation directions used to acquire the first and second preliminary images, but may be a direction different from the irradiation directions.

In step S28, the plurality of sub-images are acquired according to the plurality of irradiation directions calculated with irradiation direction calculator 112 (see FIGS. 2A to 5B). In step S30, the high-resolution image of the subject is formed using the plurality of acquired sub-images (see FIG. 6).

In the example of FIG. 19, the imaging element acquires at least one first preliminary image and at least one second preliminary image according to changes of the first and second irradiation directions. Therefore, at least one image set including the first and second preliminary images can be constructed. Irradiation direction decision section 40*a* decides the image set in which the difference between the first and second preliminary images is less than the predetermined level in the image sets. Irradiation direction decision section 40*a* decides the plurality of different irradiation directions based on the first and second irradiation directions corresponding to the image set.

In the exemplary embodiment, the plurality of irradiation directions suitable for the acquisition of the sub-images can be decided according to the individual module. The sub-images are acquired based on the proper irradiation directions according to the individual module, which allows the formation of the high-resolution image. Accordingly, in the exemplary embodiment, the practicability of the technology of high resolving power exceeding the intrinsic resolving power of the image sensor can be improved.

In the example of FIG. 19, the search of the first and second irradiation directions are terminated when the first and second irradiation directions in which the difference between the first and second preliminary images is less than the predetermined level is found. Alternatively, a plurality of sets of the first and second irradiation directions may be decided such that the difference between the first and second preliminary images is less than the predetermined level, and a plurality of different irradiation directions may be decided using the plurality of first and second irradiation directions.

(Second Specific Example of Configuration and Operation of Irradiation Direction Decision Section)

Figure 20:
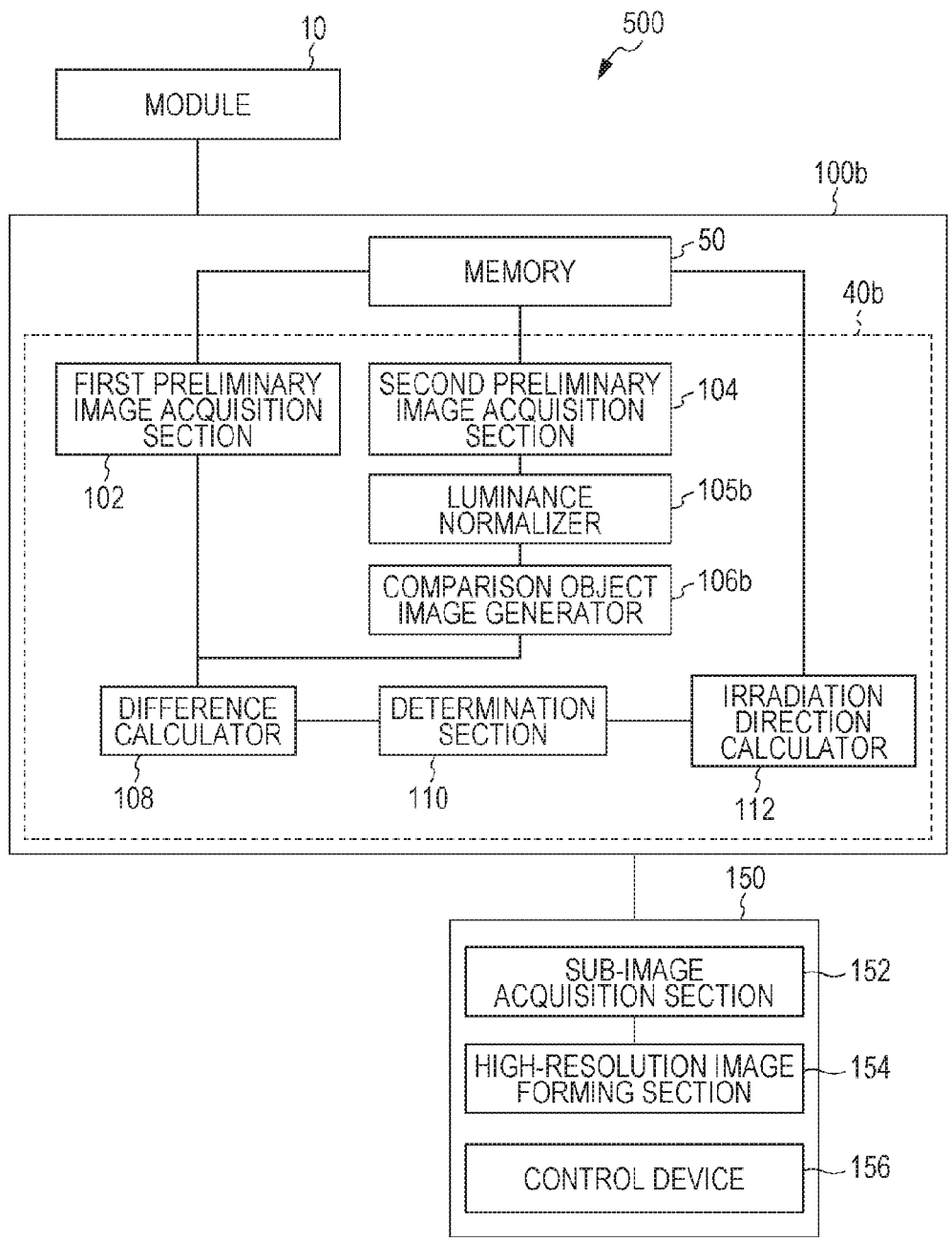
FIG. 20 is a block diagram illustrating another example of the image forming system according to the exemplary embodiment of the present disclosure.

FIG. 20 illustrates another example of the image forming system according to the exemplary embodiment of the present disclosure. Irradiation direction decision section 40*b* of image acquisition device 100*b* in FIG. 20 differs from irradiation direction decision section 40*a* (see FIG. 18) in that irradiation direction decision section 40*b* includes luminance normalizer 105*b* and comparison object image generator 106*b* instead of comparison object pixel value calculator 106*a*.

Figure 21:
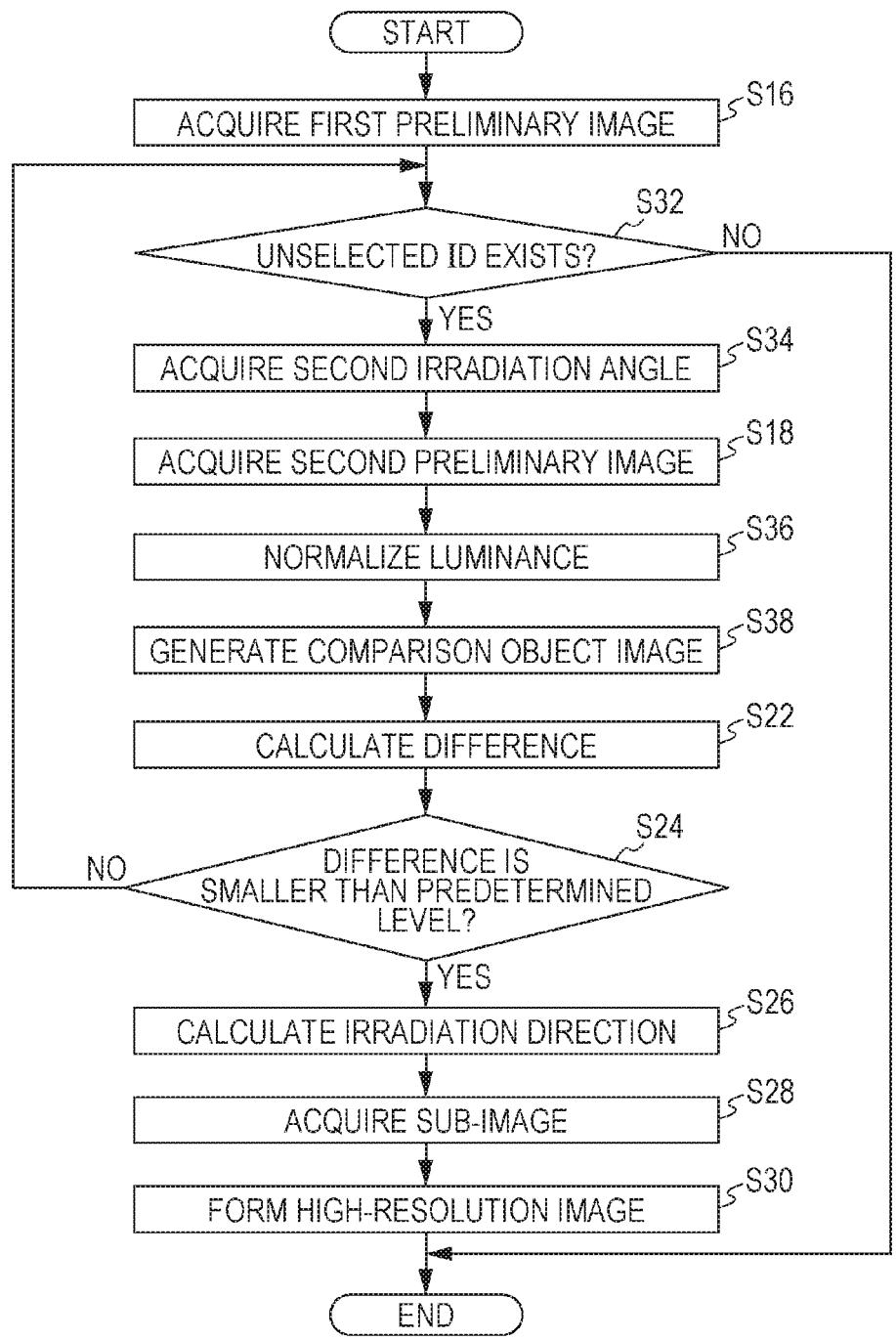
FIG. 21 is a flowchart illustrating another example of the operation of image forming system 500.

FIG. 21 illustrates another example of the operation of image forming system 500. In the following example, the luminance distribution of the first preliminary image and the luminance distribution of the second preliminary image are compared to each other. In other words, the luminances of the plurality of pixels constituting the first preliminary image and the luminances of the plurality of pixels constituting the second preliminary image are compared to each other to decide the plurality of different irradiation directions used to acquire the sub-images.

In the following example, the first preliminary image is acquired once. On the other hand, the acquisition of the second preliminary image is performed a plurality of times while the second irradiation direction is changed. Accordingly, the information indicating second irradiation direction DR2 is stored in memory 50. TABLE 2 illustrates an example of the information indicating second irradiation direction DR2.

TABLE 2

| ID | SECOND IRRADIATION ANGLE |
|---|---|
| 1 | 5° |
| 2 | 10° |
| 3 | 15° |
| 4 | 20° |
| 5 | 25° |
| 6 | 30° |
| 7 | 35° |

The first preliminary image is acquired in step S16. At this point, the first preliminary image is acquired while the irradiation direction based on the subject is 0°. The information indicating the acquired first preliminary image is temporarily stored in memory 50.

In step S32, whether the second irradiation angle corresponding to the ID that is not selected yet exists in the list of the second irradiation angles stored in memory 50 is determined. In this case, because the second irradiation angle is not acquired yet, the processing goes to step S34.

In step S34, second preliminary image acquisition section 104 reads the information indicating second irradiation direction DR2 from memory 50. At this point, 5° is read as the second irradiation angle.

The second preliminary image is acquired in step S18. At this point, the second preliminary image is acquired while the irradiation direction based on the subject is 5°. The information indicating the acquired second preliminary image is temporarily stored in memory 50.

In step S36, luminance normalizer 105*b* normalizes the luminance of the acquired second preliminary image. As used herein, the luminance normalization means processing of multiplying pixel luminances by a constant such that a sum of the luminances of the plurality of pixels included in an object image of the luminance normalization is equal to a sum of the luminances of the plurality of pixels included in a reference image.

In the example of FIG. 21, as can be seen from TABLE 2, first irradiation direction DR1 is parallel to the direction normal to the imaging surface of the imaging element while second irradiation direction DR2 is tilted relative to the direction normal to the imaging surface of the imaging element. That is, the irradiation in first irradiation direction DR1 is larger than the irradiation in second irradiation direction DR2 in a distance the light transmitted through the subject travels until reaching the imaging surface. For this reason, compared with the first preliminary image, sometimes the second preliminary image is dark as a whole due to an influence of absorption or scattering in the module. If the first and second preliminary images greatly differ in luminance as a whole, there is a risk of incorrectly evaluating the difference between the first and second preliminary images.

The luminance of the second preliminary image is normalized in the example of FIG. 21. Therefore, each pixel luminance can properly be corrected in the second preliminary image. Accordingly, the difference between the first and second preliminary images can more correctly be evaluated.

In step S38, comparison object image generator 106b generates an image (hereinafter, sometimes simply referred to as a "shifted image") in which the second preliminary image is shifted by a predetermined number of pixels. In this example, the image in which the post-luminance-normalization second preliminary image is shifted by one pixel is generated.

Figure 22:
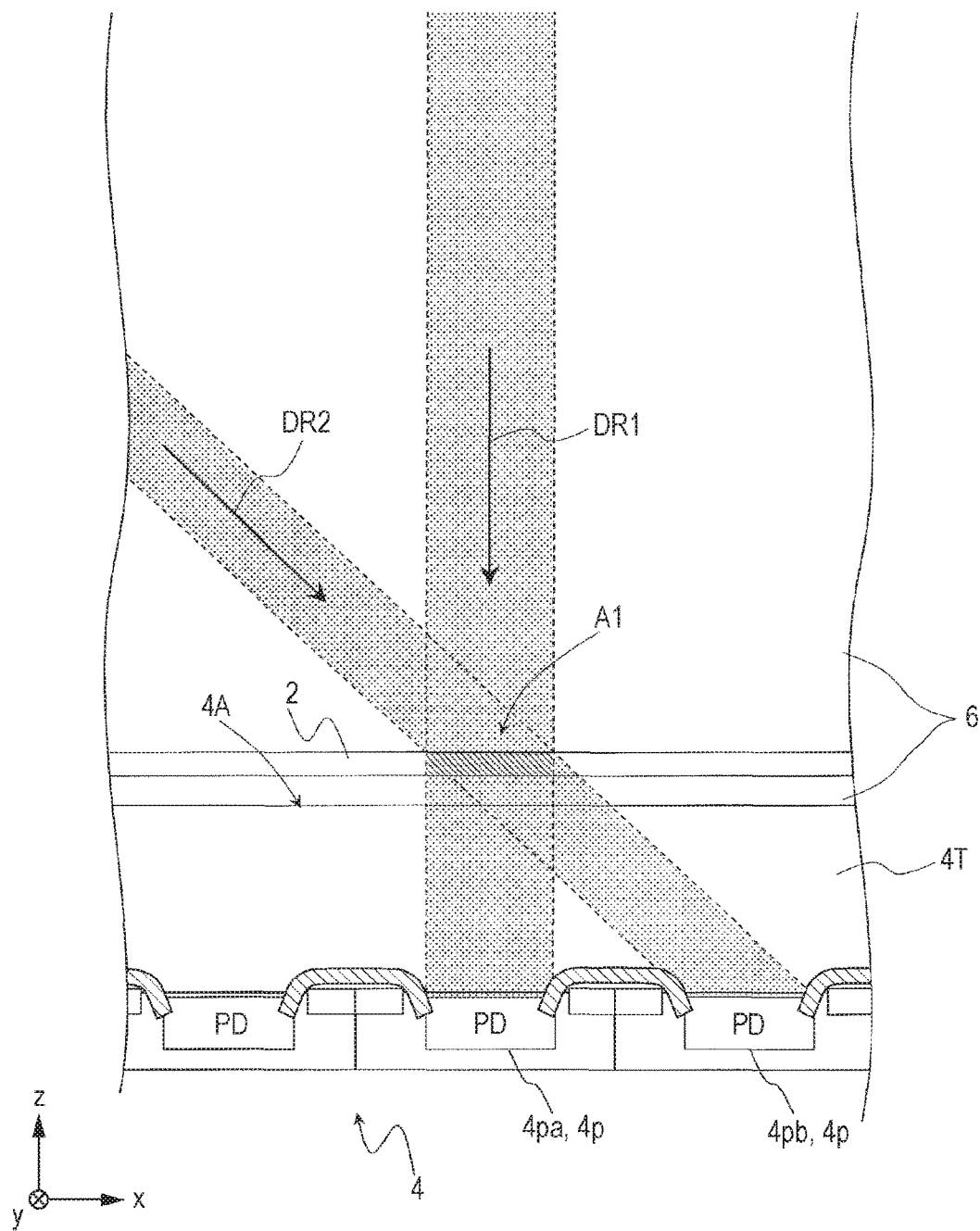
FIG. 22 is a view schematically illustrating examples of first and second irradiation directions DR1 and DR2 in a second specific example.

FIG. 22 schematically illustrates examples of first and second irradiation directions DR1 and DR2 in a second specific example. In the example of FIG. 22, when subject 2 is irradiated with illumination light in first irradiation direction DR1, the light transmitted through region A1 immediately above photodiode 4pa in subject 2 is incident on photodiode 4pa. When subject 2 is irradiated with illumination light in second irradiation direction DR2, the light transmitted through region A1 in subject 2 is incident on photodiode 4pb adjacent to photodiode 4pa. Accordingly, the first preliminary image similar to first preliminary image PS1 in FIG. 16C and the second preliminary image similar to second preliminary image PS2 in FIG. 16D are obtained under the irradiation of first and second irradiation directions DR1 and DR2 in FIG. 22. On the other hand, the second preliminary image similar to second preliminary image PS22 in FIG. 16E is obtained in such second irradiation direction DR2 that the light transmitted through the region except for region A1 in subject 2 is incident on photodiode 4pb.

Figure 23A:
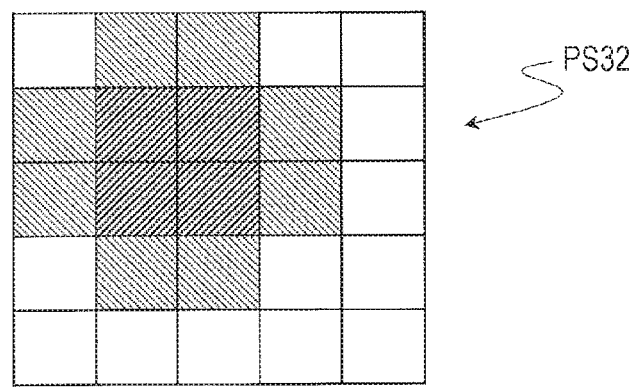
FIG. 23A is a view schematically illustrating shifted image PS32 that is generated from a second preliminary image acquired under the irradiation in second irradiation direction DR2 in FIG. 22.
Figure 23B:
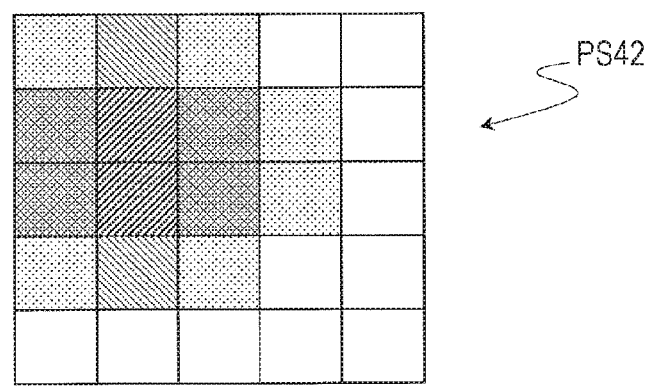
FIG. 23B is a view schematically illustrating shifted image PS42 that is generated from a second preliminary image acquired under the irradiation in an irradiation direction different from second irradiation direction DR2 in FIG. 22.

FIG. 23A schematically illustrates shifted image PS32 that is generated from the second preliminary image acquired under the irradiation in second irradiation direction DR2 in FIG. 22. FIG. 23B is a view schematically illustrating shifted image PS42 that is generated from a second preliminary image acquired under the irradiation in an irradiation direction different from second irradiation direction DR2 in FIG. 22. As can be seen from comparison between FIGS. 23A and 16C, when the light transmitted through a certain region of subject 2 under the irradiation in the first irradiation direction is incident on a certain photodiode, and when the light transmitted through the region of subject 2 under the irradiation in the second irradiation direction is incident on a photodiode adjacent to the photodiode, the luminance distribution of the first preliminary image agrees substantially with the luminance distribution of the shifted image generated from the second preliminary image. On the other hand, the luminance distribution of the shifted image, which is generated from the second preliminary image acquired under the irradiation in other second irradiation directions, is different from the luminance distribution of the first preliminary image as can be seen from comparison between FIGS. 23B and 16C. Accordingly, when the light transmitted through a certain region of subject 2 under the irradiation in the first irradiation direction is incident on a certain photodiode, and when the light transmitted through the region of subject 2 under the irradiation in the second irradiation direction is incident on a photodiode adjacent to the photodiode, the difference between the first and second preliminary images is minimized. Accordingly, similarly to the example described with reference to FIGS. 16A to 17B, the combination of the first and second irradiation directions is obtained such that the difference between the first and second preliminary images is minimized, whereby the relative disposition between the region through which the beam passes in subject 2 and the photodiode on which the transmitted beam is incident can roughly be recognized before the acquisition of the sub-image.

The difference between the first and second preliminary images is calculated in step S22 (FIG. 21). For example, the absolute difference between the pixel luminance in the first preliminary image and the pixel luminance in the shifted image generated from the second preliminary image is calculated with respect to each pixel, and the sum of the absolute differences is set to the difference between the first and second preliminary images. Alternatively, a square of the difference between the pixel luminance in the first preliminary image and the pixel luminance in the shifted image generated from the second preliminary image may be calculated with respect to each pixel, and a variance obtained by adding the squares may be set to the difference between the first and second preliminary images.

In step S24, whether the difference calculated in step S22 is greater than or equal to the predetermined level is determined. When the difference between the first and second preliminary images is less than the predetermined level, as illustrated in FIGS. 22 to 23B, the light transmitted through a certain region of subject 2 under the irradiation in the first irradiation direction can be determined to be incident on a certain photodiode, and the light transmitted through the region of subject 2 under the irradiation in the second irradiation direction can be determined to be incident on a photodiode adjacent to the photodiode. Accordingly, the relative disposition between the region through which the beam passes in subject 2 and the photodiode on which the transmitted beam is incident can roughly be recognized from the combination of the first and second irradiation directions. Thus, the image in which one of the first and second preliminary images is shifted by a predetermined number of pixels may be generated, and the first and second preliminary images may be compared to each other by comparing the image to the other of the first and second preliminary images.

When the difference between the first and second preliminary images is determined to be less than the predetermined level, the processing goes to step S26. Because the following pieces of processing are similar to those in FIG. 19, the description is omitted. On the other hand, when the difference between the first and second preliminary images is determined to be greater than or equal to the predetermined level, the processing returns to step S32. Then the pieces of processing in steps S34 to S24 are repeated until the combination of the first and second irradiation directions is found such that the difference between the first and second preliminary images is less than the predetermined level. The processing is ended in the case that the combination of the first and second irradiation directions such that the difference between the first and second preliminary images is less than the predetermined level is not found even if all the second irradiation angles included in the list of TABLE 2 are evaluated.

In the second specific example, the first preliminary image is acquired once, and one first preliminary image is compared to the second preliminary images acquired according to the plurality of second irradiation directions. Accordingly, a processing time necessary for the decision of the plurality of irradiation directions can be shortened compared with the case that the imaging is performed the plurality of times on both the first and second irradiation directions. The first preliminary image may be acquired after the plurality of second preliminary images are acquired.

In the second specific example, the difference between the first and second preliminary images is calculated after the luminance of the second preliminary image is normalized. Therefore, the difference between the first and second preliminary images can more correctly be evaluated. The luminance normalization object can be set as appropriate according to the settings of the first and second irradiation directions. The luminance normalization may be performed on one of or both the first and second preliminary images. The luminance normalization may be performed between the acquisition of the luminance normalization object and the decision of the plurality of different irradiation directions.

(Third Specific Example of Configuration and Operation of Irradiation Direction Decision Section)

Figure 24:
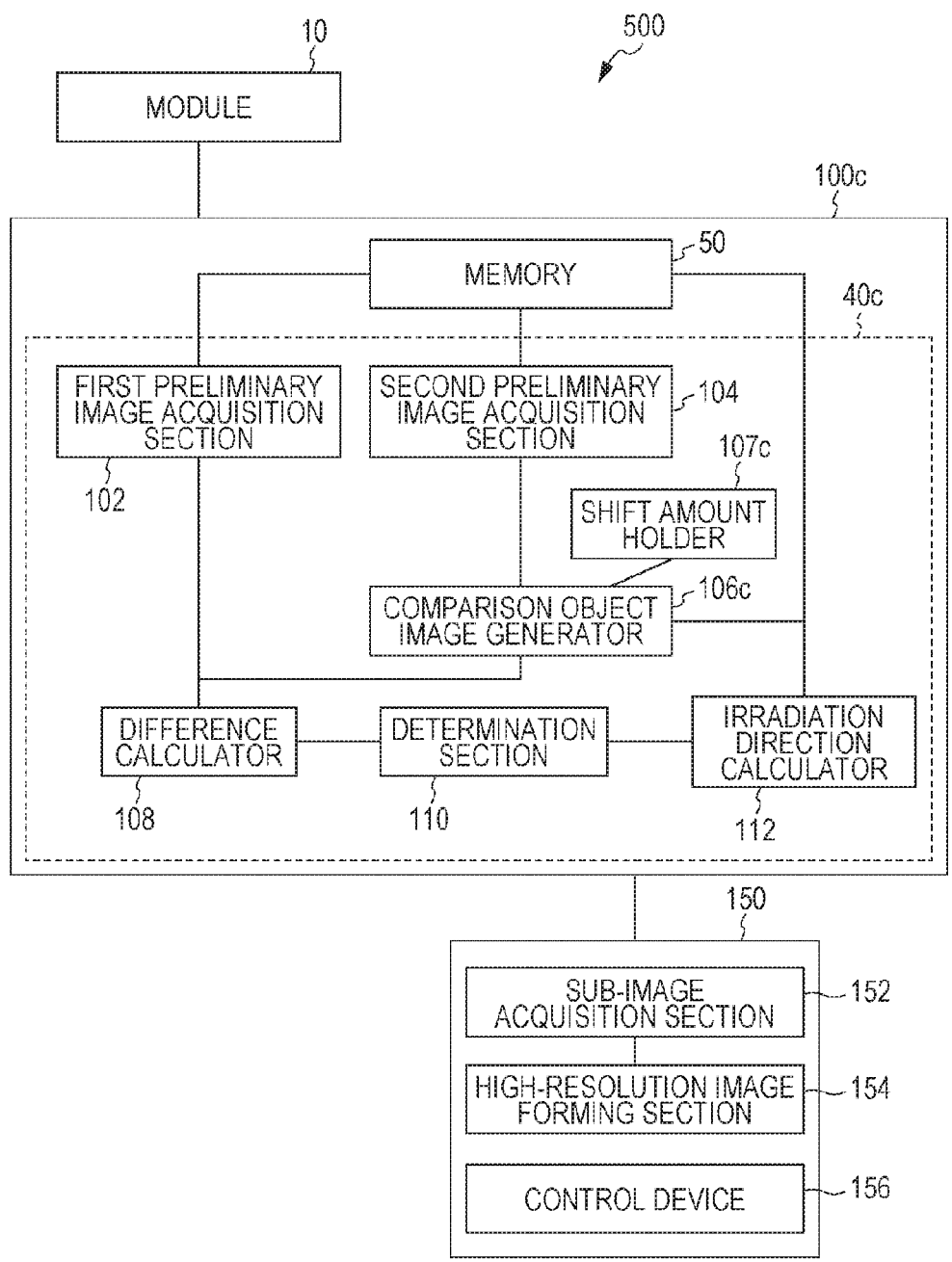
FIG. 24 is a block diagram illustrating another example of the image forming system according to the exemplary embodiment of the present disclosure.

FIG. 24 illustrates still another example of the image forming system according to the exemplary embodiment of the present disclosure. Irradiation direction decision section 40c of image acquisition device 100c in FIG. 24 differs from irradiation direction decision section 40b (see FIG. 20) in that irradiation direction decision section 40c includes not luminance normalizer 105b but shift amount holder 107c connected to comparison object image generator 106c. Shift amount holder 107c can include a known memory element. Shift amount holder 107c may constitute a part of memory 50.

In the following example of the operation of the irradiation direction decision section, each of the first and second preliminary images is acquired once. TABLE 3 illustrates examples of the information indicating first irradiation direction DR1 and the information indicating second irradiation direction DR2, which are stored in memory 50. In TABLE 3, first irradiation direction DR1 and second irradiation direction DR2 have the symmetrical relationship with respect to the subject.

TABLE 3

| ID | FIRST IRRADIATION ANGLE | SECOND IRRADIATION ANGLE |
|---|---|---|
| 1 | −30° | 30° |

In the second specific example, the shifted image in which one of the first and second preliminary images is shifted by one pixel is generated, and the first and second preliminary images are compared to each other by comparing the shifted image to the other of the first and second preliminary images. However, the shift amount indicating how many pixels the acquired image is shifted is not limited to one during the generation of the shifted image. As described below, a plurality of shifted images having different shift amounts may be generated using one of the first and second preliminary images, and compared to the other of the first and second preliminary images.

Figure 25:
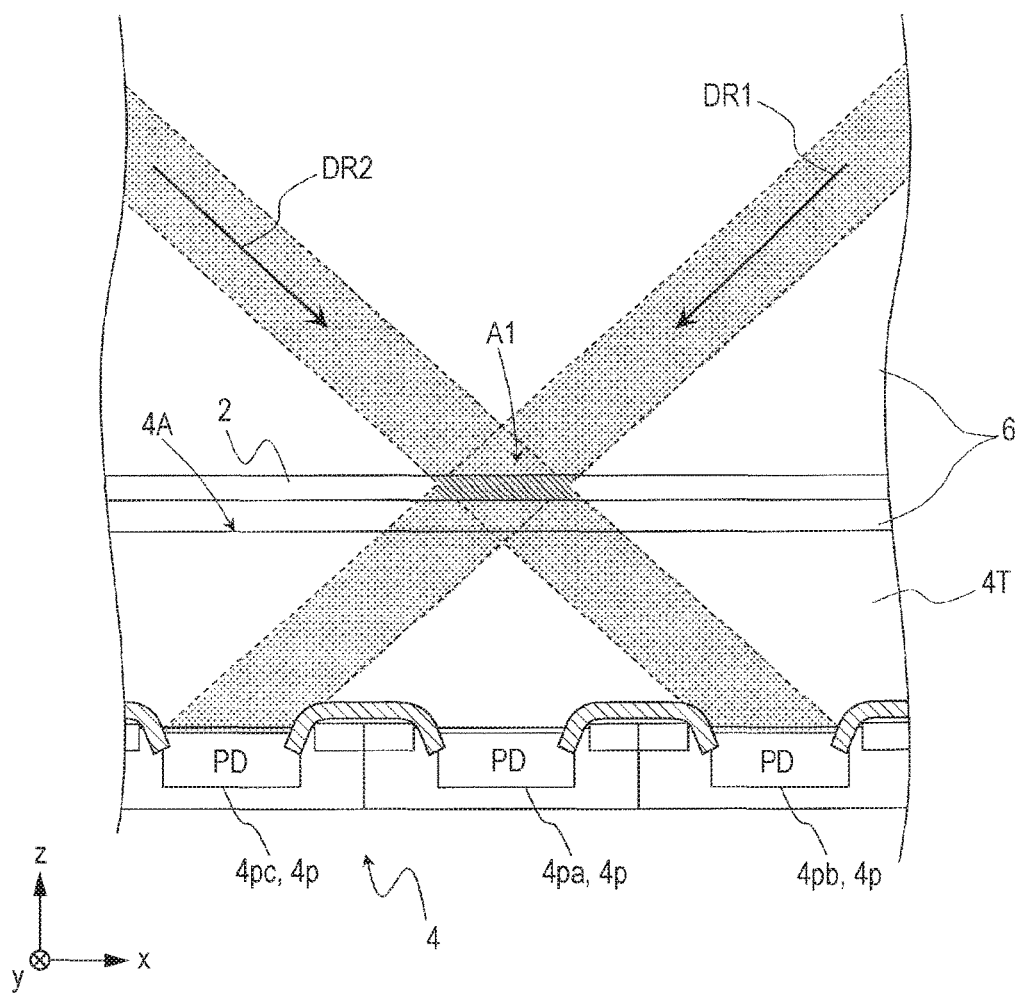
FIG. 25 is a view schematically illustrating examples of first and second irradiation directions DR1 and DR2 in a third specific example.

FIG. 25 schematically illustrates examples of first and second irradiation directions DR1 and DR2 in a third specific example. In the examples of FIG. 25, under the irradiation in first irradiation direction DR1, the light transmitted through region A1 immediately above photodiode 4pa in subject 2 is incident on photodiode 4pc adjacent to the left side of photodiode 4pa. Under the irradiation in second irradiation direction DR2, the light transmitted through region A1 in subject 2 is incident on photodiode 4pb adjacent to the right side of photodiode 4pa. In first and second irradiation directions DR1 and DR2 of FIG. 25, the luminance distribution of the first preliminary image agrees substantially with the luminance distribution of the image in which the second preliminary image is shifted by two pixels in the crosswise direction. That is, the difference between the first and second preliminary images can be minimized when the shift amount is set to a value except for 1. First and second irradiation directions DR1 and DR2 are fixed, and the shift amount is obtained such that the difference between the first and second preliminary images is minimized, whereby the relative disposition between the region through which the beam passes in subject 2 and the photodiode on which the transmitted beam is incident can roughly be recognized before the acquisition of the sub-image.

Figure 26:
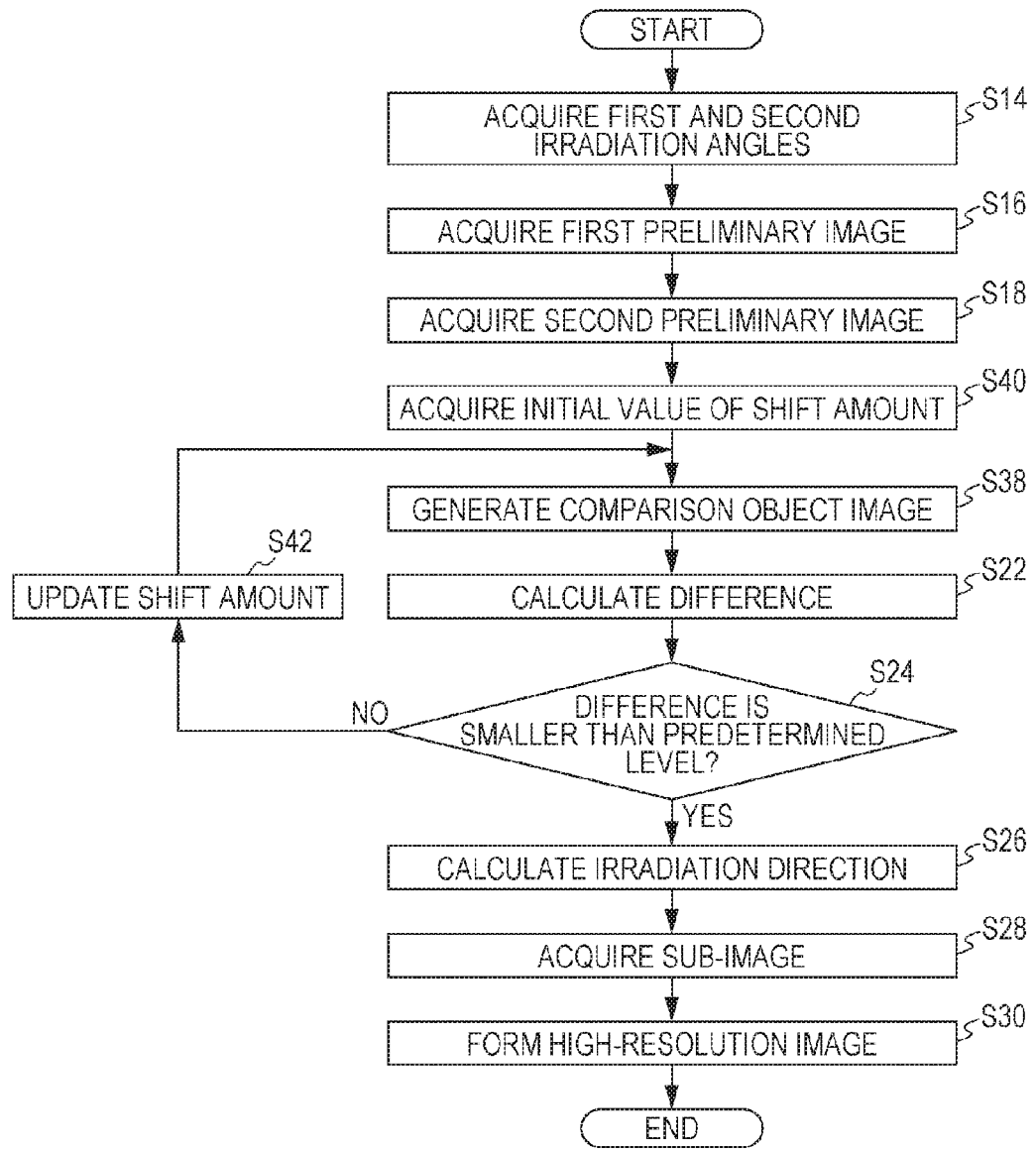
FIG. 26 is a flowchart illustrating still another example of the operation of image forming system 500.

FIG. 26 illustrates still another example of the operation of image forming system 500. In step S14, the information indicating first irradiation direction DR1 and the information indicating second irradiation direction DR2 are read from memory 50. In this case, −30° is read as the first irradiation angle, and 30° is read as the second irradiation angle.

The first preliminary image is acquired in step S16. At this point, the first preliminary image is acquired while the irradiation direction based on the subject is −30°. The information indicating the acquired first preliminary image is temporarily stored in memory 50.

The second preliminary image is acquired in step S18. At this point, the second preliminary image is acquired while the irradiation direction based on the subject is 30°. The information indicating the acquired second preliminary image is temporarily stored in memory 50.

In step S40, comparison object image generator 106c reads a shift amount from shift amount holder 107c. At this point, the shift amount is set to an initial value of 1.

In step S38, comparison object image generator 106c generates the shifted image in which one of the first and second preliminary images is shifted by one pixel. An example in which the shifted image is generated from the second preliminary image will be described below.

The difference between the first preliminary image and the shifted image is calculated in step S22.

In step S24, whether the calculated difference is greater than or equal to the predetermined level is determined. When the difference between the first preliminary image and the shifted image is determined to be less than the predetermined level, the processing goes to step S26. The pieces of processing from step S26 are similar to those in FIG. 19.

When the difference between the first and second preliminary images is determined to be greater than or equal to the predetermined level, the processing goes to step S42. In step S42, comparison object image generator 106c updates the shift amount (typically, increments the shift amount). For example, the shift amount is incremented by 1 to set the shift amount to 2.

The processing returns to step S38 after step S42. The shifted image in which the second preliminary image is shifted by two pixels is generated in step S38. Then the difference between the newly-generated shifted image and the first preliminary image is calculated in step S22. In step S24, whether the calculated difference is greater than or equal to a predetermined level is determined. That is, until the shift amount is found such that the difference between the first preliminary image and the shifted image is minimized, the difference between the first preliminary image and the shifted image is evaluated by changing the shift amount. The number of update times of the shift amount can be set as appropriate. The shift amount is not limited to the initial value of 1. For example, the shift amount may be set to the initial value of 0.

In the third specific example, each of the first and second preliminary images is acquired once. Accordingly, the processing time necessary for the decision of the plurality of irradiation directions can be shortened. The first preliminary image may be acquired after the second preliminary image is acquired.

(Fourth Specific Example of Configuration and Operation of Irradiation Direction Decision Section)

Figure 27:
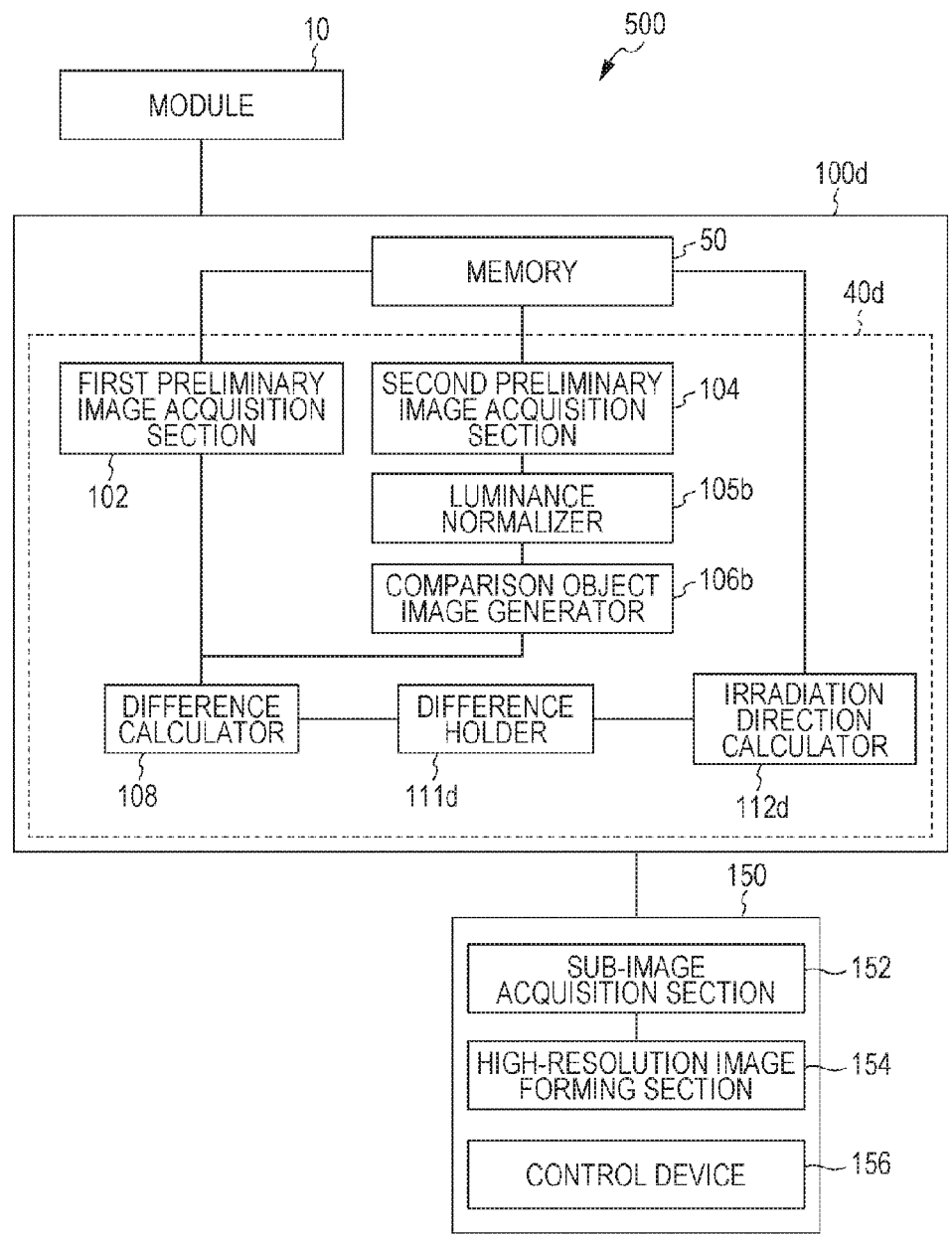
FIG. 27 is a block diagram illustrating still another example of the image forming system according to the exemplary embodiment of the present disclosure.

FIG. 27 illustrates still another example of the image forming system according to the exemplary embodiment of the present disclosure. Irradiation direction decision section 40d of image acquisition device 100d in FIG. 27 differs from irradiation direction decision section 40b (see FIG. 20) in that irradiation direction decision section 40d includes difference holder 111d instead of determination section 110. Difference holder 111d can include a known memory element. Difference holder 111d may constitute a part of memory 50.

In the first to third specific examples, when the difference between the first and second preliminary images is determined to be less than the predetermined level, the difference is not calculated any more. In the following example, at least one first preliminary image and at least one second preliminary image are acquired, and a predetermined number of image sets each of which includes the first and second preliminary images are prepared. The difference between the first and second preliminary images is calculated in each image set, and the difference is evaluated among the image sets. In the following example, the image set having the minimum difference is decided from the plurality of image sets. For the reason similar to that described with reference to FIGS. 22 to 23B, the combination of the first and second irradiation directions in which the difference between the first and second preliminary images is decreased as small as possible is suitable for the calculation of the plurality of irradiation directions used to acquire the sub-images. In the following example, after the image set having the minimum difference is decided, the plurality of different irradiation directions used to acquire the sub-images is decided based on the first and second irradiation directions corresponding to the image set having the minimum difference.

Figure 28:
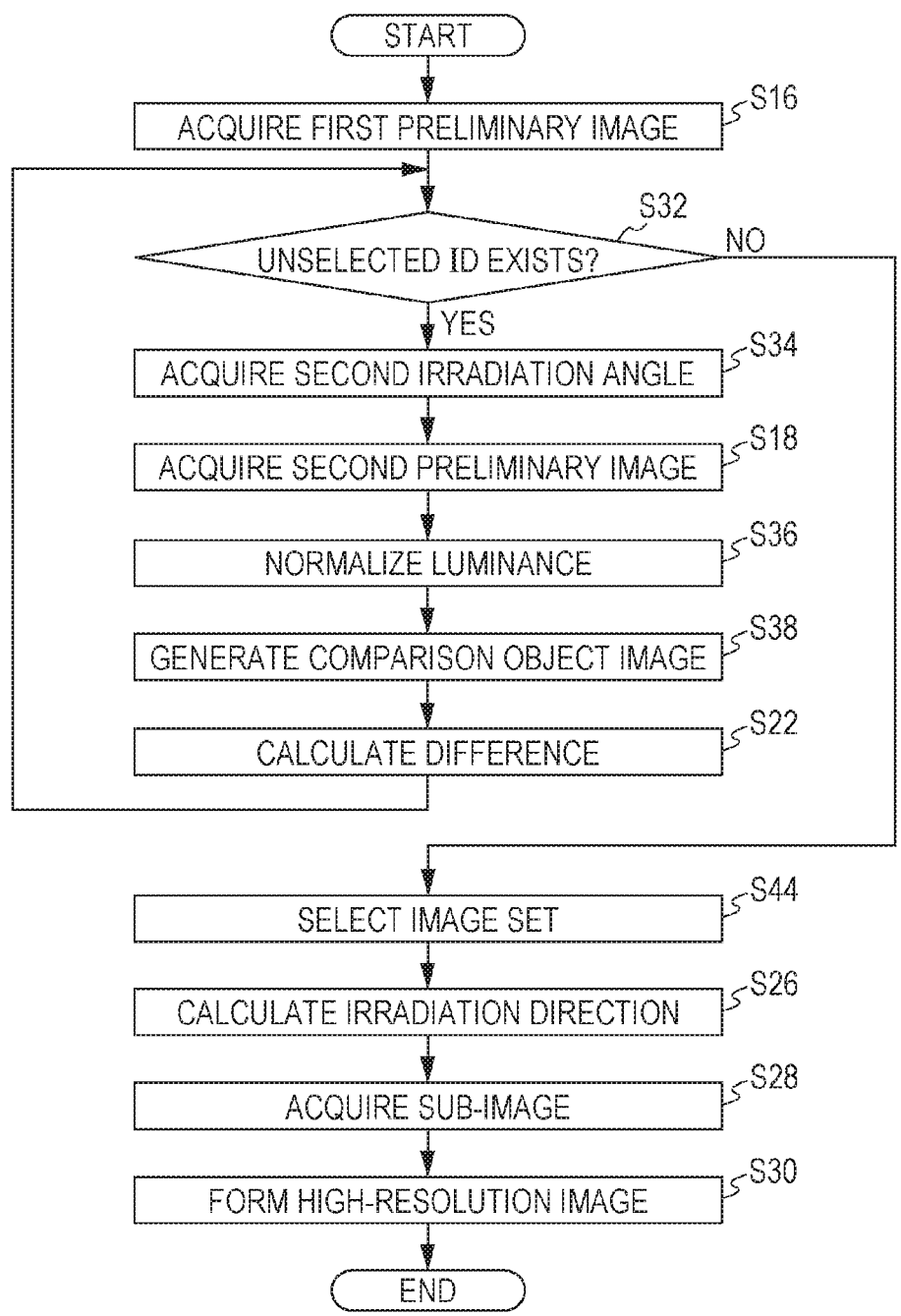
FIG. 28 is a flowchart illustrating still another example of the operation of image forming system 500.

FIG. 28 illustrates still another example of the operation of image forming system 500. Similarly to TABLE 2, the list of the pieces of information indicating second irradiation directions DR2 is stored in memory 50.

The first preliminary image is acquired in step S16. For example, the irradiation direction based on the subject is 0° during the acquisition of the first preliminary image. The information indicating the acquired first preliminary image is temporarily stored in memory 50.

In step S32, whether the second irradiation angle that is not selected yet exists in the list of the second irradiation angles stored in memory 50 is determined. In this case, because the second irradiation angle is not acquired yet, the processing goes to step S34.

Because the pieces of processing in steps S34 to S38 of FIG. 28 are similar to those of the second specific example in FIG. 21, the description is omitted. After the processing in step S38, the difference between the first and second preliminary images is calculated in step S22. The difference calculated in step S22 is one corresponding to the image set including the first preliminary image acquired at a first irradiation angle of 0° and the second preliminary image acquired at a second irradiation angle of 5°. In this example, after the difference is calculated, the information indicating the calculated difference is temporarily stored in difference holder 111d.

Then, the processing returns to step S32, the pieces of processing in steps S34 to S22 are repeated. That is, the difference between the first and second preliminary images is calculated with respect to all the plurality of image sets including the first preliminary image acquired at a first irradiation angle of 0° and the second preliminary image acquired by the change in second irradiation angle. The ID indicated in the first column of TABLE 2 can be used as an index identifying each image set. When the calculation of the difference between the first and second preliminary images is ended with respect to all the IDs included in the list stored in memory 50, the processing goes to step S44.

In step S44, irradiation direction calculator 112d decides the minimum difference from the pieces of difference data stored in difference holder 111d. In other words, irradiation direction calculator 112d decides the image set having the minimum difference in step S44.

In step S26, based on the first and second irradiation directions corresponding to the image set having the minimum difference, irradiation direction calculator 112d calculates the plurality of different irradiation directions used to acquire the sub-images. The following pieces of processing are similar to those in FIG. 19. Thus, the image set having the minimum difference between the first and second preliminary images may be extracted from the plurality of image sets, and the plurality of different irradiation directions used to acquire the sub-images may be decided based on the first and second irradiation directions corresponding to the image set having the minimum difference.

(Fifth Specific Example of Configuration and Operation of Irradiation Direction Decision Section)

Figure 29:
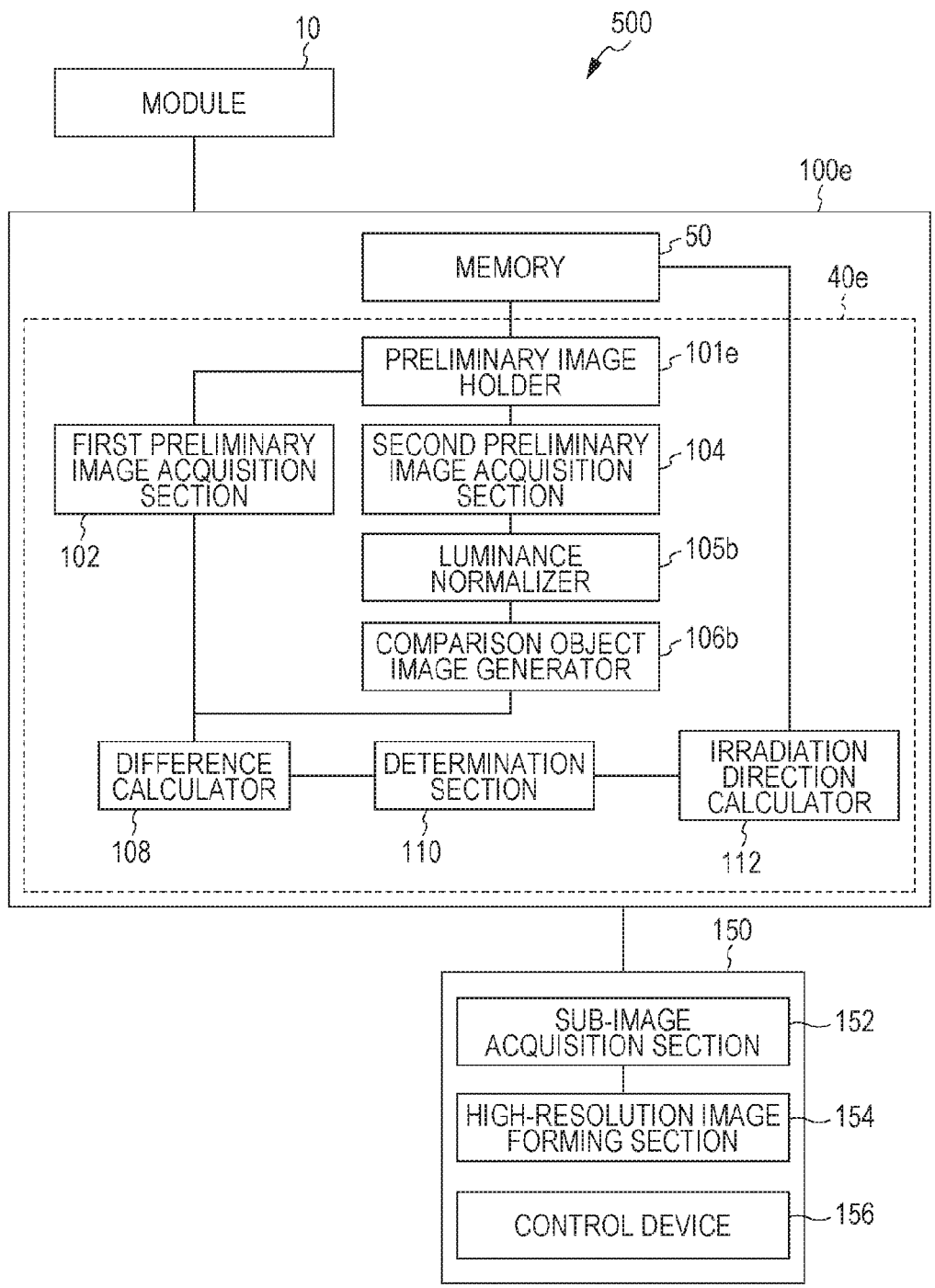
FIG. 29 is a block diagram illustrating still another example of the image forming system according to the exemplary embodiment of the present disclosure.

FIG. 29 illustrates still another example of the image forming system according to the exemplary embodiment of the present disclosure. Irradiation direction decision section 40e of image acquisition device 100e in FIG. 29 differs from irradiation direction decision section 40b (see FIG. 20) in that irradiation direction decision section 40e further includes preliminary image retainer 101e. Preliminary image retainer 101e can include a known memory element. Preliminary image retainer 101e may constitute a part of memory 50.

For example, in the second specific example, the second preliminary image is acquired while the second irradiation angle is changed every time the difference between the first and second preliminary images is calculated. In other words, each of the second preliminary images acquired according to the IDs is used only once in calculating the difference between the first and second preliminary images. Alternatively, as described below, the first and/or second preliminary images acquired according to the irradiation angles different from each other may be used at least twice in the IDs different from each other.

Figure 30:
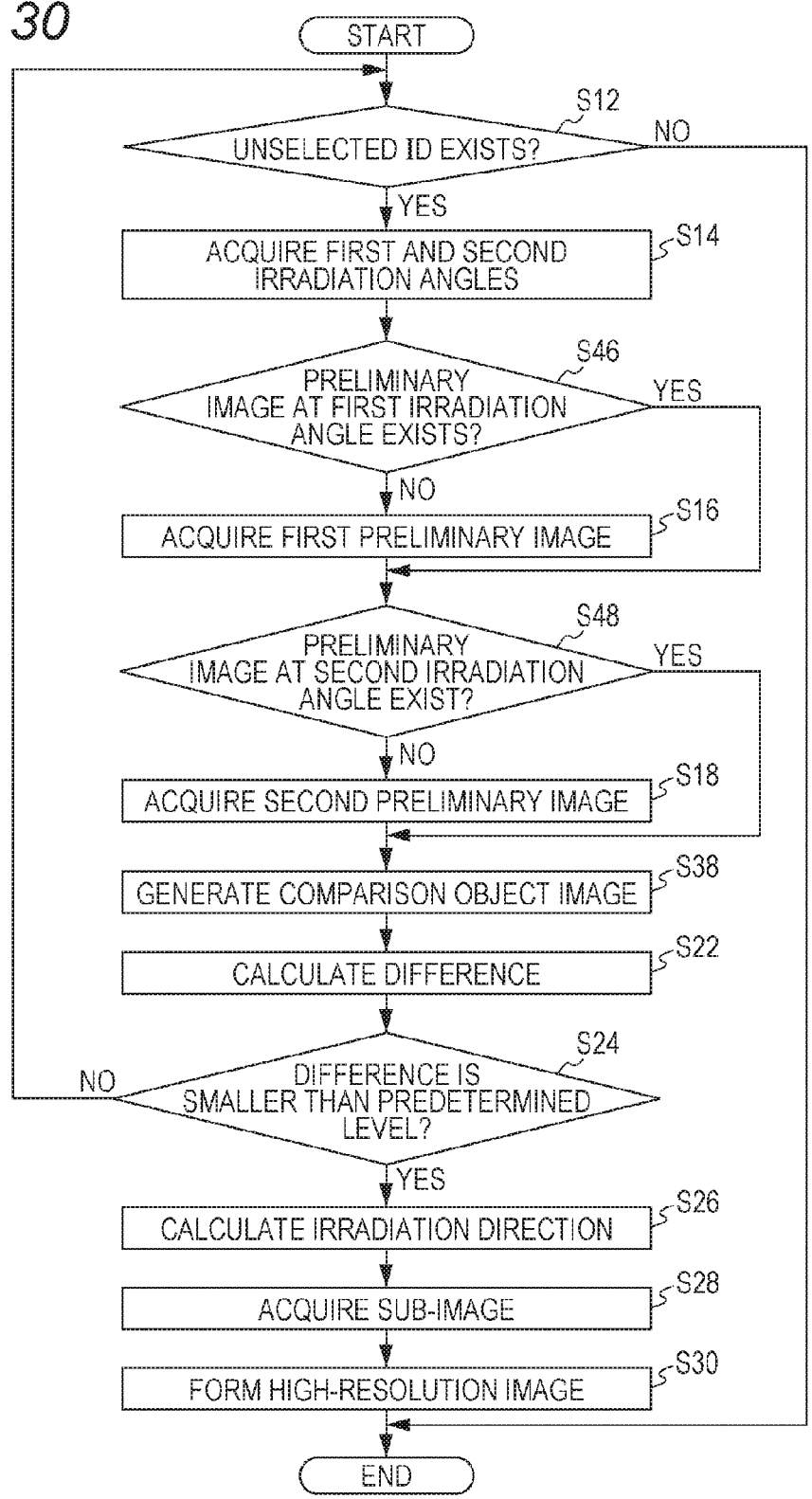
FIG. 30 is a flowchart illustrating still another example of the operation of image forming system 500.

FIG. 30 illustrates still another example of the operation of image forming system 500. In the example of FIG. 30, whether the first and second irradiation angles corresponding to the ID that is not selected yet exist in the list of the first and second irradiation angles stored in memory 50 is determined in step S12. At this point, because the first and second irradiation angles are not acquired yet, the processing goes to step S14. TABLE 4 illustrates examples of the information indicating first irradiation direction DR1 and the information indicating second irradiation direction DR2, which are stored in memory 50. In TABLE 4, some of the irradiation angles are common to the plurality of IDs.

Some of the irradiation angles are common to the first and second irradiation angles.

TABLE 4

| ID | FIRST IRRADIATION ANGLE | SECOND IRRADIATION ANGLE |
|---|---|---|
| 1 | 0° | 5° |
| 2 | 5° | 15° |
| 3 | 0° | 15° |
| 4 | −20° | 0° |
| 5 | −20° | 5° |
| 6 | −20° | 15° |

In step S14, the information indicating first irradiation direction DR1 and the information indicating second irradiation direction DR2 are read from memory 50. In this case, 0° is read as the first irradiation angle, and 5° is read as the second irradiation angle.

In step S46, first preliminary image acquisition section 102 determines whether the data of the preliminary image (first or second preliminary image) acquired at an irradiation angle of 0° is stored in preliminary image retainer 101e. At this point, neither the first preliminary image nor the second preliminary image is acquired. Therefore, the processing goes to step S16. In step S16, the first preliminary image is acquired at a first irradiation angle of 0°. The information indicating the acquired first preliminary image is temporarily stored in preliminary image retainer 101e. On the other hand, when the data of the preliminary image acquired at an irradiation angle of 0° is already stored in preliminary image retainer 101e, the first preliminary image acquisition processing in step S16 is skipped.

In step S48, second preliminary image acquisition section 104 determines whether the data of the preliminary image acquired at an irradiation angle of 5° is stored in preliminary image retainer 101e. At this point, only the data of the first preliminary image acquired at an irradiation angle of 0° is stored in preliminary image retainer 101e. Therefore, the processing goes to step S18. In step S18, the second preliminary image is acquired at a second irradiation angle of 5°. The information indicating the acquired second preliminary image is temporarily stored in preliminary image retainer 101e. On the other hand, when the data of the preliminary image acquired at an irradiation angle of 5° is already stored in preliminary image retainer 101e, the second preliminary image acquisition processing in step S18 is skipped.

In step S38, the shifted image is generated from the second preliminary image. In step S22, the difference between the first and second preliminary images is calculated. Luminance normalizer 105b normalizes the luminance in advance of the calculation of the difference as needed basis. In this case, the difference between the first and second preliminary images is calculated using the data of the first preliminary image stored in preliminary image retainer 101e and the data of the shifted image generated in step S38.

In step S24, whether the difference calculated in step S22 is greater than or equal to the predetermined level is determined. When the difference between the first and second preliminary images is determined to be less than the predetermined level, the processing goes to step S26. On the other hand, when the difference between the first and second preliminary images is determined to be greater than or equal to the predetermined level, the processing returns to step S12.

When the processing returns to step S12, whether the first and second irradiation angles corresponding to the ID that is not selected yet exist is determined again. At this point, because the first and second irradiation angles that are of IDs 2 to 6 in TABLE 4 are not acquired yet, the processing goes to step S14.

In step S14, the first and second irradiation angles of ID 2 are read. In this case, 5° is read as the first irradiation angle, and 15° is read as the second irradiation angle.

In step S46, whether the data of the preliminary image acquired at an irradiation angle of 5° is stored in preliminary image retainer 101e is determined. In this example, the data of the second preliminary image acquired at an irradiation angle of 5° is stored in preliminary image retainer 101e. Accordingly, the processing in step S16 is skipped, but the first preliminary image is not acquired.

In step S48, whether the data of the preliminary image acquired at an irradiation angle of 15° is stored in preliminary image retainer 101e is determined. In this example, neither the data of the first preliminary image acquired at an irradiation angle of 15° nor the data of the second preliminary image acquired at an irradiation angle of 15° is stored in preliminary image retainer 101e. Therefore, the processing goes to step S18. In step S18, the second preliminary image is acquired at a second irradiation angle of 15°. The information indicating the acquired second preliminary image is also temporarily stored in preliminary image retainer 101e.

In step S38, the shifted image is generated from the second preliminary image acquired at a second irradiation angle of 15°.

The difference between the first and second preliminary images is calculated in step S22. At this point, the data of the second preliminary image, which is acquired at an irradiation angle of 5° and stored in preliminary image retainer 101e, is used as the data of the first preliminary image acquired at an irradiation angle of 5°. The difference is calculated using the data of the second preliminary image, which is acquired at an irradiation angle of 5° and stored in preliminary image retainer 101e, and the shifted image generated from the second preliminary image acquired at an irradiation angle of 15°. Thus, in the example of FIG. 30, in the case that the plurality of identical angles exist in the list of the first and second irradiation angles, the difference between the first and second preliminary images is calculated using the already-acquired data of the preliminary image. Therefore, the number of imaging times can be reduced compared with the case that the first and second preliminary images are taken for each ID.

In step S24, whether the difference calculated in step S22 is greater than or equal to the predetermined level is determined. When the difference between the first and second preliminary images is determined to be greater than or equal to the predetermined level, the processing returns to step S12.

When the processing returns to step S12, whether the first and second irradiation angles corresponding to the ID that is not selected yet exist is determined again. Then, the processing goes to step S14.

In step S14, the first and second irradiation angles of ID 3 are read. In this case, 0° is read as the first irradiation angle, and 15° is read as the second irradiation angle.

In step S46, whether the data of the preliminary image acquired at an irradiation angle of 0° is stored in preliminary image retainer 101e is determined. In this example, the data of the first preliminary image acquired at an irradiation angle of 0° is stored in preliminary image retainer 101e. Accordingly, the processing in step S16 is skipped.

In step S48, whether the data of the preliminary image acquired at an irradiation angle of 15° is stored in preliminary image retainer 101e is determined. In this example, the data of the second preliminary image acquired at an irradiation angle of 15° is stored in preliminary image retainer 101e. Accordingly, the processing in step S18 is skipped.

In step S38, the shifted image is generated from the second preliminary image, which is acquired at a second irradiation angle of 15° and stored in preliminary image retainer 101e. In step S22, the difference between the first and second preliminary images is calculated. At this point, the difference is calculated using the data of the first preliminary image, which is acquired at an irradiation angle of 0° and stored in preliminary image retainer 101e, and the shifted image generated in step S38.

In the case that the difference between the first and second preliminary images is calculated using the data of the already-acquired preliminary image, it is necessary to perform the imaging once at each irradiation direction. Therefore, the time necessary for the imaging can be shortened, and the processing time necessary for the decision of the plurality of irradiation directions can be shortened. In the case that memory 50 acts as preliminary image retainer 101e, the operation in FIG. 30 can be performed by the configuration similar to that of irradiation direction decision section 40b in FIG. 20.

(Another Example of Principle Used to Decide Plurality of Irradiation Directions)

Another example of the principle applicable to the decision of the plurality of irradiation directions in the exemplary embodiment will be described below with reference to FIGS. 31 to 33. In the following example, roughly the first preliminary image is acquired by irradiating the subject with illumination light in the direction normal to the imaging surface of the imaging element, and the shifted image is generated from the acquired first preliminary image. The imaging is performed while the irradiation direction (second irradiation direction) is changed, thereby acquiring the plurality of second preliminary images. Therefore, the plurality of image sets corresponding to the plurality of second irradiation directions can be constructed. Then, a similarity between the first preliminary image and the second preliminary image and a value of an evaluation function calculated from the similarity between the shifted image and the second preliminary image are obtained with respect to each image set. The plurality of irradiation directions used to acquire the sub-images are decided based on the value of the evaluation function obtained with respect to each image set. The case that the double high resolving power is obtained in the x-direction will be described below for convenience.

Figure 31:
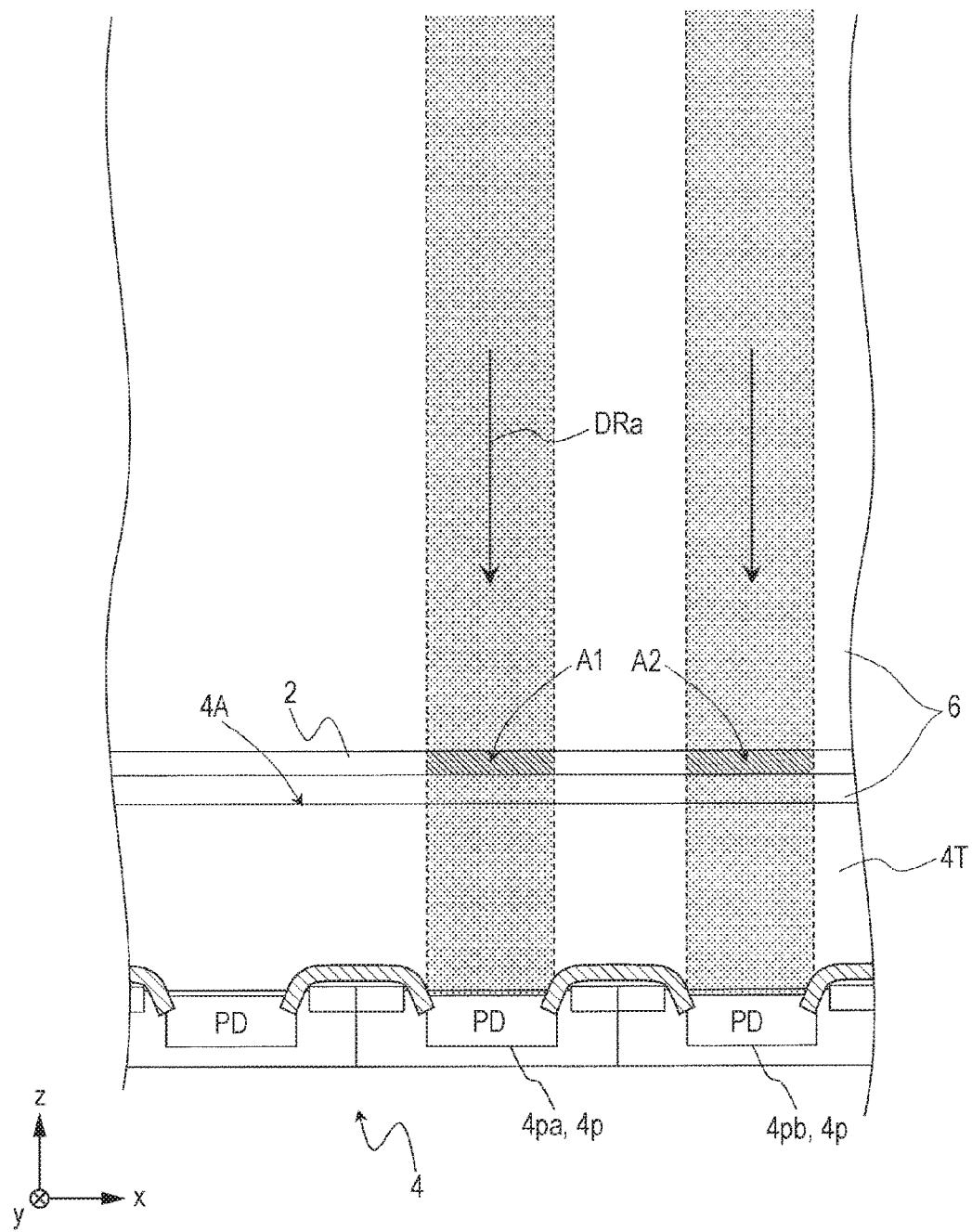
FIG. 31 is a sectional view schematically illustrating an example of the relationship between the irradiation direction of the illumination light and the region transmitting the illumination light in subject 2.

FIG. 31 schematically illustrates a state in which the subject is irradiated with illumination light in the direction normal to imaging surface 4A of image sensor 4. Referring to FIG. 31, the beam transmitted through region A1 in subject 2 is incident on photodiode 4pa, and the beam transmitted through region A2 in subject 2 is incident on photodiode 4pb adjacent to photodiode 4pa along the x-direction. The pixel luminance acquired with photodiode 4pa in the irradiation direction DRa of FIG. 31 indicates the amount of light transmitted through region A1 in subject 2. The pixel luminance acquired with photodiode 4pb in the irradiation direction DRa of FIG. 31 indicates the amount of light transmitted through region A2 in subject 2. Assuming that $\Gamma$ is an angle formed between line N (not illustrated in FIG. 31) normal to imaging surface 4A of image sensor 4 and the beam incident on subject 2, $\Gamma=0$ is obtained. Hereinafter, the pixel luminance acquired with photodiode 4pa in irradiation direction DRa of FIG. 31 and the pixel luminance acquired with photodiode 4pb are referred to as $Xa^0$ and $Xb^0$, respectively.

Figure 32:
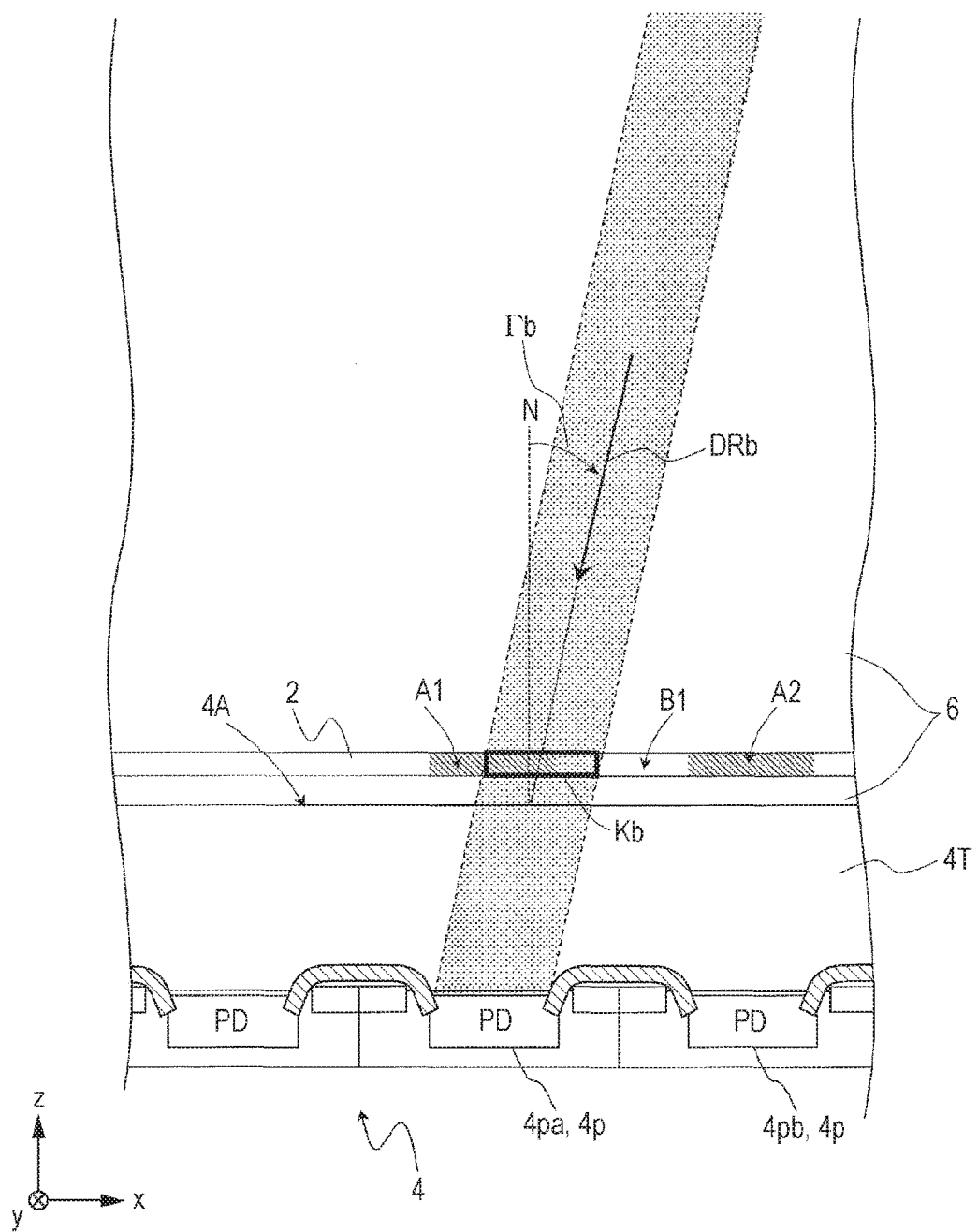
FIG. 32 is a sectional view schematically illustrating another example of the relationship between the irradiation direction of the illumination light and the region transmitting the illumination light in subject.

FIG. 32 schematically illustrates an example of the relationship between the irradiation direction of the illumination light and the region transmitting the illumination light in subject 2 when angle $\Gamma$ formed between line N normal to imaging surface 4A and the beam incident on subject 2 is increased from the state in FIG. 31. The beam transmitted through a part of region A1 in subject 2 and the beam transmitted through a part of region B1 located between regions A1 and A2 are incident on photodiode 4pa in irradiation direction DRb of FIG. 32. Assuming that $\Gamma b$ ($\Gamma b > 0$) is an angle formed between line N normal to imaging surface 4A and the beam incident on subject 2, and that $Xa^{\Gamma b}$ is a pixel luminance acquired with photodiode 4pa, luminance $Xa^{\Gamma b}$ indicates the amount of light transmitted through region Kb indicated by a bold-line rectangle in FIG. 32 in subject 2. Region Kb includes a part of region A1, but does not include region A2. Therefore, generally luminance $Xa^{\Gamma b}$ indicates a value closer to luminance $Xa^0$ than luminance $Xb^0$. At this point, it is assumed that the normalization is performed on the luminance obtained by performing the imaging in the state of $\Gamma \neq 0$. The same holds true for the following description.

Figure 33:
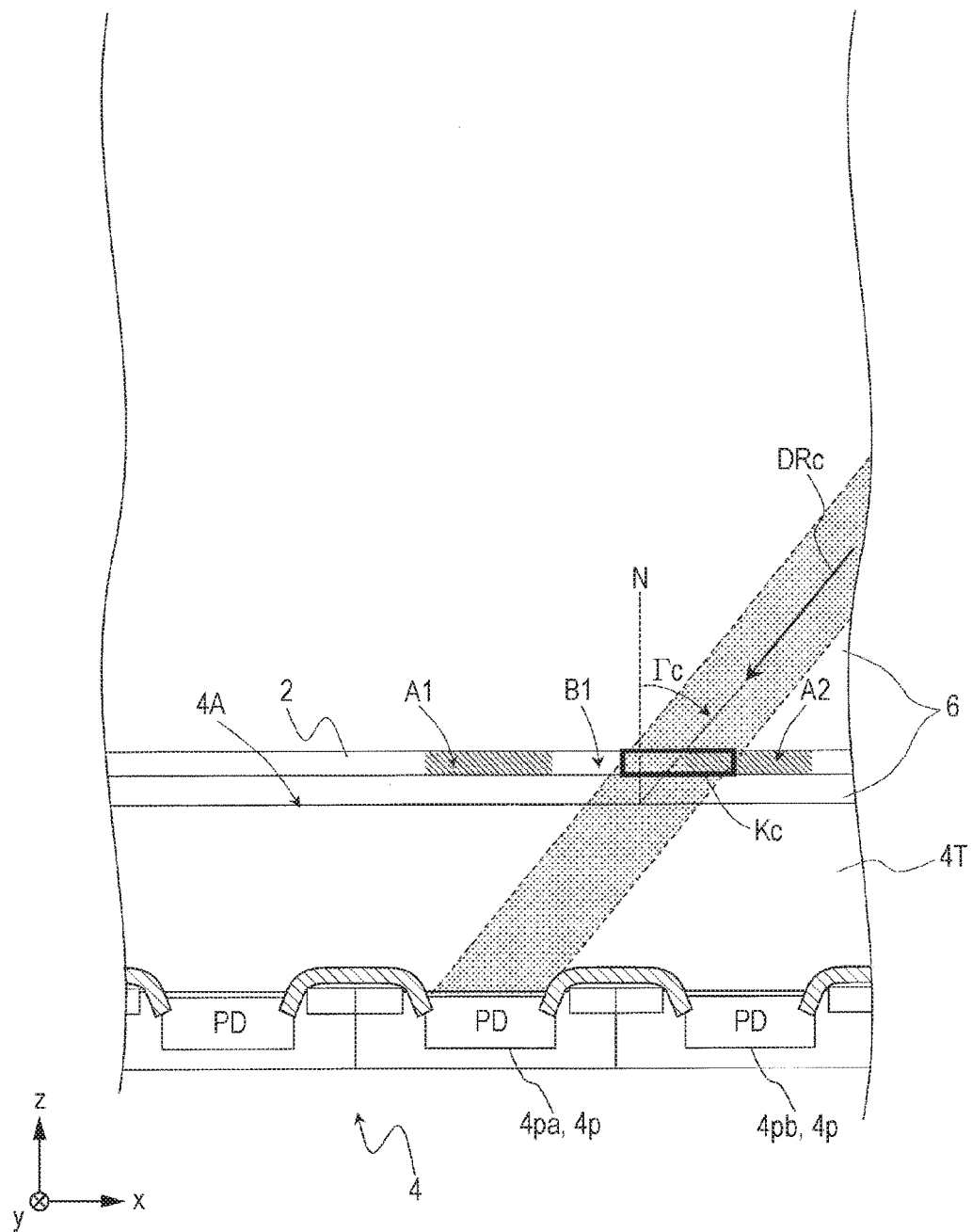
FIG. 33 is a sectional view schematically illustrating another example of the relationship between the irradiation direction of the illumination light and the region transmitting the illumination light in subject 2.

FIG. 33 schematically illustrates an example of the relationship between the irradiation direction of the illumination light and the region transmitting the illumination light in subject 2 when angle $\Gamma$ is further increased from the state in FIG. 32. The beam transmitted through parts of regions B1 and A2 in subject 2 is incident on photodiode 4pa in irradiation direction DRc of FIG. 33. Assuming that $\Gamma c$ ($\Gamma c > \Gamma b$) is an angle formed between line N normal to imaging surface 4A and the beam incident on subject 2, and that $Xa^{\Gamma c}$ is a pixel luminance acquired with photodiode 4pa, luminance $Xa^{\Gamma c}$ indicates the amount of light transmitted through region Kc indicated by a bold-line rectangle in FIG. 33 in subject 2. Region Kc includes a part of region A2, but does not include region A1. Therefore, generally luminance $Xa^{\Gamma c}$ indicates a value closer to luminance $Xb^0$ than luminance $Xa^0$.

When angle $\Gamma$ is further increased from the state in FIG. 33, the beam transmitted through region A2 in subject 2 is incident on photodiode 4pa at a certain angle. At this point, pixel luminance acquired with photodiode 4pa agrees substantially with luminance $Xb^0$. That is, the luminance distribution of the obtained image of subject 2 agrees with the luminance distribution of the image in which the image acquired in the irradiation direction DRa of FIG. 31 is shifted by one pixel. As is clear from the principle described with reference to FIGS. 1A to 6, even if the image of subject 2 is acquired in the irradiation direction in which the pixel luminance acquired with photodiode 4pa agrees substantially with luminance $Xb^0$, the obtained image is useless for improving the resolving power. This is because, in the principle described with reference to FIGS. 1A to 6, the high-resolution image is formed using the plurality of sub-images including the images constructed with different parts of subject 2.

Therefore, it is considered that the irradiation direction suitable for the acquisition of the sub-image exists between the irradiation direction in FIG. 31 and the irradiation direction in which the pixel luminance acquired with photodiode 4$pa$ agrees substantially with luminance Xb$^o$. It is useful to find the irradiation direction in which the beam transmitted through region B1 between regions A1 and A2 in subject 2 is incident on photodiode 4$pa$ (or photodiode 4$pb$). In other words, it is necessary to find the irradiation direction in which the image, which is different from both the image of subject 2 acquired under the irradiation in the direction normal to imaging surface 4A and the image in which the subject image acquired under the irradiation in the direction normal to imaging surface 4A is shifted by one pixel in the −x-direction, can be acquired. A specific example of an irradiation direction searching method will be described below.

The following two functions $E^o(\Gamma)$ and $E^s(\Gamma)$ are defined.

$$E^o(\Gamma)=\Sigma'(X_i^o-X_i(\Gamma))^2 \qquad (1)$$

$$E^s(\Gamma)=\Sigma'(X_i^s-X_i(\Gamma))^2 \qquad (2)$$

In the equations (1) and (2), subscript i is an index specifying the pixel included in the acquired image (i=1, 2, . . . , M (M is an integer)). In the equation (1), $X_i^o$ expresses an ith pixel luminance acquired under the irradiation in the direction normal to imaging surface 4A. In the equations (1) and (2), $X_i(\Gamma)$ expresses an ith pixel luminance acquired in the irradiation direction that is tilted by an angle $\Gamma$ from the direction normal to imaging surface 4A. $X_i^o$ and $X_i(\Gamma)$ are pixel luminances acquired with an ith photodiode. In the equation (2), $X_i^s$ expresses a luminance of an ith pixel in the pixels included in the image in which the image acquired under the irradiation in the direction normal to imaging surface 4A is shifted by one pixel in the −x-direction (shifted image). $X_i^s$ is a pixel luminance acquired with an (i+1)th photodiode, and $X_i^s$ is substantially equal to $X_{i+1}^o$. The shifted image does not include an Mth pixel.

In the equations (1) and (2), sum $\Sigma'$ expresses a sum of indices i. The sum is calculated in the case that the evaluation is performed with respect to the plurality of pixels. For example, the sum is calculated in a range of sum i=1 to (M−1). The sum may be calculated with respect to typical pixels. In the case that the evaluation is performed with respect to the pixel of certain fixed index i, it is not necessary to calculate the sum of indices i.

A value of function $E^o(\Gamma)$ of the equation (1) indicates the similarity between the subject image acquired under the irradiation in the direction normal to imaging surface 4A and the subject image acquired in the irradiation direction tilted by angle $\Gamma$ from the direction normal to imaging surface 4A. On the other hand, a value of function $E^s(\Gamma)$ of the equation (2) indicates the similarity between the image in which the subject image acquired under the irradiation in the direction normal to imaging surface 4A is shifted by one pixel in the −x-direction and the subject image acquired in the irradiation direction tilted by angle $\Gamma$ from the direction normal to imaging surface 4A. Particularly, $E^o(0)=0$, and $E^s(\Gamma)$ is substantially zero in the irradiation direction in which the pixel luminance acquired with photodiode 4$pa$ agrees substantially with luminance Xb$^o$.

Then, evaluation function $F(\Gamma)$ is defined using functions $E^o(\Gamma)$ and $E^s(\Gamma)$.

$$F(\Gamma)=(E^o(\Gamma)E^s(\Gamma))/(E^o(\Gamma)+E^s(\Gamma)) \qquad (3)$$

A value of $F(\Gamma)$ calculated using the equation (3) is an example of the difference between the first and second preliminary images. At this point, when one of functions $E^o(\Gamma)$ and $E^s(\Gamma)$ has a large value, the other has a small value. Therefore, function $F(\Gamma)$ is maximized at angle $\Gamma$ indicating the irradiation direction in which the image, which is different from both the image of subject 2 acquired under the irradiation in the direction normal to imaging surface 4A and the image in which the subject image acquired under the irradiation in the direction normal to imaging surface 4A is shifted by one pixel in the −x-direction, can be acquired. The irradiation direction suitable for the acquisition of the sub-image can be found by obtaining angle $\Gamma$ at which function $F(\Gamma)$ is maximized. Thus, the relative disposition between the region through which the beam passes in subject 2 and the photodiode on which the transmitted beam is incident can be recognized in advance of the acquisition of the sub-image by obtaining angle $\Gamma$ at which function $F(\Gamma)$ is maximized.

(Sixth Specific Example of Configuration and Operation of Irradiation Direction Decision Section)

Figure 34:
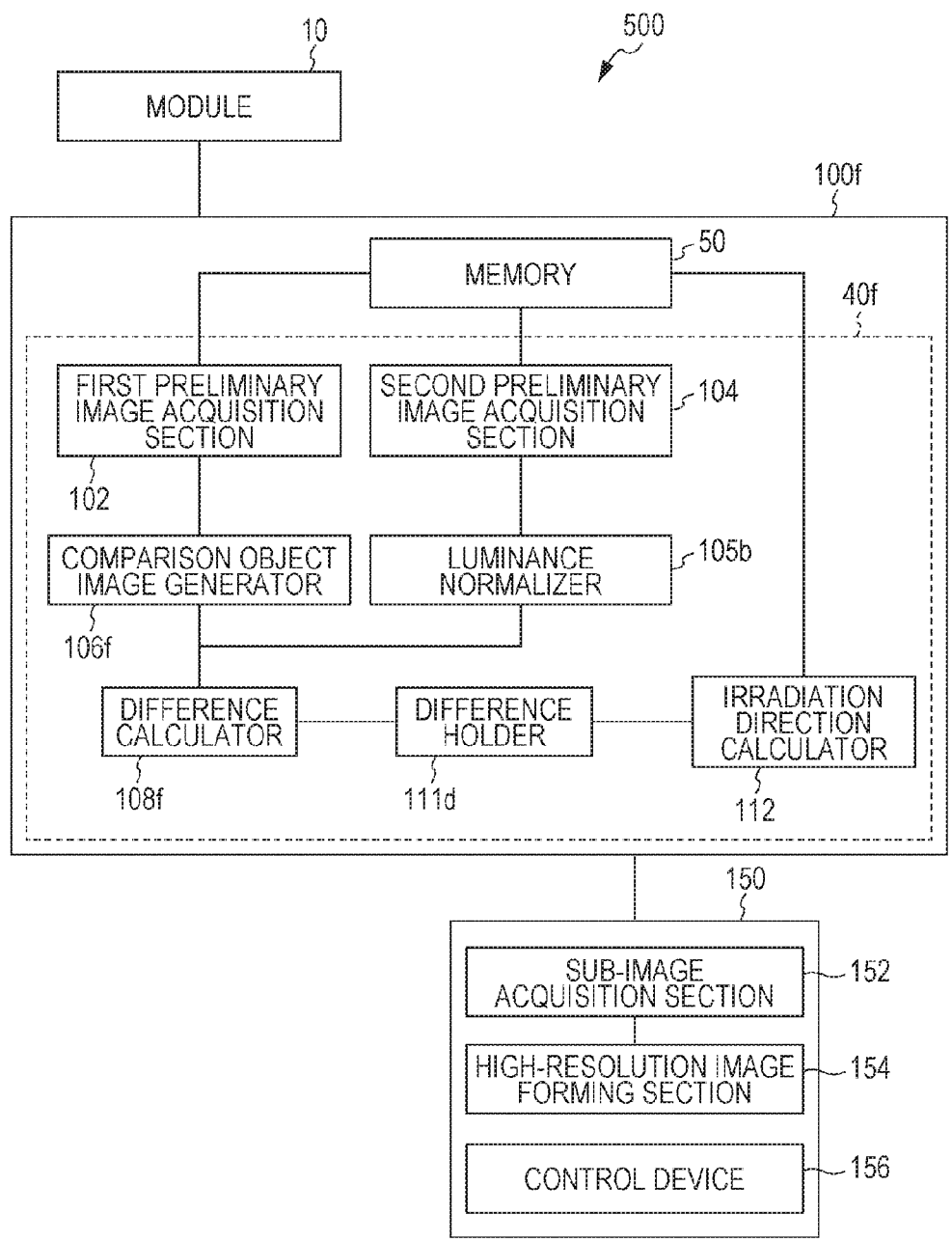
FIG. 34 is a block diagram illustrating still another example of the image forming system according to the exemplary embodiment of the present disclosure.

FIG. 34 illustrates still another example of the image forming system according to the exemplary embodiment of the present disclosure. Irradiation direction decision section 40$f$ of image acquisition device 100$f$ in FIG. 34 differs from irradiation direction decision section 40$b$ (see FIG. 20) in that irradiation direction decision section 40$f$ includes not comparison object image generator 106$b$ but comparison object image generator 106$f$ connected to first preliminary image acquisition section 102. Irradiation direction decision section 40$f$ also includes difference holder 111$d$ instead of determination section 110.

Figure 35:
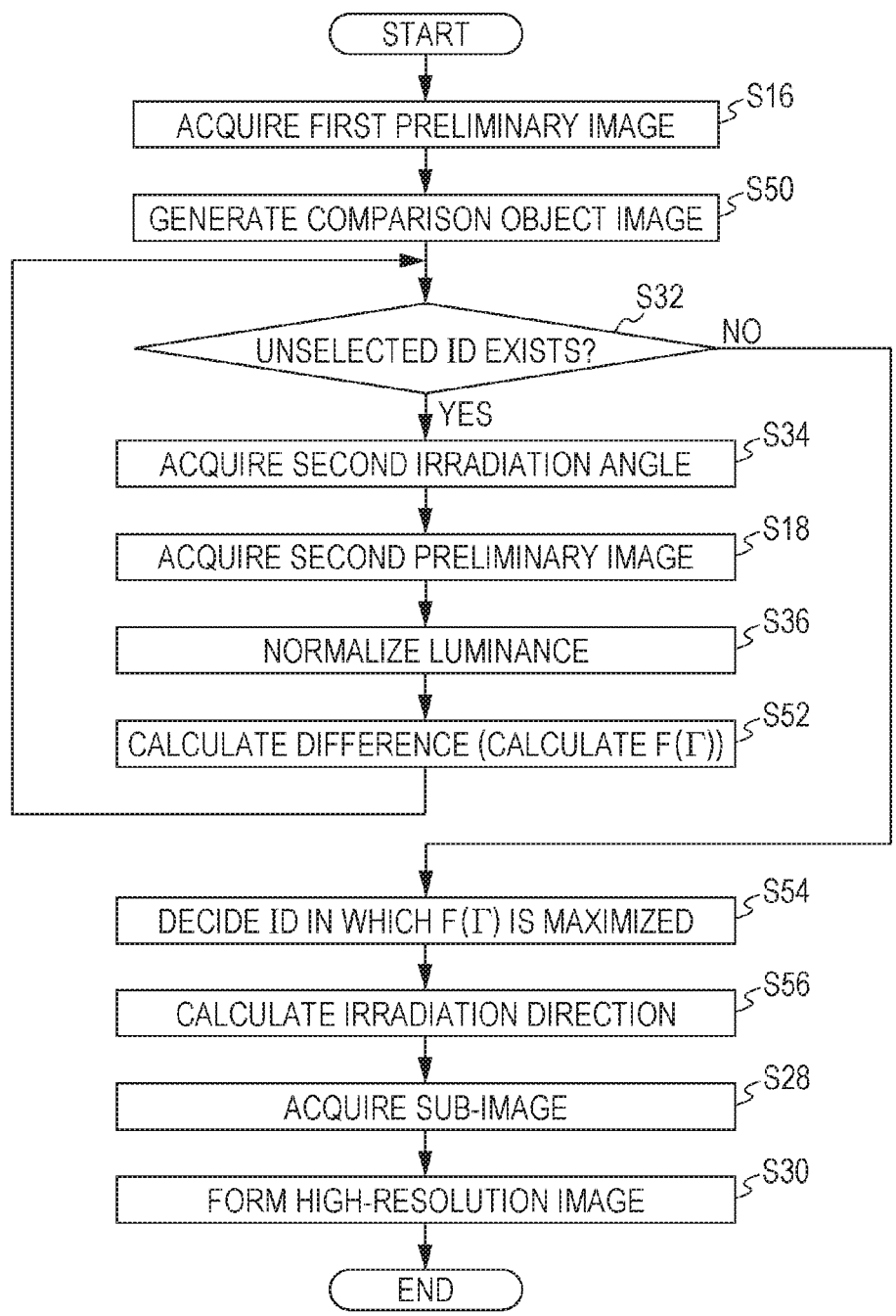
FIG. 35 is a flowchart illustrating still another example of the operation of image forming system 500.

FIG. 35 illustrates another example of the operation of image forming system 500. In the following example, the plurality of irradiation directions are decided using the principle described with reference to FIGS. 31 to 33. In the following example, similarly to the processing of the second specific example in FIG. 21, the first preliminary image is acquired once. The second preliminary image is acquired a plurality of times while the second irradiation direction is changed. The information indicating second irradiation direction DR2 is stored in memory 50. TABLE 5 illustrates an example of the information indicating second irradiation direction DR2.

TABLE 5

| ID | SECOND IRRADIATION ANGLE |
|---|---|
| 1 | 2° |
| 2 | 4° |
| 3 | 6° |
| 4 | 8° |
| 5 | 10° |
| 6 | 12° |
| 7 | 14° |

The first preliminary image is acquired in step S16. At this point, the first preliminary image is acquired while the irradiation direction based on the subject is 0°. The information indicating the acquired first preliminary image is temporarily stored in memory 50.

In step S50, comparison object image generator 106*f* generates the shifted image in which the first preliminary image is shifted by one pixel in the −x-direction.

In step S32, whether the second irradiation angle corresponding to the ID that is not selected yet exists in the list of the second irradiation angles stored in memory 50 is determined. In this case, because the second irradiation angle is not acquired yet, the processing goes to step S34.

In step S34, second preliminary image acquisition section 104 reads the information indicating second irradiation direction DR2 from memory 50. At this point, 2° is read as the second irradiation angle.

The second preliminary image is acquired in step S18. At this point, the second preliminary image is acquired while the irradiation direction based on the subject is 2°. The information indicating the acquired second preliminary image is temporarily stored in memory 50.

In step S36, luminance normalizer 105*b* normalizes the luminance of the acquired second preliminary image.

In step S52, evaluation function $F(\Gamma)$ is calculated using the equation (3). For example, difference calculator 108*f* calculates evaluation function $F(\Gamma)$. A calculation result is temporarily stored in difference holder 111*d* while associated with the ID (that is, the irradiation angle).

Then, the processing returns to step S32, the pieces of processing in steps S32 to S52 are repeated. When evaluation function $F(\Gamma)$ is obtained with respect to all the IDs included in the list of the second irradiation angles stored in memory 50, the processing goes to step S54.

In step S54, values of evaluation function $F(\Gamma)$ stored in difference holder 111*d* are compared to each other to decide the ID in which evaluation function $F(\Gamma)$ is maximized. For example, irradiation direction calculator 112 performs the comparison between the values of evaluation function $F(\Gamma)$. As described in FIGS. 31 to 33, angle $\Gamma$ at which the evaluation function $F(\Gamma)$ is maximized indicates the irradiation direction suitable for the acquisition of the sub-image.

In step S56, based on the ID in which evaluation function $F(\Gamma)$ is maximized, irradiation direction calculator 112 decides or calculates the plurality of irradiation directions used to acquire the sub-images. The information indicating the plurality of irradiation directions is stored in memory 50, and used in the later-described sub-image acquisition step.

The following pieces of processing are similar to those in FIG. 19. For example, the sub-image is acquired at each of an irradiation angle of 0° and the irradiation angle of the ID in which evaluation function $F(\Gamma)$ is maximized, and the high-resolution image is formed using the sub-images.

In this specific example, the second irradiation angle can appropriately be set. In the case that N the resolving power is to be increased by N times in the x-direction, it is necessary to obtain values of evaluation function $F(\Gamma)$ with respect to at least N different irradiation directions between the direction normal to the imaging surface of the imaging element and the irradiation direction in which the pixel luminance acquired with photodiode 4*pa* agrees substantially with luminance $Xb^0$. The N different irradiation directions can be calculated using the distance from the imaging surface to the light source and the array pitch between the photodiodes. The N different irradiation directions may symmetrically be set with respect to the direction normal to the imaging surface of the imaging element. The N different irradiation directions are not necessarily set at equal intervals. Similarly to the above example, the irradiation direction suitable for the acquisition of the sub-image can be decided in the y-direction or u-direction. Accordingly, the resolving power can be increased by N times in the plane parallel to the imaging surface of the image sensor.

(Image Sensor Used in Module)

In the exemplary embodiment, image sensor 4 is not limited to the CCD image sensor, but image sensor 4 may be a CMOS (Complementary Metal-Oxide Semiconductor) image sensor or other image sensors (for example, a photoelectric conversion film laminated image sensor (to be described later)). The CCD image sensor and the CMOS image sensor may be of a surface irradiation type or a rear surface irradiation type. A relationship between an element structure of the image sensor and the light incident on the photodiode of the image sensor will be described below.

Figure 36:
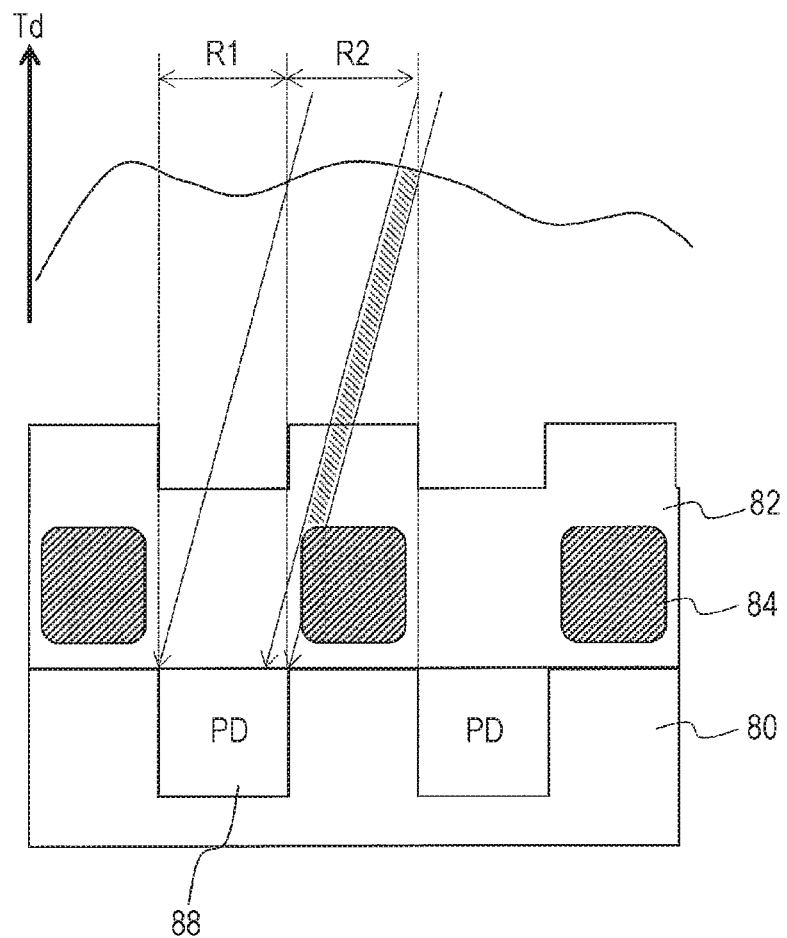
FIG. 36 is a view illustrating a sectional structure of a CCD image sensor and a distribution example of relative transmittance Td of the subject.

FIG. 36 illustrates a sectional structure of the CCD image sensor and a distribution example of relative transmittance Td of the subject. As illustrated in FIG. 36, the CCD image sensor roughly includes substrate 80, insulating layer 82 on substrate 80, and wiring 84 disposed in insulating layer 82. A plurality of photodiodes 88 are formed on substrate 80. A light shielding layer (not illustrated in FIG. 36) is formed on wiring 84. A transistor and the like are not illustrated in FIG. 36. The transistor and the like are also not illustrated in the following drawings. Roughly, a sectional structure near the photodiode of the surface irradiation CMOS image sensor is substantially similar to that near the photodiode of the CCD image sensor. Therefore, the description and illustration of the sectional structure of the surface irradiation CMOS image sensor are omitted.

As illustrated in FIG. 36, in the case that the illumination light is incident in the direction normal to the imaging surface, the irradiation light transmitted through region R1 immediately above photodiode 88 in the subject is incident on photodiode 88. On the other hand, the irradiation light transmitted through region R2 immediately above the light shielding layer on wiring 84 in the subject is incident on a light shielding region (a region where a light shielding film is formed) of the image sensor. Accordingly, the image indicating region R1 immediately above photodiode 88 in the subject is obtained in the case that the subject is irradiated with illumination light in the direction normal to the imaging surface.

In order to acquire the image indicating the region immediately above the light shielding film, the subject is irradiated with illumination light in the direction tilted with respect to the direction normal to the imaging surface such that the light transmitted through region R2 is incident on photodiode 88. At this point, depending on the irradiation direction, sometimes the light transmitted through region R2 is partially blocked by wiring 84. In the example of FIG. 36, the beam passing through a hatched portion does not reach photodiode 88. For this reason, the pixel value is slightly lowered in the oblique incident of the light. However, because the transmitted light is not wholly blocked, the high-resolution image can be formed using the obtained sub-images.

Figure 37A:
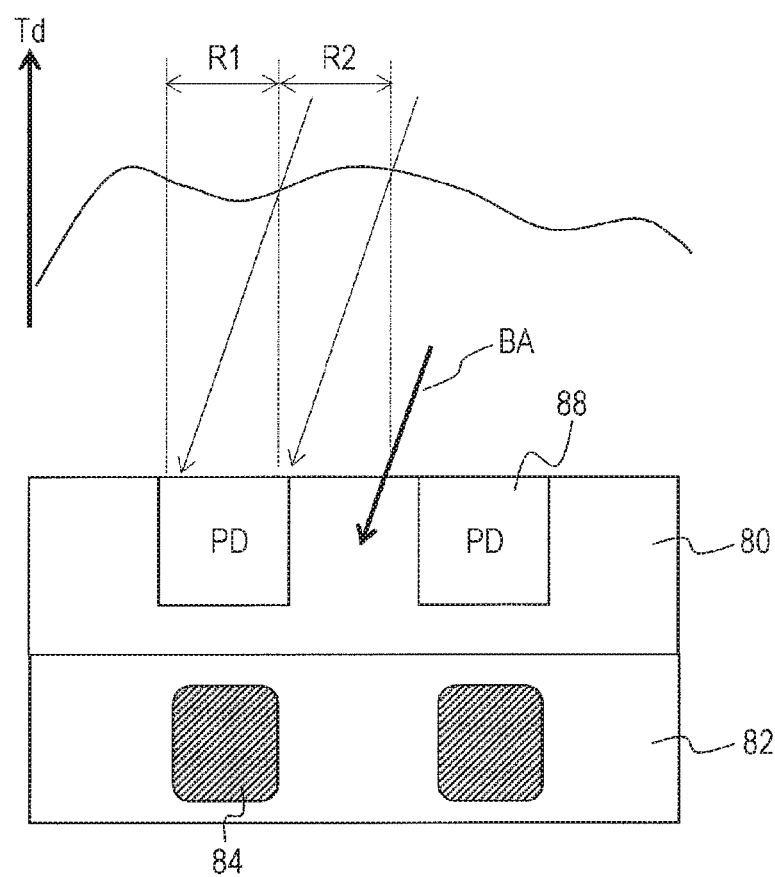
FIG. 37A is a view illustrating a sectional structure of a rear surface irradiation CMOS image sensor and a distribution example of relative transmittance Td of the subject.
Figure 37B:
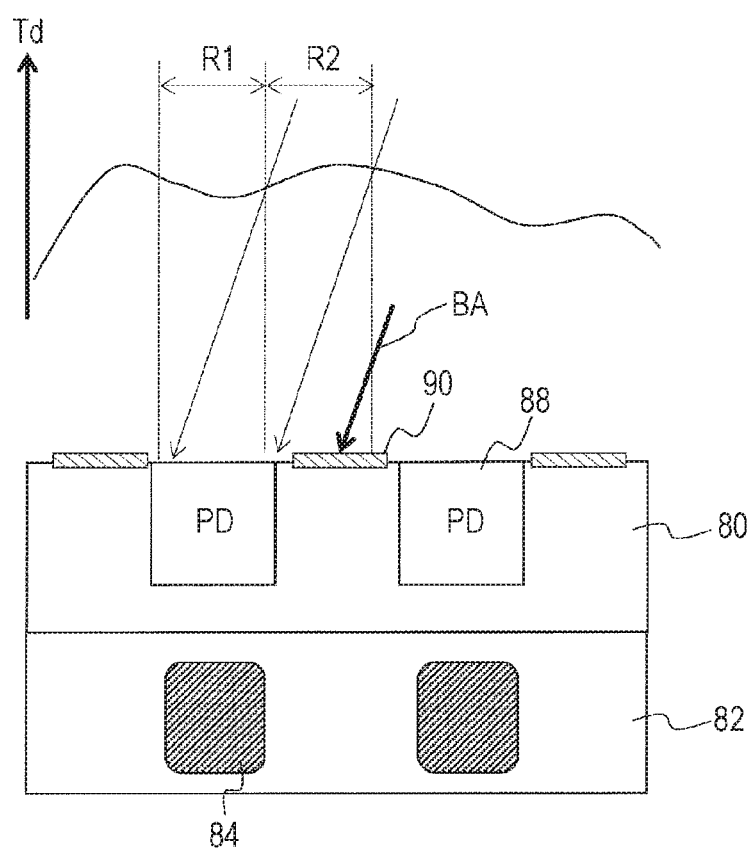
FIG. 37B is a view illustrating the sectional structure of the rear surface irradiation CMOS image sensor and a distribution example of relative transmittance Td of the subject.

FIGS. 37A and 37B illustrate a sectional structure of the rear surface irradiation CMOS image sensor and a distribution example of relative transmittance Td of the subject. As illustrated in FIG. 37A, in the rear surface irradiation CMOS image sensor, the transmitted light is not blocked by wiring 84 even in the oblique incident of the light. However, the light transmitted through a region different from a region to be imaged in the subject (light schematically indicated by a bold arrow BA in FIGS. 37A and 37B) is incident on substrate 80 to generate a noise, and possibly the sub-image quality is degraded. As illustrated in FIG. 37B, the degradation can be reduced by forming light shielding layer 90 on the region except for the region where the photodiode is formed in the substrate.

Figure 38:
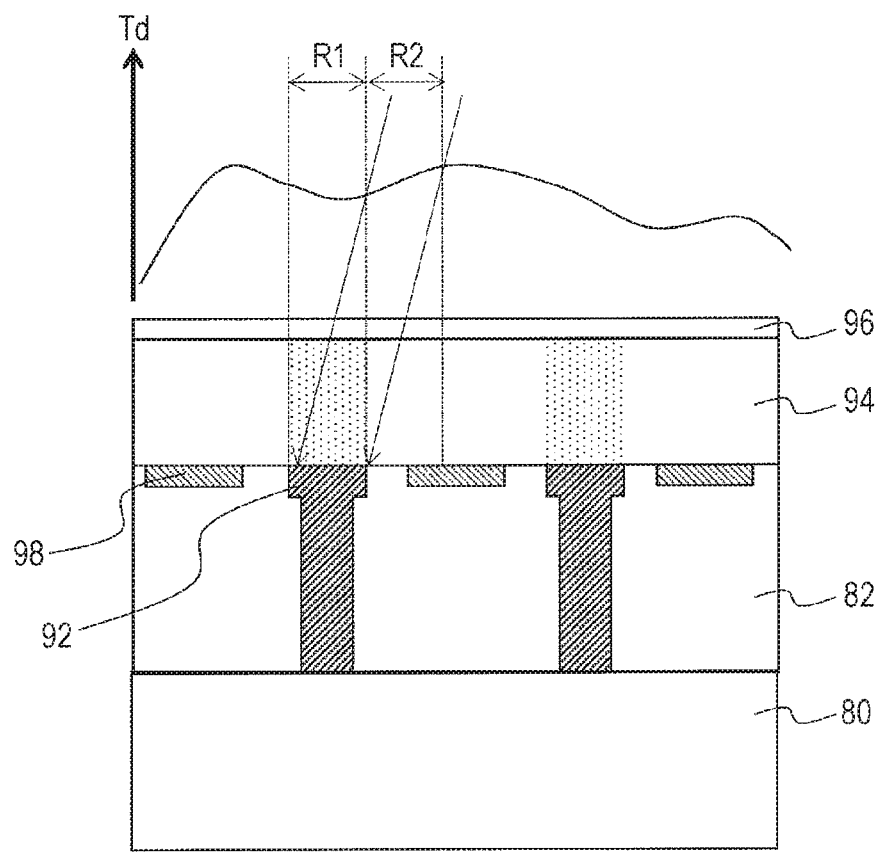
FIG. 38 is a view illustrating a sectional structure of a photoelectric conversion film laminated image sensor and a distribution example of relative transmittance Td of the subject.

FIG. 38 illustrates a sectional structure of an image sensor including a photoelectric conversion film made of an organic or inorganic material (hereinafter, referred to as a "photoelectric conversion film laminated image sensor") and an example of the distribution of relative transmittance Td of the subject.

As illustrated in FIG. 38, the photoelectric conversion film laminated image sensor roughly includes substrate 80, insulating layer 82 in which a plurality of pixel electrodes are provided, photoelectric conversion film 94 on insulating layer 82, and transparent electrode 96 on photoelectric conversion film 94. As illustrated in FIG. 38, in the photoelectric conversion film laminated image sensor, photoelectric conversion film 94 that performs photoelectric conversion is formed on substrate 80 (for example, the semiconductor substrate) instead of the photodiode formed on the semiconductor substrate. Typically, photoelectric conversion film 94 and transparent electrode 96 are formed over the whole imaging surface. A protective film protecting photoelectric conversion film 94 is not illustrated in FIG. 38.

In the photoelectric conversion film laminated image sensor, pixel electrode 92 collects a charge (electron or hole) generated by the photoelectric conversion of the light incident on photoelectric conversion film 94. Therefore, a value indicating the amount of light incident on photoelectric conversion film 94. Accordingly, in the photoelectric conversion film laminated image sensor, a unit region including one pixel electrode 92 corresponds to one pixel in the imaging surface. In the photoelectric conversion film laminated image sensor, similarly to the rear surface irradiation CMOS image sensor, the transmitted light is not blocked by the wiring even in the oblique incident of the light.

As described in FIGS. 1A to 6, the high-resolution image is formed using the plurality of sub-images indicating the images constructed with different parts of the subject. In the typical photoelectric conversion film laminated image sensor, because photoelectric conversion film 94 is formed over the whole imaging surface, the photoelectric conversion is generated in photoelectric conversion film 94 by the light transmitted through the region except for the desired region of the subject even in the perpendicular incident. When the excess electron or hole generated at that time is attracted to pixel electrode 92, the proper sub-image possibly cannot be obtained. Accordingly, it is beneficial that the charge generated in the region where pixel electrode 92 and transparent electrode 96 overlap each other (shading region in FIG. 38) is selectively attracted to pixel electrode 92.

In the configuration of FIG. 38, dummy electrode 98 corresponding to each pixel electrode 92 is provided in the pixel. During the acquisition of the subject image, a proper potential difference is provided between pixel electrode 92 and dummy electrode 98. Therefore, the charge generated in the region except for the region where pixel electrode 92 and transparent electrode 96 overlap each other can be attracted to dummy electrode 98, and the charge generated in the region where pixel electrode 92 and transparent electrode 96 overlap each other can selectively be attracted to pixel electrode 92. The similar effect can be obtained by patterning of transparent electrode 96 or photoelectric conversion film 94. In such configurations, a ratio of area S3 of pixel electrode 92 to area S1 of the pixel (S3/S1) corresponds to the numerical aperture.

As described above, the resolving power can be increased by at most N times when the numerical aperture of image sensor 4 is approximately equal to 1/N (N is an integer of 2 or more). In other words, the smaller numerical aperture has an advantage to increase the resolving power. In the photoelectric conversion film laminated image sensor, the ratio (S3/S1) corresponding to the numerical aperture can be adjusted by adjusting area S3 of pixel electrode 92. For example, the ratio (S3/S1) is set to a range of 10% to 50%. The photoelectric conversion film laminated image sensor in which the ratio (S3/S1) falls within the range can be used in the super-resolution.

As can be seen from FIGS. 36 and 37B, the surface facing the subject is not flat in the CCD image sensor and the surface irradiation CMOS image sensor. For example, a step exists in the surface of the CCD image sensor. In the rear surface irradiation CMOS image sensor, it is necessary to provide the patterned light shielding layer on the imaging surface in order to acquire the sub-image used to form the high-resolution image, but the surface facing the subject is not flat.

On the other hand, the photoelectric conversion film laminated image sensor has a substantially flat imaging surface as illustrated in FIG. 38. Accordingly, the subject deformation caused by the shape of the imaging surface is hardly generated even in the case that the subject is disposed on the imaging surface. In other words, the sub-image is acquired using the photoelectric conversion film laminated image sensor, which allows the observation of the detailed structure of the subject.

Various modes described above can be combined as long as inconsistency is not generated.

The exemplary embodiment of the present disclosure provides at least one of the image acquisition device, the image forming method, and the image forming system for facilitating application of the technology of high resolving power exceeding the intrinsic resolving power of the image sensor. For example, the high-resolution image provides useful information in the scene of the pathological diagnosis.

REFERENCE SIGNS LIST 2 subject
7 imaging element
8 transparent plate
10 module
30 lighting system
31 light source
32 stage
33 stage driving mechanism
40a to 40f irradiation direction decision section
100a to 100f image acquisition device
150 image processing device
500 image forming system

What is claimed is:
1. An image forming system comprising:
 an image acquisition device comprising:
  a lighting system that sequentially irradiates a subject of a module with illumination light in a plurality of different irradiation directions;
  an imaging element for acquiring a plurality of images according to the plurality of different irradiation directions, the subject and the imaging element being integrated with each other in the module such that illumination light transmitted through the subject is incident on the imaging element; and
  an irradiation direction decision section that decides the plurality of different irradiation directions based on a difference between a first preliminary image and a second preliminary image before the imaging element acquires the plurality of images according to the plurality of different irradiation directions, the first preliminary image being acquired with the imaging element when the subject is irradiated with first illumination light in a first irradiation direction, the second preliminary image being acquired with the imaging element when the subject is irradiated with second illumination light in a second irradiation direction; and an image processing device that synthesizes the plurality of images acquired according to the plurality of different irradiation directions determined by the irradiation direction decision section to form a high-resolution image of the subject, the high-resolution image having a resolving power higher than a resolving power of each of the plurality of images.

2. The image forming system according to claim 1, wherein the irradiation direction decision section is configured to decide the plurality of different irradiation directions based on the first and second irradiation directions that are selected such that the difference between the first and second preliminary images is smaller than a predetermined level.

3. The image forming system according to claim 2, wherein:
the lighting system changes at least one of the first and second irradiation directions,
the imaging element acquires at least one first preliminary image and at least one second preliminary image according to the change in the at least one of the first and second irradiation directions, and
the irradiation direction decision section decides an image set in which the difference between the first and second preliminary images is smaller than the predetermined level from at least one image set that includes the first and second preliminary images, and decides the plurality of different irradiation directions based on the first and second irradiation directions corresponding to the decided image set.

4. The image forming system according to claim 1, wherein:
the lighting system changes at least one of the first and second irradiation directions,
the imaging element acquires at least one first preliminary image and at least one second preliminary image according to the change in the at least one of the first and second irradiation directions, and
the irradiation direction decision section decides an image set in which the difference between the first and second preliminary images is minimized from a predetermined number of different image sets each of which includes the first and second preliminary images, and decides the plurality of different irradiation directions based on the first and second irradiation directions corresponding to the decided image set.

5. The image forming system according to claim 1, wherein the first irradiation direction and the second irradiation direction have a symmetrical relationship with respect to the subject.

6. The image forming system according to claim 1, wherein the difference is an amount defined by a pixel luminance in the first preliminary image and a pixel luminance in the second preliminary image.

7. The image forming system according to claim 1, wherein the irradiation direction decision section calculates the difference between the first and second preliminary images by comparing luminance values of a plurality of pixels constituting the first preliminary image and luminance values of a plurality of pixels constituting the second preliminary image.

8. The image forming system according to claim 6, wherein the irradiation direction decision section calculates the difference between the first and second preliminary images after correcting the pixel luminance in at least one of the first and second preliminary images.

9. The image forming system according to claim 1, wherein the irradiation direction decision section is configured to acquire position information indicating a height of the subject relative to the imaging element, and decide the plurality of different irradiation directions according to the position information.

10. The image forming system according to claim 1, wherein the lighting system includes a stage on which the module is detachably loaded and a stage driving mechanism that can change an attitude of the stage.

11. An image forming method comprising:
acquiring a first preliminary image of a subject by irradiating a module with first illumination light in a first irradiation direction, the subject and an imaging element being integrated with each other in the module such that the illumination light transmitted through the subject is incident on the imaging element;
acquiring a second preliminary image of the subject by irradiating the module with second illumination light in a second irradiation direction;
deciding a plurality of different irradiation directions relative to the subject based on a difference between the first and second preliminary images;
acquiring a plurality of images according to the plurality of different irradiation directions by sequentially irradiating the subject with the illumination light in the decided plurality of different irradiation directions; and
forming a high-resolution image of the subject by synthesizing the plurality of images, the high-resolution image having a resolving power higher than a resolving power of each of the plurality of images.

12. The image forming method according to claim 11, wherein acquiring the first preliminary image is performed a plurality of times while the first irradiation direction is changed.

13. The image forming method according to claim 12, wherein acquiring the second preliminary images is performed a plurality of times while the second irradiation direction is changed.

14. The image forming method according to claim 11, wherein the first irradiation direction and the second irradiation direction have a symmetrical relationship with respect to the subject.

15. The image forming method according to claim 11, wherein, in deciding the plurality of different irradiation directions, the plurality of different irradiation directions are decided based on the first and second irradiation directions in which the difference between the first and second preliminary images is smaller than a predetermined level.

16. The image forming method according to claim 11, wherein, in deciding the plurality of different irradiation directions, the plurality of different irradiation directions are decided based on the first and second irradiation directions in which the difference between the first and second preliminary images is minimized.

17. The image forming method according to claim 11, wherein the difference is an amount defined by a pixel luminance in the first preliminary image and a pixel luminance in the second preliminary image.

18. The image forming method according to claim 11, wherein deciding the plurality of different irradiation directions includes comparing luminance values of a plurality of pixels constituting the first preliminary image to luminance values of a plurality of pixels constituting the second preliminary image.

19. The image forming method according to claim 11, further comprising correcting the pixel luminance in the second preliminary image between acquiring the second preliminary image and deciding the plurality of different irradiation directions.

20. An image acquisition device comprising:
an imaging element;
one or more memories; and
circuitry which, in operation,
acquires a first preliminary image of a subject by irradiating a module with first illumination light in a first irradiation direction to store the first preliminary image on the one or more memories, wherein the subject and the imaging element are integrated with each other in the module such that the illumination light transmitted through the subject is incident on the imaging element;
acquires a second preliminary image of the subject by irradiating the module with second illumination light in a second irradiation direction to store the second preliminary image on the one or more memories;
decides a plurality of different irradiation directions relative to the subject based on a difference between the first and second preliminary images;
acquires a plurality of images according to the plurality of different irradiation directions by sequentially irradiating the subject with the illumination light in the decided plurality of different irradiation directions; and
forms a high-resolution image of the subject by synthesizing the plurality of images, the high-resolution image having a resolving power higher than a resolving power of each of the plurality of images.

21. The image acquisition device according to claim 20, wherein the circuitry acquires a plurality of the first preliminary images each having a different first irradiation direction.

22. The image acquisition device according to claim 21, wherein the circuitry acquires a plurality of the second preliminary images each having a different second irradiation direction.

23. The image acquisition device according to claim 20, wherein the first irradiation direction and the second irradiation direction have a symmetrical relationship with respect to the subject.

24. The image acquisition device according to claim 20, wherein the plurality of different irradiation directions are decided based on the first and second irradiation directions in which the difference between the first and second preliminary images is smaller than a predetermined level.

25. The image acquisition device according to claim 20, wherein the plurality of different irradiation directions are decided based on the first and second irradiation directions in which the difference between the first and second preliminary images is minimized.

26. The image acquisition device according to claim 20, wherein the difference is an amount defined by a pixel luminance in the first preliminary image and a pixel luminance in the second preliminary image.

27. The image acquisition device according to claim 20, wherein the plurality of different irradiation directions is decided based on comparison luminance values of a plurality of pixels constituting the first preliminary image to luminance values of a plurality of pixels constituting the second preliminary image.

28. The image acquisition device according to claim 20, wherein:
the circuitry further corrects the pixel luminance in the second preliminary image in operation, and
the plurality of different irradiation directions are decided based on the difference between the first preliminary image and the second preliminary image having the corrected the pixel luminance.

\* \* \* \* \*